(12) United States Patent
Dehmlow et al.

(10) Patent No.: US 7,485,652 B2
(45) Date of Patent: Feb. 3, 2009

(54) INDOLYL DERIVATIVES AS LIVER-X-RECEPTOR (LXR) MODULATORS

(75) Inventors: Henrietta Dehmlow, Grenzach-Wyhlen (DE); Bernd Kuhn, Liestal (CH); Narendra Panday, Basel (CH); Hasane Ratni, Habsheim (FR); Tanja Schulz-Gasch, Liestal (CH); Matthew Blake Wright, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/636,925

(22) Filed: Dec. 11, 2006

(65) Prior Publication Data

US 2007/0099916 A1 May 3, 2007

Related U.S. Application Data

(62) Division of application No. 11/115,942, filed on Apr. 27, 2005, now Pat. No. 7,173,048.

(30) Foreign Application Priority Data

May 3, 2004 (EP) .................. 04101889

(51) Int. Cl.
*A61K 31/4439* (2006.01)
*A61K 31/422* (2006.01)
*A61K 31/404* (2006.01)

(52) U.S. Cl. .................. 514/340; 514/374; 514/414
(58) Field of Classification Search .................. 514/340, 514/374, 414, 415
See application file for complete search history.

(56) References Cited

U.S. PATENT DOCUMENTS 6,472,386 B1 10/2002 Kodama et al.

FOREIGN PATENT DOCUMENTS

| GB | 1583249 | 1/1981 |
|---|---|---|
| JP | 9095482 | 8/1997 |
| WO | WO9719311 | 5/1997 |
| WO | WO02092084 | 11/2002 |
| WO | WO2004006922 | 1/2004 |

OTHER PUBLICATIONS

Bennett et al. (Exp. Opin. Ther. Patents 2006, 16(12), 1673-1699).*
Geyeregger et al. (Cell. Mol. Life Sci. 2006, 63, 524-539).*
Michael et al. (Mini-Reviews in Med. Chem. 2005, 5, 729-740).*
Wang et al. Journal of Lipid Research 2005, 46, 2377-2387.*
Fluhr et al. The Journal of Investigative Dermatology 2005, 125, 1206-1214.*
Lund et al. Arteriosclerosis, Thrombosis, and Vascular Biology 2003, 23, 1169-1177.*
HHMI Bulletin, Sep. 2003.*
Willy et al., Genes Dev. 1995, 9:1033-45.
Song et al., Proc Natl Acad Sci USA.1994, 91:10809-13.
Miller Ne., Lipids 1978,13:914-9.
Gordon et al., Am J Med. 1977, 62:707-14.
Lund et al., Arterioscler. Thromb. Vasc. Biol. 2003, 23:1169-77.
Joseph and Tontonoz, Curr. Opin. Pharmacol. 2003, 3:192-7.
Cao et al., J Biol Chem. 2003, 278:1131-6.
Chini et al., J. Org. Chem., 1991, 56(20) 5939-5942.
Duran Pachon et al., Tet. Lett., 2003, 44(32) 6025-6027.
Sundermeyer et al., Chemistry an European Journal, 2003, 9(8), 1828-1836.
Brown et al., Tet. Lett., 2001, 2 (6), 983-985.
Kanekiyo et al., Heterocycles, 2000, 53 (9), 1877-1880.
Pearlstein et al., Bioorg. and Med. Chem. Lett., 2003, 13, 1829-1835.
Mewshaw et al., Bioorg. and Med. Chem. Lett., 2002, 12, 307-310.
Sakagani et al., Synlett. 1996, 163-164.
Maryanoff et al., Chem. Rev., 1989, 89, 863-927.
Saravan et al., Tet. Lett. 1998, 39 (22), 3823-3824.
Togo et al., Syn. Lett., 2003, 702-704.
Durley et al., J. Med. Chem., 2002, 45, 18, 3891-3904.
Tian et al., Org. Lett., 3, 12, 2001, 1929-1932.
Cynkowski et al., J. Chem. Soc. Chem. Commun., 1995, 2335-2336.
Faul et al., Heterocycles, 2001, 55 (4), 689-704.
Olofsson et al. J. Org. Chem., 1998, 65 (15), 5076-5079.
Buchwald et al., J. Org. Chem., 2000, 65 ( 4), 1158-1174.
Takagi et al., Chem. Lett., 1989, 11, 1957-58.
Bennett, D.J., et al., Expert Opin. Ther. Patents, vol. 14, No. 7, pp. 967-982 (2004), XP002342352.

* cited by examiner

*Primary Examiner*—Kamal A Saeed
*Assistant Examiner*—Jason Nolan
(74) *Attorney, Agent, or Firm*—George W. Johnston; Dennis P. Tramaloni; Samuel H. Megerditchian

(57) ABSTRACT

The invention relates to compounds of formula (I):

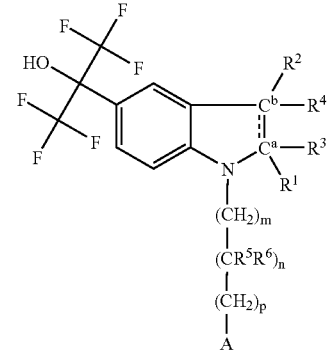

and pharmaceutically acceptable salts and pharmaceutically acceptable esters thereof, wherein $R^1$, $R^2$, $R^3$, $R^4$, $R^5$, $R^6$, A, m, n and p are defined as in claim 1. These compounds can be used as pharmaceutical compositions for the treatment of, for example, diabetes.

2 Claims, No Drawings

INDOLYL DERIVATIVES AS LIVER-X-RECEPTOR (LXR) MODULATORS

PRIORITY TO RELATED APPLICATIONS

This application is a division of U.S. application Ser. No. 11/115,942, filed Apr. 27, 2005, now pending, the entire content of which is hereby incorporated by reference.

FIELD OF THE INVENTION

The present invention is concerned with novel indole derivatives of the formula (I):

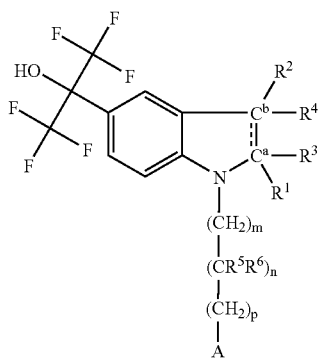

and pharmaceutically acceptable salts and pharmaceutically acceptable esters thereof.

The compounds of the formula I are useful as liver-X-receptor modulators.

All documents cited or relied upon below are expressly incorporated herein by reference.

BACKGROUND OF THE INVENTION

Liver-X-Receptors (LXRs) are members of the nuclear hormone receptor superfamily. The LXRs are activated by endogenous oxysterols and regulate the transcription of genes controlling multiple metabolic pathways. Two subtypes, LXRalpha and LXRbeta, have been described (Willy et al., Genes Dev. 1995, 9:1033-45; Song et al., Proc Natl Acad Sci USA.1994, 91:10809-13). LXRbeta is ubiquitously expressed, while LXRalpha is predominantly expressed in cholesterol metabolizing tissues such as the liver, adipose, intestine and macrophage. The LXRs modulate a variety of physiological responses including regulation of cholesterol absorption, cholesterol elimination (bile acid synthesis), and transport of cholesterol from peripheral tissues via plasma lipoproteins to the liver. The LXRs are also involved in glucose metabolism, cholesterol metabolism in the brain, cell differentiation, and inflammation.

At present, approximately half of all patients with coronary artery disease have low concentrations of plasma high-density lipoprotein cholesterol (HDL-C). The atheroprotective function of HDL was first highlighted almost 25 years ago and stimulated exploration of the genetic and environmental factors that influence HDL-C levels (Miller NE., Lipids 1978, 13:914-9). The protective function of HDL derives from its role in a process termed reverse cholesterol transport. HDL mediates the removal of cholesterol from cells in peripheral tissues, including macrophage foam cells in the atherosclerotic lesions of the arterial wall. HDL delivers its cholesterol to the liver and sterol-metabolizing organs for conversion to bile and elimination in feces. Studies have shown that HDL-C levels are predictive of coronary artery disease risk independently of low-density lipoprotein cholesterol (LDL-C) levels (Gordon et al., Am J Med. 1977, 62:707-14).

At present, the estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial unfavorable side-effects limit the therapeutic potential of this approach.

It has been observed that as many as 90% of the 14 million diagnosed type 2 diabetic patients in the United States are overweight or obese, and a high proportion of type 2 diabetic patients have abnormal concentrations of lipoproteins. Studies have shown that the prevalence of total cholesterol >240 mg/dl is 37% in diabetic men and 44% in women. The rates for LDL-C>160 mg/dl are 31% and 44%, and for HDL-C<35 mg/dl are 28% and 11%, in diabetic men and women respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and has been shown to afflict 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in the later stages of the disease, due to exhaustion and failure of pancreatic insulin-producing capacity. Thus, T2D is a cardiovascular-metabolic syndrome associated with multiple co-morbidities, including insulin resistance, dyslipidemia, hypertension, endothelial dysfunction and inflammatory atherosclerosis.

The first line of treatment for dyslipidemia and diabetes at present generally involves a low-fat and low-glucose diet, exercise and weight loss. However, compliance can be moderate, and as the disease progresses, treatment of the various metabolic deficiencies becomes necessary with lipid-modulating agents such as statins and fibrates for dyslipidemia, and hypoglycemic drugs, e.g. sulfonylureas, metformin, or insulin sensitizers of the thiazolidinedione (TZD) class of PPARγ-agonists, for insulin resistance. Recent studies provide evidence that modulators of LXRs would result in compounds with enhanced therapeutic potential, and as such, modulators of LXRs should improve the plasma lipid profile, and raise HDL-C levels (Lund et al., Arterioscler. Thromb. Vasc. Biol. 2003, 23:1169-77). LXRs are also known to control the efflux of cholesterol from the macrophage foam cell of the atherosclerotic lesion, and agonists of LXRs have been shown to be atheroprotective (Joseph and Tontonoz, Curr. Opin. Pharmacol. 2003, 3:192-7). Thus, modulators of LXRs would be effective treatments for the atherosclerotic disease which underlies the cardiovascular morbidity and mortality of stroke and heart disease. Recent observations also suggest that there is an independent LXR mediated effect on insulin-sensitization in addition to its role in atheroprotection (Cao et al., J Biol Chem. 2003, 278:1131-6). Thus LXR modulators can also show superior therapeutic efficacy on HDL-raising and atheroprotection, with additional effects on diabetes, compared to current therapies.

SUMMARY OF THE INVENTION

The present invention relates to a method for the treatment and prophylaxis of diseases which are modulated by LXR alpha and/or LXR beta agonists, comprising the step of administering a therapeutically effective amount of a compound according to formula (I):

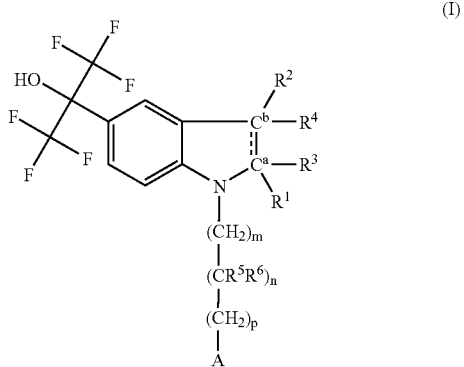

wherein $R^1$ is hydrogen, alkyl, halogen, formyl, hydroxyalkyl or trifluoromethyl;
$R^2$ is hydrogen, alkyl, alkenyl, alkynyl, cyano or halogen;
$R^3$ is hydrogen or alkyl;
$R^4$ is hydrogen, alkyl, hydroxy or alkoxy;
$R^5$ and $R^6$ are independently selected from hydrogen, alkyl, arylalkyl, heteroarylalkyl, hydroxyalkyl, alkoxycarbonyl, aryl and heteroaryl;
A is aryl or heterocyclyl, wherein aryl and heterocyclyl are optionally substituted with one to three substituents independently selected from alkyl, halogen, amino, hydroxyalkyl, aryl, aryloxy, alkoxy, arylalkyl, arylalkenyl, alkoxycarbonylamino, aminocarbonyloxy, carboxy, alkoxycarbonyl, alkoxycarbonylalkyl, aminoalkyl, trifluoromethyl, arylalkylaminocarbonyl, alkoxycarbonylalkylaminocarbonyl, indolylalkylaminocarbonyl, morpholinylcarbonyl, aminocarbonyl, aminocarbonylalkyl, aminocarbonylalkoxy, alkoxycarbonylalkoxy, pyridinylalkylaminocarbonyl, alkyloxycarbonylalkylaryl, alkyloxycarbonylalkoxyaryl, carboxyalkylaryl, carboxyalkoxyaryl, aminocarbonylalkylaryl, aminocarbonylalkoxyaryl, aminocarbonylamino, aminocarbonyloxy, aminocarbonyloxyaryl, carboxyalkyl, carboxyalkoxy, cycloalkylaminocarbonyl, morpholinylcarbonyloxyaryl, morpholinylcarbonylaryl, arylalkoxyaryl, aminocarbonylaryl, pyrrolidinylcarbonyloxyaryl, pyrrolidinylcarbonylaryl, piperidinylcarbonylaryl, piperidinylcarbonyloxyaryl, hydroxyalkylaryl, hydroxy(carboxy)alkylaryl, hydroxy(alkoxycarbonyl)alkylaryl, hydroxy(aminocarbonyl)alkylaryl and pyridinyl;
m is zero, 1, 2 or 3;
n is zero or 1;
p is zero, 1, 2 or 3; with the proviso that the sum of m, n and p is 1, 2, 3 or 4;
and, wherein the compound is not 2-(1-benzyl-2,3-dihydro-1H-indol-5-yl)-1,1,1,3,3,3-hexafluoro-propan-2-ol;
and, wherein the bond between the carbon atoms $C^a$ and $C^b$ is a carbon carbon single or double bond and in case the bond between $C^a$ and $C^b$ is a carbon carbon double bond $R^3$ and $R^4$ are absent;

and pharmaceutically acceptable salts and pharmaceutically acceptable esters thereof, to a patient in need thereof.

DETAILED DESCRIPTION

The novel compounds of the present invention have been found to bind to and selectively activate LXR alpha and LXR beta or coactivate LXR alpha and LXR beta. Consequently, cholesterol absorption is reduced, HDL cholesterol is increased, and inflammatory atherosclerosis is reduced. Since multiple facets of combined dyslipidemia and cholesterol homeostasis are addressed by LXR modulators, novel compounds of the present invention have an enhanced therapeutic potential compared to the compounds already known in the art. They can therefore be used in the treatment and prophylaxis of diseases which are modulated by LXR alpha and/or LXR beta agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, Alzheimer's disease, sepsis, and inflammatory diseases such as colitis, pancreatitis, cholestasis/fibrosis of the liver, psoriasis and other inflammatory diseases of the skin, and diseases that have an inflammatory component such as Alzheimer's disease or impaired/improvable cognitive function. Moreover, the novel compounds of the present invention can be used for treatment and prophylaxis of age-related and inherited (e.g. Stargardt's disease) forms of macular degeneration.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, preferably methoxy and ethoxy and most preferred methoxy.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-$SO_2$—, amino-$SO_2$—, cycloalkyl and the like. Preferred is phenyl or naphthyl, particularly phenyl optionally substituted with one to three, preferably one or two substituents independently selected from alkyl, trifluoromethyl, halogen, alkoxycarbonyl, aminoalkyl, alkoxy, hydroxyl, carboxy and hydroxyalkyl. Particularly preferred is phenyl.

The term "heterocyclyl", alone or in combination signifies a saturated, partially unsaturated or aromatic 5- to 10-membered heterocycle which contains one or more hetero atoms selected from nitrogen, oxygen and sulphur. If desired, it can be substituted on one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e.=N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl) and quinoxalinyl. Preferred are oxazolyl, quinolinyl, thiazolyl, benzothiophenyl, pyridinyl, 2H-pyrazol-3-yl and isoxazolyl. Particularly preferred are oxazol-2-yl and oxazol-4-yl.

The term "heteroaryl", alone or in combination, signifies aromatic 5- to 10-membered heterocycle which comprises one or more, preferably one or two, particularly preferred one hetero atom selected from nitrogen, oxygen and sulfur, wherein nitrogen is preferred. It can be substituted on one or more carbon atoms e.g. by cyano, trifluoromethyl, trifluoromethoxy, alkyl-$SO_2$—, amino-$SO_2$—, halogen, alkoxy, hydroxy, amino, cycloalkyl, alkylcarbonyl, aminocarbonyl, nitro, alkyl, and/or alkoxycarbonyl. Examples of heteroaryl cycles are thiophenyl or pyrrolidinyl, wherein thiophenyl and pyrrolidinyl are optionally substituted with one to three substituents, preferably one or two independently selected from alkyl, halogen, alkoxy, trifluoromethoxy, nitro and trifluoromethyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "halogen" signifies fluorine, chlorine, bromine or iodine and preferably fluorine, chlorine or bromine.

The term "carbonyl", alone or in combination signifies the —C(O)— group.

The term "nitro", alone or in combination signifies the —$NO_2$ group.

The term "cyano", alone or in combination signifies the group —CN.

The term "formyl", alone or in combination signifies the group —CHO.

The term "alkenyl", alone or in combination signifies a straight-chain or branched-chain hydrocarbon group comprising a carbon carbon double bond and 2 to 10, preferably 2 to 8 carbon atoms, more preferably 2 to 4 carbon atoms. Preferred examples are ethenyl and allyl.

The term "alkynyl", alone or in combination signifies a straight-chain or branched-chain hydrocarbon group comprising a carbon carbon triple bond and 2 to 10, preferably 2 to 8 carbon atoms, more preferably 2 to 4 carbon atoms. Preferred examples are ethynyl and propynyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. The compound of formula (I) can also be present in the form of zwitterions. Particularly preferred pharmaceutically acceptable salts of compounds of formula (I) are the hydrochloride salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In detail, the present invention is concerned with compounds of formula (I),

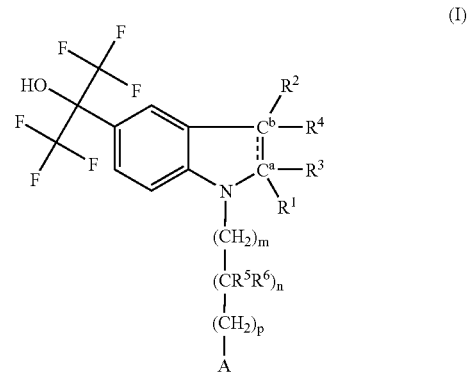

wherein $R^1$ is hydrogen, alkyl, halogen, formyl, hydroxyalkyl or trifluoromethyl;

$R^2$ is hydrogen, alkyl, alkenyl, alkynyl, cyano or halogen;

$R^3$ is hydrogen or alkyl;

$R^4$ is hydrogen, alkyl, hydroxy or alkoxy;

$R^5$ and $R^6$ are independently selected from hydrogen, alkyl, arylalkyl, heteroarylalkyl, hydroxyalkyl, alkoxycarbonyl, aryl and heteroaryl;

A is aryl or heterocyclyl, wherein aryl and heterocyclyl are optionally substituted with one to three substituents independently selected from alkyl, halogen, amino, hydroxyalkyl, aryl, aryloxy, alkoxy, arylalkyl, arylalkenyl, alkoxycarbonylamino, aminocarbonyloxy, carboxy, alkoxycarbonyl, alkoxycarbonylalkyl, aminoalkyl, trifluoromethyl, arylalkylaminocarbonyl, alkoxycarbonylalkylaminocarbonyl, indolylalkylaminocarbonyl, morpholinylcarbonyl, aminocarbonyl, aminocarbonylalkyl, aminocarbonylalkoxy, alkoxycarbonylalkoxy, pyridinylalkylaminocarbonyl, alkyloxycarbonylalkylaryl, alkyloxycarbonylalkoxyaryl, carboxyalkylaryl, carboxyalkoxyaryl, aminocarbonylalkylaryl, aminocarbonylalkoxyaryl, aminocarbonylamino, aminocarbonyloxy, aminocarbonyloxyaryl, carboxyalkyl, carboxyalkoxy, cycloalkylaminocarbonyl, morpholinylcarbonyloxyaryl, morpholinylcarbonylaryl, arylalkoxyaryl, aminocarbonylaryl, pyrrolidinylcarbonyloxyaryl, pyrrolidinylcarbonylaryl, piperidinylcarbonylaryl, piperidinylcarbonyloxyaryl, hydroxyalkylaryl, hydroxy(carboxy)alkylaryl, hydroxy(alkoxycarbonyl)alkylaryl, hydroxy(aminocarbonyl)alkylaryl and pyridinyl;

m is zero, 1, 2 or 3;

n is zero or 1;

p is zero, 1, 2 or 3; with the proviso that the sum of m, n and p is 1, 2, 3 or 4;

and, wherein the compound is not 2-(1-benzyl-2,3-dihydro-1H-indol-5-yl)-1,1,1,3,3,3-hexafluoro-propan-2-ol;

and, wherein the bond between the carbon atoms $C^a$ and $C^b$ is a carbon carbon single or double bond and in case the bond between $C^a$ and $C^b$ is a carbon carbon double bond $R^3$ and $R^4$ are absent;

and pharmaceutically acceptable salts and pharmaceutically acceptable esters thereof.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

Preferred are the compounds of formula (I) and pharmaceutically acceptable salts thereof, particularly the compounds of formula (I).

Preferred compounds of formula (I) are those, wherein:

$R^1$ is hydrogen, alkyl, halogen, formyl, hydroxyalkyl or trifluoromethyl;

$R^2$ is hydrogen, alkyl, alkenyl, alkynyl, cyano or halogen;

$R^3$ is hydrogen or alkyl;

$R^4$ is hydrogen, alkyl, hydroxy or alkoxy;

$R^5$ and $R^6$ are independently selected from hydrogen, alkyl, arylalkyl, heteroarylalkyl, hydroxyalkyl, alkoxycarbonyl, aryl and heteroaryl;

A is aryl or heterocyclyl, wherein aryl and heterocyclyl are optionally substituted with one to three substituents independently selected from alkyl, halogen, amino, hydroxyalkyl, aryl, aryloxy, alkoxy, arylalkyl, alkoxycarbonylamino, aminocarbonyloxy, carboxy, alkoxycarbonyl, alkoxycarbonylalkyl, aminoalkyl, trifluoromethyl, arylalkylaminocarbonyl, alkoxycarbonylalkylaminocarbonyl, indolylalkylaminocarbonyl, morpholinylcarbonyl, aminocarbonyl, aminocarbonylalkyl, aminocarbonylalkoxy, alkoxycarbonylalkoxy, pyridinylalkylaminocarbonyl, alkyloxycarbonylalkylaryl, alkyloxycarbonylalkoxyaryl, carboxyalkylaryl, carboxyalkoxyaryl, aminocarbonylalkylaryl, aminocarbonylalkoxyaryl, aminocarbonylamino, aminocarbonyloxy, aminocarbonyloxyaryl, carboxyalkyl, carboxyalkoxy, cycloalkylaminocarbonyl, morpholinylcarbonyloxyaryl, morpholinylcarbonylaryl, arylalkoxyaryl, aminocarbonylaryl, pyrrolidinylcarbonyloxyaryl, pyrrolidinylcarbonylaryl, piperidinylcarbonylaryl, piperidinylcarbonyloxyaryl; hydroxyalkylaryl, hydroxy(carboxy)alkylaryl, hydroxy(alkoxycarbonyl)alkylaryl, hydroxy(aminocarbonyl)alkylaryl and pyridinyl;

m is zero, 1, 2 or 3;

n is zero or 1;

p is zero, 1, 2 or 3; with the proviso that the sum of m, n and p is 1, 2, 3 or 4;

and, wherein the compound is not 2-(1-benzyl-2,3-dihydro-1H-indol-5-yl)-1,1,1,3,3,3-hexafluoro-propan-2-ol;

and, wherein the bond between the carbon atoms $C^a$ and $C^b$ is a carbon carbon single or double bond and in case the bond between $C^a$ and $C^b$ is a carbon carbon double bond $R^3$ and $R^4$ are absent;

and pharmaceutically acceptable salts and pharmaceutically acceptable esters thereof.

Further preferred are compounds according to formula (I), wherein $R^1$ is alkyl, halogen, formyl or hydroxyalkyl. Also preferred are compounds of formula (I), wherein $R^1$ is hydrogen, alkyl, halogen, hydroxyalkyl or trifluoromethyl. Moreover, preferred are compounds of formula (I), wherein $R^1$ is hydrogen, methyl, chloro, iodo, formyl, hydroxymethyl, hydroxyethyl or hydroxypropyl. Particularly preferred are those compounds according to formula (I), wherein $R^1$ is methyl.

Preferred are compounds of formula (I), wherein $R^2$ is hydrogen, alkyl, alkenyl, alkynyl or halogen. Further preferred are the compounds of formula (I), wherein $R^2$ is hydrogen, alkyl or halogen. Moreover, preferred are the compounds of formula (I), wherein $R^2$ is hydrogen, methyl or halogen. Another preferred aspect of the present invention are compounds of formula (I), wherein $R^2$ is alkyl or halogen. Particularly preferred are those compounds of formula (I), wherein $R^2$ is hydrogen.

Further preferred are compounds of formula (I), wherein $R^3$ is alkyl, particularly methyl. Particularly preferred are those compounds of formula (I), wherein $R^3$ is hydrogen.

Another preferred aspect of the present invention are the compounds according to formula (I), wherein $R^4$ is hydrogen or alkyl, particularly methyl. Particularly preferred are those compounds of formula 1, wherein $R^4$ is hydrogen.

Further preferred are the compounds of formula (I), wherein $R^5$ and $R^6$ are independently selected from hydrogen, hydroxyalkyl and aryl. Another preferred aspect of the present invention are the compounds of formula (I), wherein $R^5$ and $R^6$ are independently selected from hydrogen, hydroxymethyl and phenyl. Particularly preferred are the compounds of formula (I), wherein one of $R^5$ and $R^6$ is hydrogen and the other one is hydroxyalkyl or aryl. Also preferred are the compounds of formula (I), wherein one of $R^5$ and $R^6$ is hydrogen and the other one is hydroxymethyl or phenyl.

Preferred are compounds of formula (I), wherein m is zero, 1 or 2. Further preferred are the compounds of formula (I), wherein m is 1 or 2. Particularly preferred are the compounds of formula (I), wherein m is zero or 1. Other preferred compounds of formula (I) are those, wherein m is 1, n is zero and p is zero.

Further preferred are the compounds of formula (I), wherein n is 1. Particularly preferred are those compounds of formula (I), wherein n is zero.

Preferred are the compounds of formula (I), wherein p is zero, 1 or 2. Further preferred are those compounds of formula (I), wherein p is zero or 1. Particularly preferred are those compounds of formula (I), wherein p is 1.

Moreover, preferred are the compounds of formula (I), wherein the bond between the carbon atoms $C^a$ and $C^b$ is a carbon carbon single bond. Those compounds are of formula

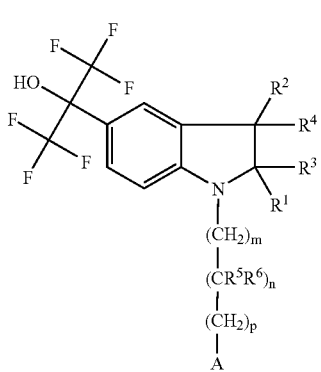

(Ia)

wherein $R^1$, $R^2$, $R^3$, $R^4$, $R^5$, $R^6$, A, m, n and p are defined as before.

Particularly preferred are those compounds of formula (Ia), wherein
$R^1$ is hydrogen, alkyl, formyl or hydroxyalkyl and
$R^2$, $R^3$, $R^4$, $R^5$, $R^6$, A, m, n and p are defined as before.

Further particularly preferred are those compounds of formula (Ia), wherein
$R^1$ is hydrogen, alkyl, formyl or hydroxyalkyl;
$R^2$ is hydrogen, alkyl, alkenyl, alkynyl or cyano;
and $R^3$, $R^4$, $R^5$, $R^6$, A, m, n and p are defined as before.

Further preferred are the compounds of formula (I), wherein the bond between the carbon atoms $C^a$ and $C^b$ is a carbon carbon double bond and $R^3$ and $R^4$ are absent. Those compounds are of formula

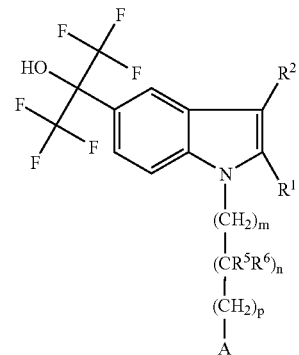

(Ib)

wherein $R^1$, $R^2$, $R^3$, $R^4$, $R^5$, $R^6$, A, m, n and p are defined as before.

Further preferred are the compounds of formula (I), wherein A is phenyl, oxazolyl, quinolinyl, thiazolyl, naphthalenyl, benzothiophenyl, isoxazolyl, quinolinyl, pyridinyl, 2H-pyrazol-3-yl or isooxazolyl, wherein phenyl, oxazolyl, quinolinyl, thiazolyl, naphthalenyl, benzothiophenyl, isoxazolyl, quinolinyl, pyridinyl, 2H-pyrazol-3-yl and isooxazolyl are optionally substituted with one to three substituents independently selected from alkyl, halogen, amino, hydroxyalkyl, aryl, aryloxy, alkoxy, arylalkyl, alkoxycarbonylamino, aminocarbonyloxy, carboxy, alkoxycarbonyl, alkoxycarbonylalkyl, aminoalkyl, trifluoromethyl, arylalkylaminocarbonyl, alkoxycarbonylalkylaminocarbonyl, indolylalkylaminocarbonyl, morpholinylcarbonyl, aminocarbonyl, aminocarbonylalkyl, aminocarbonylalkoxy, alkoxycarbonylalkoxy, pyridinylalkylaminocarbonyl, alkyloxycarbonylalkylaryl, alkyloxycarbonylalkoxyaryl, carboxyalkylaryl, carboxyalkoxyaryl, aminocarbonylalkylaryl, aminocarbonylalkoxyaryl, aminocarbonylamino, aminocarbonyloxy, aminocarbonyloxyaryl, carboxyalkyl, carboxyalkoxy, cycloalkylaminocarbonyl, morpholinylcarbonyloxyaryl, morpholinylcarbonylaryl, arylalkoxyaryl, aminocarbonylaryl, pyrrolidinylcarbonyloxyaryl, pyrrolidinylcarbonylaryl, piperidinylcarbonylaryl and piperidinylcarbonyloxyaryl.

Particularly preferred are those compounds of formula (I), wherein A is phenyl, oxazol-2-yl or oxazol-4-yl, wherein phenyl, oxazol-2-yl and oxazol-4-yl are optionally substituted with one to three substituents independently selected from alkyl, tolyl, ethyl-phenyl, trifluoromethyl-phenyl, fluoro-phenyl, chloro-phenyl, carboxymethoxy-phenyl, aminocarbonylmethoxy-phenyl, carboxy-phenyl, hydroxyl-phenyl, hydroxymethyl-phenyl and aminocarbonyl-phenyl. Further particularly preferred are those compounds of formula (I), wherein A is phenyl.

Other preferred compounds of formula (I) as defind above are those, wherein A is oxazolyl which is substituted with a first substituent which is alkyl and a second substituent which is phenyl or pyridinyl, which phenyl is substituted with hydroxyalkyl. Preferably, A is 2-[4-(1-hydroxy-ethyl)-phenyl]-5-methyl-oxazol-4-ylmethyl, 2-[3-(1-hydroxy-ethyl)-phenyl]-5-methyl-oxazol-4-ylmethyl or 5-methyl-2-pyridin-3-yl-oxazol-4-ylmethyl.

Examples of preferred compounds of formula (I) are those selected from the group consisting of:

1,1,1,3,3,3-Hexafluoro-2-[2-methyl-1-(5-methyl-2-m-tolyl-oxazol-4-ylmethyl)-1H-indol-5-yl]-propan-2-ol;

2-(1-Benzyl-3-chloro-2-methyl-1H-indol-5-yl)-1,1,1,3,3,3-hexafluoro-propan-2-ol;

2-{1-[2-(4-Ethyl-phenyl) -5-methyl-oxazol-4-ylmethyl]-2-methyl-1H-indol-5-yl}-1,1,1,3,3,3-hexafluoro-propan-2-ol;

1,1,1,3,3,3-Hexafluoro-2-{2-methyl-1-[5-methyl-2-(3-trifluoromethyl-phenyl)-oxazol-4-ylmethyl]-1H-indol-5-yl}-propan-2-ol;

2-(1-Benzyl-3-fluoro-2-methyl-1H-indol-5-yl)-1,1,1,3,3,3-hexafluoro-propan-2-ol;

1,1,1,3,3,3-Hexafluoro-2-{1-[2-(2-fluoro-phenyl)-5-methyl-oxazol-4-ylmethyl]-2-methyl-1H-indol-5-yl}-propan-2-ol;

1,1,1,3,3,3-Hexafluoro-2-[2-methyl-1-(3-morpholin-4-ylmethyl-benzyl)-1H-indol-5-yl]-propan-2-ol;

3-[2-Methyl-5-(2,2,2-trifluoro-1-hydroxy-1-trifluoromethyl-ethyl)-indol-1-ylmethyl]-benzoic acid methyl ester;

2-[1-(3-Dimethylaminomethyl-benzyl)-2-methyl-1H-indol-5-yl]-1,1,1,3,3,3-hexafluoro-propan-2-ol;

1,1,1,3,3,3-Hexafluoro-2-{1-[2-(4-fluoro-3-methyl-phenyl)-5-methyl-oxazol-4-ylmethyl]-2-methyl-1H-indol-5-yl}-propan-2-ol;

1,1,1,3,3,3-Hexafluoro-2-[2-methyl-1-(2-trifluoromethyl-quinolin-6-ylmethyl)-1H-indol-5-yl]-propan-2-ol;

2-{1-[2-(3-Chloro-phenyl)-5-methyl-oxazol-4-ylmethyl]-2-methyl-1H-indol-5-yl}-1,1,1,3,3,3-hexafluoro-propan-2-ol;

2-{1-[2-(4-Chloro-phenyl)-5-methyl-oxazol-4-ylmethyl]-2-methyl-1H-indol-5-yl}-1,1,1,3,3,3-hexafluoro-propan-2-ol;

1,1,1,3,3,3-Hexafluoro-2-(2-methyl-1-quinolin-2-ylmethyl-1H-indol-5-yl)-propan-2-ol;

1,1,1,3,3,3-Hexafluoro-2-{2-methyl-1-[5-methyl-2-(4-trifluoromethyl-phenyl)-oxazol-4-ylmethyl]-1H-indol-5-yl}-propan-2-ol;

2-(1-Benzyl-1H-indol-5-yl)-1,1,1,3,3,3-hexafluoro-propan-2-ol;

1,1,1,3,3,3-Hexafluoro-2-(2-methyl-1-phenethyl-1H-indol-5-yl)-propan-2-ol;

1,1,1,3,3,3-Hexafluoro-2-[2-methyl-1-(5-methyl-2-phenyl-oxazol-4-ylmethyl)-1H-indol-5-yl]-propan-2-ol;

2-(1-Benzyl-2,3-dichloro-1H-indol-5-yl)-1,1,1,3,3,3-hexafluoro-propan-2-ol;

2-{1-[2-(4-tert-Butyl-phenyl)-5-methyl-oxazol-4-ylmethyl]-2-methyl-1H-indol-5-yl}-1,1,1,3,3,3-hexafluoro-propan-2-ol;

2-{1-[2-(4-Chloro-phenyl)-5-methyl-thiazol-4-ylmethyl]-2-methyl-1H-indol-5-yl}-1,1,1,3,3,3-hexafluoro-propan-2-ol;

2-(1-Benzyl-2,3-diiodo-1H-indol-5-yl)-1,1,1,3,3,3-hexafluoro-propan-2-ol;

1-Benzyl-5-(2,2,2-trifluoro-1-hydroxy-1-trifluoromethyl-ethyl)-1H-indole-2-carbaldehyde;

2-(1-Biphenyl-3-ylmethyl-2-methyl-1H-indol-5-yl)-1,1,1,3,3,3-hexafluoro-propan-2-ol;

1,1,1,3,3,3-Hexafluoro-2-(2-methyl-1-naphthalen-1-ylmethyl-1H-indol-5-yl)-propan-2-ol;

2-(1-Benzyl-3-iodo-1H-indol-5-yl)-1,1,1,3,3,3-hexafluoro-propan-2-ol;

N-Benzyl-N-methyl-3-[2-methyl-5-(2,2,2-trifluoro-1-hydroxy-1-trifluoromethyl-ethyl)-indol-1-ylmethyl]-benzamide;

4-[2-Methyl-5-(2,2,2-trifluoro-1-hydroxy-1-trifluoromethyl-ethyl)-indol-1-ylmethyl]-benzoic acid methyl ester;

N-Methyl-3-[2-methyl-5-(2,2,2-trifluoro-1-hydroxy-1-trifluoromethyl-ethyl)-indol-1-ylmethyl]-N-phenethyl-benzamide;

(Methyl-{3-[2-methyl-5-(2,2,2-trifluoro-1-hydroxy-1-trifluoromethyl-ethyl)-indol-1-ylmethyl]-benzoyl}-amino)-acetic acid ethyl ester;

3-[2-Methyl-5-(2,2,2-trifluoro-1-hydroxy-1-trifluoromethyl-ethyl)-indol-1-ylmethyl]-benzoic acid;

N-[2-(1H-Indol-3-yl)-ethyl]-N-methyl-3-[2-methyl-5-(2,2,2-trifluoro-1-hydroxy-1-trifluoromethyl-ethyl)-indol-1-ylmethyl]-benzamide;

{3-[2-Methyl-5-(2,2,2-trifluoro-1-hydroxy-1-trifluoromethyl-ethyl)-indol-1-ylmethyl]-phenyl}-morpholin-4-yl-methanone;

N,N-Dimethyl-3-[2-methyl-5-(2,2,2-trifluoro-1-hydroxy-1-trifluoromethyl-ethyl)-indol-1-ylmethyl]-benzamide;

N-Methyl-3-[2-methyl-5-(2,2,2-trifluoro-1-hydroxy-1-trifluoromethyl-ethyl)-indol-1-ylmethyl]-N-(2-pyridin-2-yl-ethyl)-benzamide;

N-Methyl-3-[2-methyl-5-(2,2,2-trifluoro-1-hydroxy-1-trifluoromethyl-ethyl)-indol-1-ylmethyl]-N-pyridin-2-ylmethyl-benzamide;

2-[1-Benzyl-2-(1-hydroxy-ethyl)-1H-indol-5-yl]-1,1,1,3,3,3-hexafluoro-propan-2-ol;

1-[1-Benzyl-5-(2,2,2-trifluoro-1-hydroxy-1-trifluoromethyl-ethyl)-1H-indol-2-yl]-propan-1-ol;

1,1,1,3,3,3-Hexafluoro-2-{1-[2-(4-isopropoxy-phenyl)-5-methyl-oxazol-4-ylmethyl]-2-methyl-1H-indol-5-yl}-propan-2-ol;

1,1,1,3,3,3-Hexafluoro-2-[1-(2-hydroxy-1-phenyl-ethyl)-2-methyl-1H-indol-5-yl]-propan-2-ol;

2-(1-Benzyl-2-hydroxymethyl-1H-indol-5-yl)-1,1,1,3,3,3-hexafluoro-propan-2-ol;

N-Cyclohexyl-N-methyl-3-[2-methyl-5-(2,2,2-trifluoro-1-hydroxy-1-trifluoromethyl-ethyl)-indol-1-ylmethyl]-benzamide;

2-[1-(5-Chloro-benzo[b]thiophen-3-ylmethyl)-2-methyl-2,3-dihydro-1H-indol-5-yl]-1,1,1,3,3,3-hexafluoro-propan-2-ol;

1,1,1,3,3,3-Hexafluoro-2-[2-methyl-1-(5-methyl-3-phenyl-isoxazol-4-ylmethyl)-2,3-dihydro-1H-indol-5-yl]-propan-2-ol;

2-(2-Chloro-phenyl)-4-[2-methyl-5-(2,2,2-trifluoro-1-hydroxy-1-trifluoromethyl-ethyl)-2,3-dihydro-indol-1-ylmethyl]-oxazole-5-carboxylic-acid methyl ester;

1,1,1,3,3,3-Hexafluoro-2-[2-methyl-1-(5-methyl-2-o-tolyl-oxazol-4-ylmethyl)-2,3-dihydro-1H-indol-5-yl]-propan-2-ol;

1,1,1,3,3,3-Hexafluoro-2-[2-methyl-1-(5-methyl-2-m-tolyl-oxazol-4-ylmethyl)-2,3-dihydro-1H-indol-5-yl]-propan-2-ol;

2-(1-Benzyl-2-methyl-2,3-dihydro-1H-indol-5-yl)-1,1,1,3,3,3-hexafluoro-propan-2-ol;

2-{1-[2-(4-Ethyl-phenyl)-5-methyl-oxazol-4-ylmethyl]-2-methyl-2,3-dihydro-1H-indol-5-yl}-1,1,1,3,3,3-hexafluoro-propan-2-ol;

1,1,1,3,3,3-Hexafluoro-2-[1-(3-hydroxymethyl-benzyl)-2-methyl-2,3-dihydro-1H-indol-5-yl]-propan-2-ol;

3-[2-Methyl-5-(2,2,2-trifluoro-1-hydroxy-1-trifluoromethyl-ethyl)-2,3-dihydro-indol-1-ylmethyl]-benzoic acid methyl ester;

1,1,1,3,3,3-Hexafluoro-2-{1-[2-(2-fluoro-phenyl)-5-methyl-oxazol-4-ylmethyl]-2-methyl-2,3-dihydro-1H-indol-5-yl}-propan-2-ol;

2-{1-[2-(3-Chloro-phenyl)-5-methyl-oxazol-4-ylmethyl]-2-methyl-2,3-dihydro-1H-indol-5-yl}-1,1,1,3,3,3-hexafluoro-propan-2-ol;

1,1,1,3,3,3-Hexafluoro-2-{1-[2-(4-fluoro-3-methyl-phenyl)-5-methyl-oxazol-4-ylmethyl]-2-methyl-2,3-dihydro-1H-indol-5-yl}-propan-2-ol;

1,1,1,3,3,3-Hexafluoro-2-(2-methyl-1-phenethyl-2,3-dihydro-1H-indol-5-yl)-propan-2-ol;

1,1,1,3,3,3-Hexafluoro-2-{2-methyl-1-[5-methyl-2-(3-trifluoromethyl-phenyl)-oxazol-4-ylmethyl]-2,3-dihydro-1H-indol-5-yl}-propan-2-ol;

1,1,1,3,3,3-Hexafluoro-2-[2-methyl-1-(5-methyl-2-phenyl-oxazol-4-ylmethyl)-2,3-dihydro-1H-indol-5-yl]-propan-2-ol;

1,1,1,3,3,3-Hexafluoro-2-[2-methyl-1-(2-trifluoromethyl-quinolin-6-ylmethyl)-2,3-dihydro-1H-indol-5-yl]-propan-2-ol;

1,1,1,3,3,3-Hexafluoro-2-{2-methyl-1-[5-methyl-2-(4-trifluoromethyl-phenyl)-oxazol-4-ylmethyl]-2,3-dihydro-1H-indol-5-yl}-propan-2-ol;

1,1,1,3,3,3-Hexafluoro-2-(2-methyl-1-naphthalen-1-ylmethyl-2,3-dihydro-1H-indol-5-yl)-propan-2-ol;

[2-Methyl-5-(2,2,2-trifluoro-1-hydroxy-1-trifluoromethyl-ethyl)-2,3-dihydro-indol-1-yl]-phenyl-acetic acid methyl ester;

2-{1-[2-(4-Chloro-phenyl)-5-methyl-oxazol-4-ylmethyl]-2-methyl-2,3-dihydro-1H-indol-5-yl}-1,1,1,3,3,3-hexafluoro-propan-2-ol;

1,1,1,3,3,3-Hexafluoro-2-(2-methyl-1-quinolin-2-ylmethyl-2,3-dihydro-1H-indol-5-yl)-propan-2-ol;

2-(1-Biphenyl-3-ylmethyl-2-methyl-2,3-dihydro-1H-indol-5-yl)-1,1,1,3,3,3-hexafluoro-propan-2-ol;

1,1,1,3,3,3-Hexafluoro-2-{2-methyl-1-[4-(4-trifluoromethyl-phenoxy)-benzyl]-2,3-dihydro-1H-indol-5-yl}-propan-2-ol;

2-{1-[2-(4-tert-Butyl-phenyl)-5-methyl-oxazol-4-ylmethyl]-2-methyl-2,3-dihydro-1H-indol-5-yl}-1,1,1,3,3,3-hexafluoro-propan-2-ol;

2-(1-Benzhydryl-2-methyl-2,3-dihydro-1H-indol-5-yl)-1,1,1,3,3,3-hexafluoro-propan-2-ol;

3-[2-Methyl-5-(2,2,2-trifluoro-1-hydroxy-1-trifluoromethyl-ethyl)-2,3-dihydro-indol-1-ylmethyl]-benzoic acid;

4-[2-Methyl-5-(2,2,2-trifluoro-1-hydroxy-1-trifluoromethyl-ethyl)-2,3-dihydro-indol-1-ylmethyl]-benzoic acid methyl ester;

1,1,1,3,3,3-Hexafluoro-2-[1-(2-hydroxy-1-phenyl-ethyl)-2-methyl-2,3-dihydro-1H-indol-5-yl]-propan-2-ol;

2-{1-[2-(4-Chloro-phenyl)-5-methyl-thiazol-4-ylmethyl]-2-methyl-2,3-dihydro-1H-indol-5-yl}-1,1,1,3,3,3-hexafluoro-propan-2-ol;

1,1,1,3,3,3-Hexafluoro-2-{1-[3-(4-fluoro-phenoxy)-benzyl]-2-methyl-2,3-dihydro-1H-indol-5-yl}-propan-2-ol;

1,1,1,3,3,3-Hexafluoro-2-{1-[2-(4-isopropoxy-phenyl)-5-methyl-oxazol-4-ylmethyl]-2-methyl-2,3-dihydro-1H-indol-5-yl}-propan-2-ol;

1,1,1,3,3,3-Hexafluoro-2-{2-methyl-1-[2-methyl-6-(4-trifluoromethyl-phenyl)-pyridin-3-ylmethyl]-2,3-dihydro-1H-indol-5-yl}-propan-2-ol;

2-{1-[2-(2,5-Diphenyl-oxazol-4-yl)-ethyl]-2-methyl-2,3-dihydro-1H-indol-5-yl}-1,1,1,3,3,3-hexafluoro-propan-2-ol;

1,1,1,3,3,3-Hexafluoro-2-{1-[2-(4-isopropyl-phenyl)-5-methyl-oxazol-4-ylmethyl]-2-methyl-2,3-dihydro-1H-indol-5-yl}-propan-2-ol;

1,1,1,3,3,3-Hexafluoro-2-{1-[2-(2-methoxy-phenyl)-5-methyl-oxazol-4-ylmethyl]-2-methyl-2,3-dihydro-1H-indol-5-yl}-propan-2-ol;

1,1,1,3,3,3-Hexafluoro-2-{2-methyl-1-[5-methyl-2-(2-trifluoromethyl-phenyl)-oxazol-4-ylmethyl]-2,3-dihydro-1H-indol-5-yl}-propan-2-ol;

2-{1-[2-(4-Benzyloxy-phenyl)-5-methyl-oxazol-4-ylmethyl]-2-methyl-2,3-dihydro-1H-indol-5-yl}-1,1,1,3,3,3-hexafluoro-propan-2-ol;

2-(1-Benzyl-2-methyl-1H-indol-5-yl)-1,1,1,3,3,3-hexafluoro-propan-2-ol;

1,1,1,3,3,3-Hexafluoro-2-{2-methyl-1-[2-methyl-5-(4-trifluoromethyl-phenyl)-2H-pyrazol-3-ylmethyl]-2,3-dihydro-1H-indol-5-yl}-propan-2-ol;

2-{1-[2-Ethyl-5-(4-trifluoromethyl-phenyl)-2H-pyrazol-3-ylmethyl]-2-methyl-2,3-dihydro-1H-indol-5-yl}-1,1,1,3,3,3-hexafluoro-propan-2-ol;

(4-{5-Methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetic acid methyl ester;

(4-{5-Methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetic acid;

1,1,1,3,3,3-Hexafluoro-2-{2-methyl-1-[2-(2-methyl-5-phenyl-oxazol-4-yl)-ethyl]-2,3-dihydro-1H-indol-5-yl}-propan-2-ol;

1,1,1,3,3,3-Hexafluoro-2-{2-methyl-1-[4-methyl-2-(4-trifluoromethyl-phenyl)-oxazol-5-ylmethyl]-2,3-dihydro-1H-indol-5-yl}-propan-2-ol;

N,N-Dimethyl-2-(4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetamide;

2-{1-[2-(3-Benzyloxy-phenyl)-5-methyl-oxazol-4-ylmethyl]-2-methyl-2,3-dihydro-1H-indol-5-yl}-1,1,1,3,3,3-hexafluoro-propan-2-ol;

4-{5-Methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester;

3-{5-Methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester;

3-{5-Methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid;

4-{5-Methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid;

3-{4-[2-Methyl-5-(2,2,2-trifluoro-1-hydroxy-1-trifluoromethyl-ethyl)-2,3-dihydro-indol-1-ylmethyl]-oxazol-2-yl}-benzoic acid methyl ester;

2-{1-[2-(2,5-Diphenyl-oxazol-4-yl)-ethyl]-2-methyl-1H-indol-5-yl}-1,1,1,3,3,3-hexafluoro-propan-2-ol;

1,1,1,3,3,3-Hexafluoro-2-{1-[2-(4-isopropyl-phenyl)-5-methyl-oxazol-4-ylmethyl]-2-methyl-1H-indol-5-yl}-propan-2-ol;

1,1,1,3,3,3-Hexafluoro-2-{1-[2-(2-methoxy-phenyl)-5-methyl-oxazol-4-ylmethyl]-2-methyl-1H-indol-5-yl}-propan-2-ol;

1,1,1,3,3,3-Hexafluoro-2-{2-methyl-1-[5-methyl-2-(2-trifluoromethyl-phenyl)-oxazol-4-ylmethyl]-1H-indol-5-yl}-propan-2-ol;

2-{1-[2-(4-Benzyloxy-phenyl)-5-methyl-oxazol-4-ylmethyl]-2-methyl-1H-indol-5-yl}-1,1,1,3,3,3-hexafluoro-propan-2-ol;

4-{5-Methyl-4-[2-methyl-5-(2,2,2-trifluoro-1-hydroxy-1-trifluoromethyl-ethyl)-indol-1-ylmethyl]-oxazol-2-yl}-phenol;

Dimethyl-carbamic acid 4-{5-methyl-4-[2-methyl-5-(2,2,2-trifluoro-1-hydroxy-1-trifluoromethyl-ethyl)-indol-1-ylmethyl]-oxazol-2-yl}-phenyl ester;

1,1,1,3,3,3-Hexafluoro-2-{2-methyl-1-[2-(5-methyl-2-phenyl-oxazol-4-yl)-ethyl]-1H-indol-5-yl}-propan-2-ol;

1,1,1,3,3,3-Hexafluoro-2-{2-methyl-1-[4-methyl-2-(4-trifluoromethyl-phenyl)-oxazol-5-ylmethyl]-1H-indol-5-yl}-propan-2-ol;

2-{1-[2-Ethyl-5-(4-trifluoromethyl-phenyl)-2H-pyrazol-3-ylmethyl]-2-methyl-1H-indol-5-yl}-1,1,1,3,3,3-hexafluoro-propan-2-ol;

1,1,1,3,3,3-Hexafluoro-2-{2-methyl-1-[2-methyl-5-(4-trifluoromethyl-phenyl)-2H-pyrazol-3-ylmethyl]-1H-indol-5-yl}-propan-2-ol;

(4-{5-Methyl-4-[2-methyl-5-(2,2,2-trifluoro-1-hydroxy-1-trifluoromethyl-ethyl)-indol-1-ylmethyl]-oxazol-2-yl}-phenoxy)-acetic acid methyl ester;

(4-{5-Methyl-4-[2-methyl-5-(2,2,2-trifluoro-1-hydroxy-1-trifluoromethyl-ethyl)-indol-1-ylmethyl]-oxazol-2-yl}-phenoxy)-acetic acid;

2-{3-Chloro-1-[2-(3-chloro-phenyl)-5-methyl-oxazol-4-ylmethyl]-2-methyl-1H-indol-5-yl}-1,1,1,3,3,3-hexafluoro-propan-2-ol;

Pyrrolidine-1-carboxylic acid 4-{5-methyl-4-[2-methyl-5-(2,2,2-trifluoro-1-hydroxy-1-trifluoromethyl-ethyl)-indol-1-ylmethyl]-oxazol-2-yl}-phenyl ester;

Morpholine-4-carboxylic acid 4-{5-methyl-4-[2-methyl-5-(2,2,2-trifluoro-1-hydroxy-1-trifluoromethyl-ethyl)-indol-1-ylmethyl]-oxazol-2-yl}-phenyl ester; 2-(2-Chloro-phenyl)-4-[2-methyl-5-(2,2,2-trifluoro-1-hydroxy-1-trifluoromethyl-ethyl)    -indol-1-ylmethyl]-oxazole-5-carboxylic acid;

2-{1-[2-(2-Chloro-phenyl)-5-hydroxymethyl-oxazol-4-ylmethyl]-2-methyl-1H-indol-5-yl}-1,1,1,3,3,3-hexafluoro-propan-2-ol;

N,N-Dimethyl-2-(4-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetamide;

2-{1-[2-(3-Benzyloxy-phenyl)-5-methyl-oxazol-4-ylmethyl]-2-methyl-1H-indol-5-yl}-1,1,1,3,3,3-hexafluoro-propan-2-ol;

3-{5-Methyl-4-[2-methyl-5-(2,2,2-trifluoro-1-hydroxy-1-trifluoromethyl-ethyl)-indol-1-ylmethyl]-oxazol-2-yl}-phenol;

Morpholine-4-carboxylic acid 3-{5-methyl-4-[2-methyl-5-(2,2,2-trifluoro-1-hydroxy-1-trifluoromethyl-ethyl)-indol-1-ylmethyl]-oxazol-2-yl}-phenyl ester;

Dimethyl-carbamic acid 3-{5-methyl-4-[2-methyl-5-(2,2,2-trifluoro-1-hydroxy-1-trifluoromethyl-ethyl)-indol-1-ylmethyl]-oxazol-2-yl}-phenyl ester;

Pyrrolidine-1-carboxylic acid 3-{5-methyl-4-[2-methyl-5-(2,2,2-trifluoro-1-hydroxy-1-trifluoromethyl-ethyl)-indol-1-ylmethyl]-oxazol-2-yl}-phenyl ester;

(3-{5-Methyl-4-[2-methyl-5-(2,2,2-trifluoro-1-hydroxy-1-trifluoromethyl-ethyl)-indol-1-ylmethyl]-oxazol-2-yl}-phenoxy)-acetic acid methyl ester;

3-{5-Methyl-4-[2-methyl-5-(2,2,2-trifluoro-1-hydroxy-1-trifluoromethyl-ethyl)-indol-1-ylmethyl]-oxazol-2-yl}-benzoic acid methyl ester;

4-{5-Methyl-4-[2-methyl-5-(2,2,2-trifluoro-1-hydroxy-1-trifluoromethyl-ethyl)-indol-1-ylmethyl]-oxazol-2-yl}-benzoic acid methyl ester;

3-{5-Methyl-4-[2-methyl-5-(2,2,2-trifluoro-1-hydroxy-1-trifluoromethyl-ethyl)-indol-1-ylmethyl]-oxazol-2-yl}-benzoic acid;

1,1,1,3,3,3-Hexafluoro-2-{1-[2-(3-hydroxymethyl-phenyl)-5-methyl-oxazol-4-ylmethyl]-2-methyl-1H-indol-5-yl}-propan-2-ol;

4-{5-Methyl-4-[2-methyl-5-(2,2,2-trifluoro-1-hydroxy-1-trifluoromethyl-ethyl)-indol-1-ylmethyl]-oxazol-2-yl}-benzoic acid;

N,N-Dimethyl-3-{5-methyl-4-[2-methyl-5-(2,2,2-trifluoro-1-hydroxy-1-trifluoromethyl-ethyl)-indol-1-ylmethyl]-oxazol-2-yl}-benzamide;

(3-{5-Methyl-4-[2-methyl-5-(2,2,2-trifluoro-1-hydroxy-1-trifluoromethyl-ethyl)-indol-1-ylmethyl]-oxazol-2-yl}-phenoxy)-acetic acid;

N,N-Dimethyl-4-{5-methyl-4-[2-methyl-5-(2,2,2-trifluoro-1-hydroxy-1-trifluoromethyl-ethyl)-indol-1-ylmethyl]-oxazol-2-yl}-benzamide;

1,1,1,3,3,3-Hexafluoro-2-{1-[2-(4-hydroxymethyl-phenyl)-5-methyl-oxazol-4-ylmethyl]-2-methyl-1H-indol-5-yl}-propan-2-ol;

2-[2,3-Dimethyl-1-(5-methyl-2-phenyl-oxazol-4-ylmethyl)-1H-indol-5-yl]-1,1,1,3,3,3-hexafluoro-propan-2-ol;

1,1,1,3,3,3-Hexafluoro-2-[2-methyl-1-(5-methyl-2-o-tolyl-oxazol-4-ylmethyl)-1H-indol-5-yl]-propan-2-ol;

2-(2-Chloro-phenyl)-4-[2-methyl-5-(2,2,2-trifluoro-1-hydroxy-1-trifluoromethyl-ethyl)    -indol-1-ylmethyl]-oxazole-5-carboxylic acid methyl ester;

1,1,1,3,3,3-Hexafluoro-2-[2-methyl-1-(5-methyl-3-phenyl-isoxazol-4-ylmethyl)-1H-indol-5-yl]-propan-2-ol;

1,1,1,3,3,3-Hexafluoro-2-{1-[3-(4-fluoro-phenoxy)-benzyl]-2-methyl-1H-indol-5-yl}-propan-2-ol;

1,1,1,3,3,3-Hexafluoro-2-(2-methyl-I —Naphthalen-2-ylmethyl-1H-indol-5-yl)-propan-2-ol;

1,1,1,3,3,3-hexafluoro-2-(2-methyl-1-naphthalen-2-ylmethyl-2,3-dihydro-1H-indol-5-yl)-propan-2-ol;

1,1,1,3,3,3-Hexafluoro-2-{2-methyl-1-[2-methyl-6-(4-trifluoromethyl-phenyl)-pyridin-3-ylmethyl]-1H-indol-5-yl}-propan-2-ol; and {3-[2-Methyl-5-(2,2,2-trifluoro-1-hydroxy-1-trifluoromethyl-ethyl)-indol-1-ylmethyl]-phenyl}-piperidin-1-yl-methanone.

Examples of particularly preferred compounds of formula (I) are those selected from the group consisting of:

1,1,1,3,3,3-Hexafluoro-2-[2-methyl-1-(5-methyl-2-m-tolyl-oxazol-4-ylmethyl)-1H-indol-5-yl]-propan-2-ol;

2-(1-Benzyl-3-chloro-2-methyl-1H-indol-5-yl)-1,1,1,3,3,3-hexafluoro-propan-2-ol;

1,1,1,3,3,3-Hexafluoro-2-{2-methyl-1-[5-methyl-2-(3-trifluoromethyl-phenyl)-oxazol-4-ylmethyl]-1H-indol-5-yl}-propan-2-ol;

1,1,1,3,3,3-Hexafluoro-2-{1-[2-(2-fluoro-phenyl)-5-methyl-oxazol-4-ylmethyl]-2-methyl-1H-indol-5-yl}-propan-2-ol;

2-{1-[2-(3-Chloro-phenyl)-5-methyl-oxazol-4-ylmethyl]-2-methyl-1H-indol-5-yl}-1,1,1,3,3,3-hexafluoro-propan-2-ol;

1,1,1,3,3,3-Hexafluoro-2-(2-methyl-1-phenethyl-1H-indol-5-yl)-propan-2-ol;

1,1,1,3,3,3-Hexafluoro-2-[2-methyl-1-(5-methyl-2-m-tolyl-oxazol-4-ylmethyl)-2,3-dihydro-1H-indol-5-yl]-propan-2-ol;

2-{1-[2-(4-Ethyl-phenyl)-5-methyl-oxazol-4-ylmethyl]-2-methyl-2,3-dihydro-1H-indol-5-yl}-1,1,1,3,3,3-hexafluoro-propan-2-ol;

2-{1-[2-(3-Chloro-phenyl)-5-methyl-oxazol-4-ylmethyl]-2-methyl-2,3-dihydro-1H-indol-5-yl}-1,1,1,3,3,3-hexafluoro-propan-2-ol;

1,1,1,3,3,3-Hexafluoro-2-(2-methyl-1-phenethyl-2,3-dihydro-1H-indol-5-yl)-propan-2-ol;

1,1,1,3,3,3-Hexafluoro-2-{2-methyl-1-[5-methyl-2-(3-trifluoromethyl-phenyl)-oxazol-4-ylmethyl]-2,3-dihydro-1H-indol-5-yl}-propan-2-ol;

(4-{5-Methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetic acid;

N,N-Dimethyl-2-(4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetamide;

3-{5-Methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid;

4-{5-Methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid;

4-{5-Methyl-4-[2-methyl-5-(2,2,2-trifluoro-1-hydroxy-1-trifluoromethyl-ethyl)-indol-1-ylmethyl]-oxazol-2-yl}-phenol;

(4-{5-Methyl-4-[2-methyl-5-(2,2,2-trifluoro-1-hydroxy-1-trifluoromethyl-ethyl)-indol-1-ylmethyl]-oxazol-2-yl}-phenoxy)-acetic acid;

N,N-Dimethyl-2-(4-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetamide;

3-{5-Methyl-4-[2-methyl-5-(2,2,2-trifluoro-1-hydroxy-1-trifluoromethyl-ethyl)-indol-1-ylmethyl]-oxazol-2-yl}-phenol;

3-{5-Methyl-4-[2-methyl-5-(2,2,2-trifluoro-1-hydroxy-1-trifluoromethyl-ethyl)-indol-1-ylmethyl]-oxazol-2-yl}-benzoic acid;

1,1,1,3,3,3-Hexafluoro-2-{1-[2-(3-hydroxymethyl-phenyl)-5-methyl-oxazol-4-ylmethyl]-2-methyl-1H-indol-5-yl}-propan-2-ol;

4-{5-Methyl-4-[2-methyl-5-(2,2,2-trifluoro-1-hydroxy-1-trifluoromethyl-ethyl)-indol-1-ylmethyl]-oxazol-2-yl}-benzoic acid;

N,N-Dimethyl-3-{5-methyl-4-[2-methyl-5-(2,2,2-trifluoro-1-hydroxy-1-trifluoromethyl-ethyl)-indol-1-ylmethyl]-oxazol-2-yl}-benzamide;

(3-{5-Methyl-4-[2-methyl-5-(2,2,2-trifluoro-1-hydroxy-1-trifluoromethyl-ethyl)-indol-1-ylmethyl]-oxazol-2-yl}-phenoxy)-acetic acid;

N,N-Dimethyl-4-{5-methyl-4-[2-methyl-5-(2,2,2-trifluoro-1-hydroxy-1-trifluoromethyl-ethyl)-indol-1-ylmethyl]-oxazol-2-yl}-benzamide; and 1,1,1,3,3,3-Hexafluoro-2-{1-[2-(4-hydroxymethyl-phenyl)-5-methyl-oxazol-4-ylmethyl]-2-methyl-1H-indol-5-yl}-propan-2-ol.

Other preferred compounds according to formula (I) as defined above are those selected from the group consisting of:

Trans 1,1,1,3,3,3-Hexafluoro-2-[2-methyl-1-(5-methyl-2-styryl-oxazol-4-ylmethyl)-2,3-dihydro-1H-indol-5-yl]-propan-2-ol, 2-[1-(2-Benzyl-5-methyl-oxazol-4-ylmethyl)-2-methyl-2,3-dihydro-1H-indol-5-yl]-1,1,1,3,3,3-hexafluoro-propan-2-ol, 1,1,1,3,3,3-Hexafluoro-2-[2-methyl-1-(5-methyl-2-phenethyl-oxazol-4-ylmethyl)-2,3-dihydro-1H-indol-5-yl]-propan-2-ol, 4-{5-Methyl-4-[2-methyl-5-(2,2,2-trifluoro-1-hydroxy-1-trifluoromethyl-ethyl)-2,3-dihydro-indol-1-ylmethyl]-oxazol-2-yl}-phenol, 1,1,1,3,3,3-Hexafluoro-2-[2-methyl-1-(5-methyl-2-phenethyl-oxazol-4-ylmethyl)-1H-indol-5-yl]-propan-2-ol, 1,1,1,3,3,3-Hexafluoro-2-{1-[2-(3-hydroxymethyl-phenyl)-5-methyl-oxazol-4-ylmethyl]-2-methyl-2,3-dihydro-1H-indol-5-yl}-propan-2-ol, 1,1,1,3,3,3-Hexafluoro-2-{1-[2-(4-hydroxymethyl-phenyl)-5-methyl-oxazol-4-ylmethyl]-2-methyl-2,3-dihydro-1H-indol-5-yl}-propan-2-ol, 1,1,1,3,3,3-Hexafluoro-2-(1-{2-[4-(1-hydroxy-ethyl)-phenyl]-5-methyl-oxazol-4-ylmethyl}-2-methyl-1H-indol-5-yl)-propan-2-ol, 1,1,1,3,3,3-Hexafluoro-2-(1-{2-[3-(1-hydroxy-ethyl)-phenyl]-5-methyl-oxazol-4-ylmethyl}-2-methyl-1H-indol-5-yl)-propan-2-ol, (2R) 1,1,1,3,3,3-Hexafluoro-2-{2-methyl-1-[5-methyl-2-(3-trifluoromethyl-phenyl)-oxazol-4-ylmethyl]-2,3-dihydro-1H-indol-5-yl}-propan-2-ol, (2S) 1,1,1,3,3,3-Hexafluoro-2-{2-methyl-1-[5-methyl-2-(3-trifluoromethyl-phenyl)-oxazol-4-ylmethyl]-2,3-dihydro-1H-indol-5-yl}-propan-2-ol, and 1,1,1,3,3,3-Hexafluoro-2-[2-methyl-1-(5-methyl-2-pyridin-3-yl-oxazol-4-ylmethyl)-2,3-dihydro-1H-indol-5-yl]-propan-2-ol, and pharmaceutically acceptable salts and pharmaceutically acceptable esters thereof.

Other particularly preferred compounds according to formula (I) as defined above are those selected from the group consisting of:

1,1,1,3,3,3-Hexafluoro-2-(1-{2-[4-(1-hydroxy-ethyl)-phenyl]-5-methyl-oxazol-4-ylmethyl}-2-methyl-1H-indol-5-yl)-propan-2-ol, 1,1,1,3,3,3-Hexafluoro-2-(1-{2-[3-(1-hydroxy-ethyl)-phenyl]-5-methyl-oxazol-4-ylmethyl}-2-methyl-1H-indol-5-yl)-propan-2-ol, and 1,1,1,3,3,3-Hexafluoro-2-[2-methyl-1-(5-methyl-2-pyridin-3-yl-oxazol-4-ylmethyl)-2,3-dihydro-1H-indol-5-yl]-propan-2-ol, and pharmaceutically acceptable salts and pharmaceutically acceptable esters thereof.

The preparation of compounds of formula (I) of the present invention may be carried out in sequential or convergent synthetic routes. Syntheses of the invention are shown in the following schemes. The skills required for carrying out the reaction and purification of the resulting products are known to those in the art. The substituents and indices used in the following description of the processes have the significance given above unless indicated to the contrary.

One method to prepare compounds of formula (Ia), in which $R^1$ to $R^6$, m, n, p and A are as above, is illustrated in scheme 1.

An indoline 1 is converted to the hexafluoroisopropanol 2 by treatment with hexafluoroacetone sesquihydrate (step a). In an optional step b, 2 is O-protected (PG=protecting group) e.g. by treatment with a silylating agent such as TESCl in presence of a suitable base such as DBU. Both 2 and 3 can be N-alkylated to (Ia) and 4, respectively, by treatment with a compound "LG-$(CH_2)_m(CR^5R^6)_n$—$(CH_2)_p$-A" (wherein LG is a leaving group such as e.g. Cl, Br, I, MsO, TsO or TfO) in a solvent such as e.g. DMF at 50-180° C. (step c). Alternatively this N-alkylation may be carried out by reaction with an oxirane 5 (step d) optionally in the presence of a Lewis acid such as e.g. lithiumperchlorate or $ZnCl_2$ (in analogy to e.g.: Chini et al., J. Org. Chem., 1991, 56(20) 5939-5942; Duran Pachon et al., Tet. Lett., 2003, 44(32) 6025-6027), to give derivatives in which m=0, n=1, and $R^6$=$CH_2OH$. Both 2 and 3 may also be N-alkylated by treatment with ClOC$(CH_2)_{m-1}$$(CR^5R^6)_n$—$(CH_2)_p$-A in presence of a base or with HOOC$(CH_2)_{m-1}$$(CR^5R^6)_n$—$(CH_2)_p$-A in the presence e.g. EDCI and HOBT or other typical reagents used for the formation of amides from carboxylic acids and amines (step e). The resulting amide intermediate is reduced in step f (e.g. with $BH_3$) to 4/Ia. Alternatively, the $(CH_2)_m(CR^5R^6)_n$—$(CH_2)_p$-A-moiety can be introduced prior to the introduction of the hexafluoroisopropanolyl-group leading to 6, which upon treatment with hexafluoroacetone sesquihydrate is converted to (Ia). Indolines 4 may be deprotected to indolines (Ia) (e.g. desilylation in the presence of TBAF).

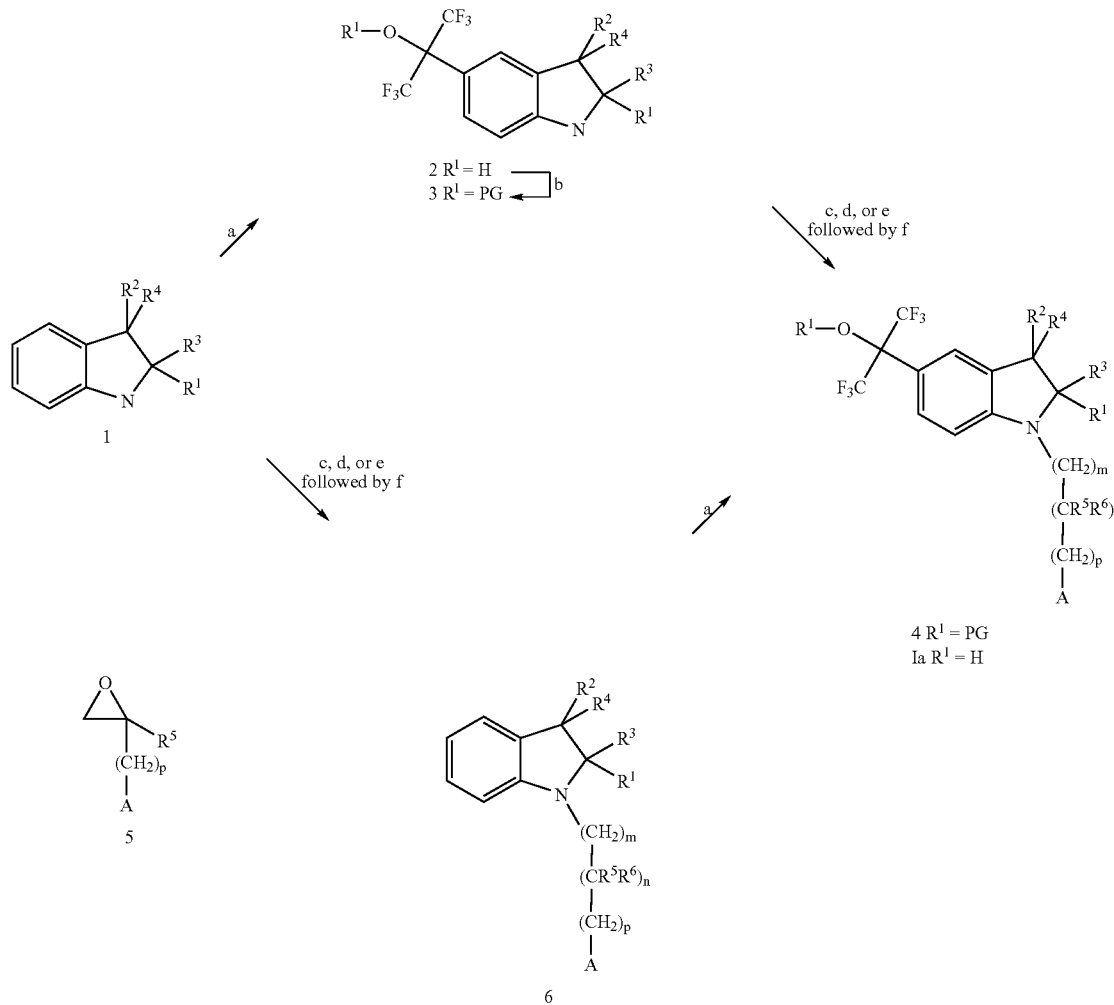

As shown in scheme 2 (step a), indolines 4 and (Ia), obtained according to scheme 1, in which both $R^3$ and $R^4$ are H, can be oxidized to the indole 7 and (Ib), respectively (e.g. by treatment with $MnO_2$ or DDQ).

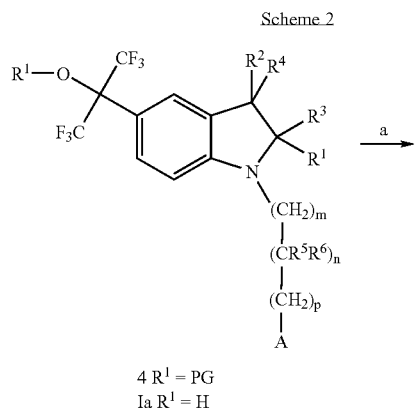

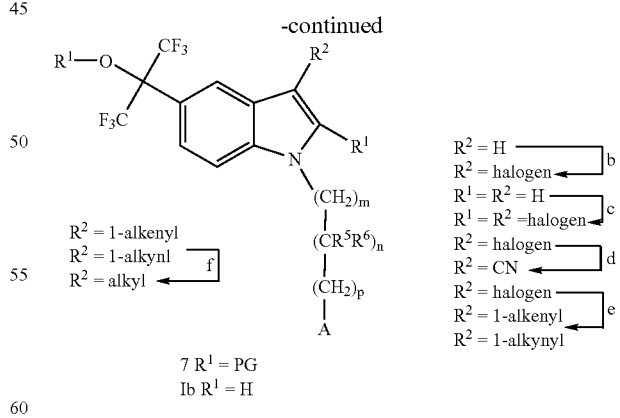

For indoles 7 or (Ib), in which either $R^1$ or $R^2$=H, this substituent may be converted to Cl, Br, I, or F, e.g. by treatment with 1-1.5 equivalents of a halogenating agent such as e.g. NCS, NBS, NIS, or N-fluoropyridinium-trifluoromethanesulfonate, respectively (step b). Indoles (Ib) or 7 with both $R^1$ and $R^2$=H, may be dihalogenated using 2-3 equivalents of the halogenating agent (step c). Indoles 7 and Ib with R²=Cl, Br or I may be converted to indoles 7 and Ib with R²=CN (step d) e.g. by Pd(II)-mediated coupling with CuCN (e.g. in analogy to Sundermeyer et al., Chemistry an European Journal, 2003, 9 (8), 1828-1836, or to indoles 7 and Ib in which R² is alkenyl or alkynyl (step e) e.g. by Heck/Stille or Sonogashira type couplings, respectively (e.g. in analogy to Brown et al., Tet. Lett., 2001, 2 (6), 983-985; Kanekiyo et al., Heterocycles, 2000, 53 (9), 1877-1880). Derivatives with R²=alkenyl or alkynyl may be hydrogenated in presence of e.g. Pd/C to the derivatives with R²=alkyl (step f). For R²=H, this substituent may be converted to a methyl substituent; usually this is done by treatment with 1-1.5 equivalents of DMF and POCl₃ followed by hydrogenolysis in presence of Pd/C of the resulting aldehyde or of the alcohol obtained by reduction (e.g. with LiAlH₄).

Indoles 7 with R¹=Cl, Br or I may be converted to derivatives with R¹=hydroxyalkyl (e.g. by metal-halogen exchange with e.g. an organolithium and subsequent treatment with paraformaldehyde, an aldehylde CHOalkyl or a dialkylketone), to derivatives with R¹=formyl (e.g. by metal-halogen exchange with e.g. an organolithium and subsequent treatment with a formylating agent such as e.g. DMF), or to derivatives with R¹=alkyl by treatment with an alkylating agent such as e.g. iodomethane after the metal-halogen exchange. Intermediates with R¹=COOH may be obtained by treating the indole with $CO_2$ after the metal-halogen exchange. Such carboxylic acids can be converted to the indole with R¹=CF₃ e.g. by treatment with SF4 gas.

Indoles 7 may be deprotected to indoles (Ib) (e.g. desilylation in the presence of TBAF).

Another method for the preparation of indoles (Ib) in which R¹, R², m, n, and o and A are defined as in claim I, but particularly suited for the preparation of indoles (Ib), in which R¹ is hydroxyalkyl, formyl or alkyl, is represented in scheme 3.

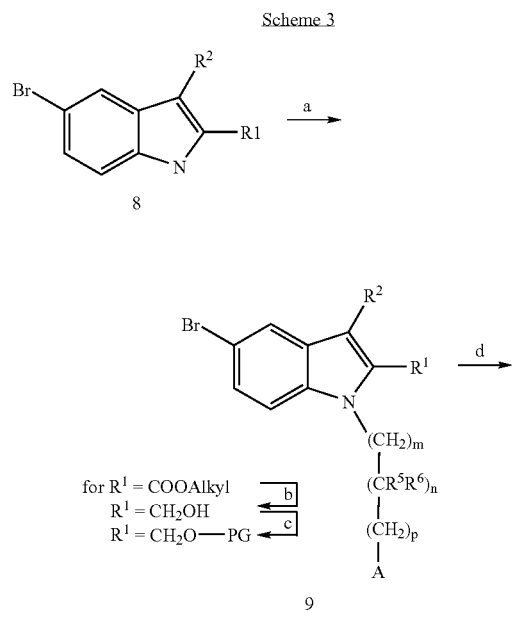

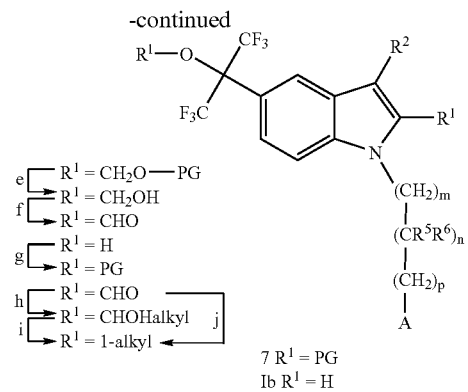

5-bromoindole 8 is N-alkylated by deprotonation with a sufficiently strong base (e.g. NaH) and subsequent treatment with a compound "LG-(CH₂)ₘ(CR⁵R⁶)ₙ—(CH₂)ₚ-A" (wherein LG is a leaving group such as e.g. Cl, Br, I, MsO, TsO or TfO) or an epoxide 5 (see scheme 1) to give 9 (step a). For R¹=COOalkyl, a reduction (e.g. with LiAlH₄) is carried out (step b) and the resulting alcohol is O-protected in step c (e.g. with TIPS-triflate in the presence of DIPEA). Metal halogen exchange with an alkyllithium or a alkylmagnesiumhalogenide (e.g. nBuLi, tertBuLi, EtMgBr) followed by treatment with hexafluoroacetone gas leads to the indolylhexafluoroisopropanol (Ib) (step d). For (Ib) with R¹=CH₂O—PG deprotection may be carried out in step e according to a standard procedure (e.g. desilylation in presence of TBAF) and the resulting alcohol may be oxidized (e.g. with MnO₂) to the formylindole (step f). In an optional step g the 2-formylindole may be O-protected (e.g. by treatment with TESCl in the presence of DBU). Treatment of the 2-formylindole with an alkylmagnesiumhalogenide or an alkyllithium leads to derivatives with R¹=1-hydroxyalkyl (step h). Deoxygenation e.g. by hydrogenolysis in presence of a catalyst such as Pd/C, or by treatment with a reducing agent such as e.g. BH₃.Me₂S or Et₃Si—H optionally in presence of an acid or Lewis acid such as e.g. TFA or BF₃.OEt₂ (e.g. in analogy to Pearlstein et al., Bioorg. and Med. Chem. Lett., 2003, 13, 1829-1835; Mewshaw et al., Bioorg. and Med. Chem. Lett., 2002, 12, 307-310; Sakagani et al., Synlett. 1996, 163-164) leads to derivatives with R¹=alkyl (step i). Alternatively derivatives with R¹=alkyl can be obtained from derivatives with R¹=1-hydroxyalkyl by 1,2-elimination promoted e.g. by treatment with a sulfonylating agent such as e.g. Tf₂O in presence of a base such as e.g. DIPEA and subsequent hydrogenation in presence of e.g. Pd/C, or from derivatives with R¹=CHO by hydrogenation in presence of e.g. Pd/C or by Wittig-type reaction with a phosphonium ylide alkylHC=PPh₃ (e.g. Maryanoff et al., Chem. Rev., 1989, 89, 863-927) and subsequent hydrogenation in presence of e.g. Pd/C.

Indoles 7 and (Ib) for which neither R¹ nor R² is a halogen can be converted to the corresponding indolines 4 and Ib with R³=R⁴=hydrogen e.g. by treatment with a reducing agent as e.g. NaBH₄, NaCNBH₃ or Et₃SiH most often in the presence of an acid such as e.g. TFA.

As mentioned before, indoles 7 may be deprotected to indoles (Ib) (e.g. desilylation in the presence of TBAF).

Another method to prepare indolines (Ia) in which R¹-R⁶, m, n, p and A are defined as in claim I but particularly suited to prepare derivatives in which at least one of R¹ and R³ is alkyl, R² is alkyl, alkenyl, alkynyl or cyano and R⁴ is hydroxy or alkoxy, is represented in scheme 4:

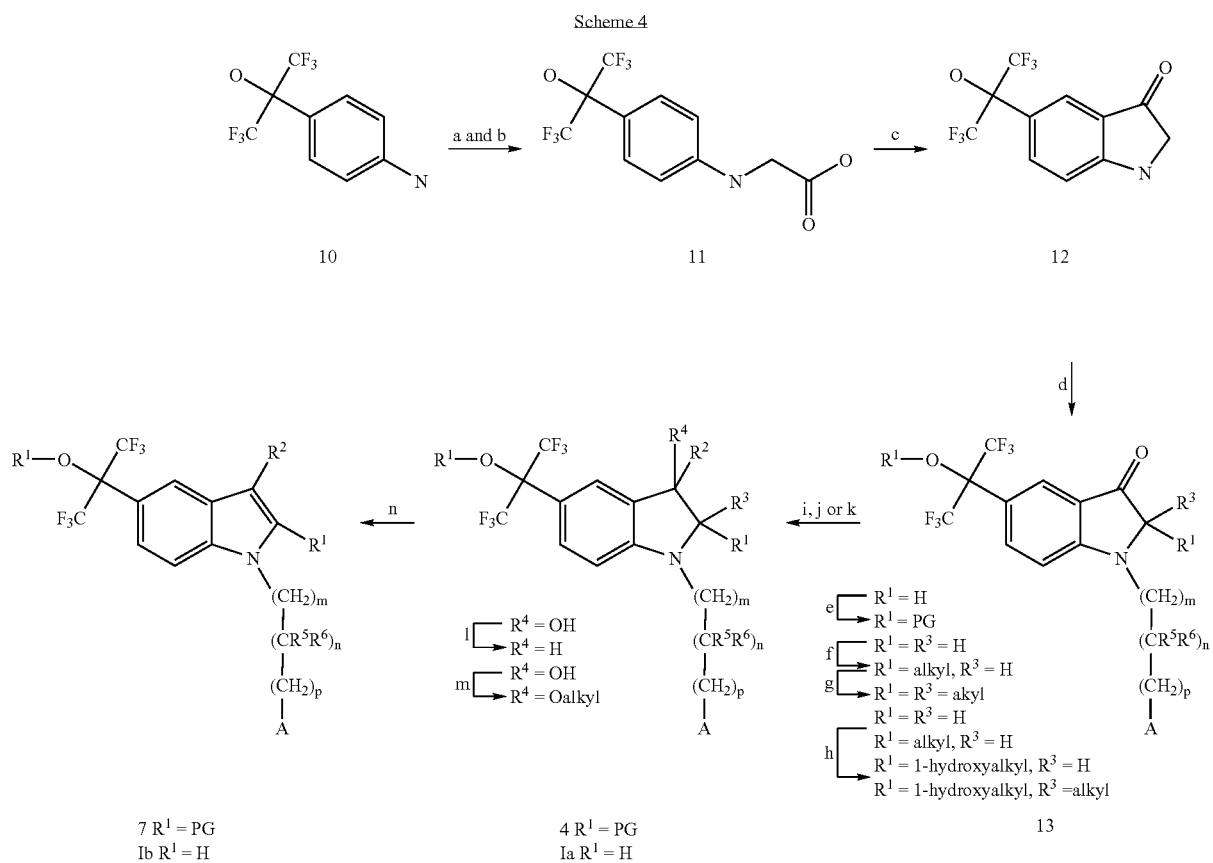

Scheme 4

Treatment of 4-(hexafluoro-2-hydroxyisopropyl)aniline 10 with bromo-acetic acid methyl ester followed by NaOH-mediated hydrolylsis of the ester moiety leads to the α-aminoacid 11 (steps a and b), which is cyclized in step c to the indoline-3-one 12 e.g. in the presence of TFAA and triphenylphosphineoxide (e.g. in analogy to Hendrickson et al., J. Org. Chem., 1989, 54, 1144-1149). N-alkylation (step d) to give 13 and O-protection (step e) is carried out as described in scheme 1. Deprotonation of 13 with a sufficiently strong base (e.g. LiHMDS) and treatment with an alkylating agent such as e.g. an alkyliodide leads to derivatives with $R^3$=alkyl and $R^1$=H (step f). Such a derivative may again be deprotonated and again be treated with an alkylating agent to give derivatives in which both $R^1$ and $R^3$ are alkyl (step g). If after the deprotonation paraformaldehyde, an aldehyde CHOalkyl or a dialkylketone is added instead of the alkylating agent, this leads to derivatives in which $R^1$ is hydroxyalkyl (step h). The hydroxy group on the $R^1$-substituent may optionally be protected (e.g. with TIPSOTf in the presence of DIPEA). Treatment of derivatives 13 with a reducing agent such as e.g. LiAlH$_4$ leads to compounds in which $R^4$ is hydroxy and $R^2$ is hydrogen (step i), whereas treatment of 13 with an $R^2$-magnesiumhalogenide or a $R^2$-lithium, wherein $R^2$=alkyl, alkenyl or alkynyl, leads to derivatives in which $R^4$ is hydroxy and $R^2$ is alkyl, alkenyl or alkynyl, respectively (step j). Derivatives in which $R^2$=cyano and $R^4$=hydroxy are obtained from 13 by treatment with a cyanide salt (e.g. KCN) or trimethylsilylcyanide in the presence of a Lewis acid such as e.g. Ti (O$^i$Pr)$_4$, Cu(OTf)$_2$, Zn(OTf)$_2$ (e.g. Saravan et al., Tet. Lett. 1998, 39 (22), 3823-3824) and subsequent treatment with aqueous HCl (step k). Deoxygenation of derivatives with $R^4$=hydroxy to derivatives with $R^4$=hydrogen may be carried out as described for step i of scheme 3. Alternatively $R^4$=hydroxy may be converted to $R^4$=alkoxy (step m) by base-mediated deprotonation (e.g. with LiHMDS) followed by treatment with an alkylating agent such as e.g. an alkyliodide. Derivatives for which $R^4$=hydroxy and $R^3$=hydrogen can be converted to the indole by 1,2-elimination promoted e.g. by treatment with a sulfonylating agent such as e.g. Tf$_2$O in the presence of a suitable base such as e.g. DIPEA (step n).

For indolines 4 with $R^1$=formyl and $R^3$=hydrogen, $R^3$ may be converted to alkyl by deprotonation with a suitable base (e.g. LiHMDS) and subsequent treatment with an alkylating agent such as e.g. an alkyliodide. The formyl group may subsequently be converted to hydroxyalkyl as described in scheme 3 for indoles 7. Deprotonation (e.g. with LiHMDS) and subsequent treatment with an alkylating agent can be used to convert indolines 4 with $R^2$=cyano and $R^4$=H to indolines 4 with $R^2$=cyano $R^4$=alkyl.

As mentioned before, indolines 4 may be deprotected to indolines (Ia) (e.g. desilylation in the presence of TBAF).

If 4, 7, (Ib) or (Ia) contain a functional group not compatible with one or several of the transformations of $R^1$-$R^4$ described above, this functional group may be suitably protected prior to the transformation(s) and deprotected again at a later stage of the synthesis. Such protections and deprotections are carried out according to standard literature procedures (as described e.g. in "Protective Groups in Organic Chemistry" by T. W. Greene and P. G. M. Wutts, 2$^{nd}$ Ed., 1991, Wiley N.Y.) and are commonly known to those of the art (e.g. O-silylation of a hydroxy group with TIPSOTf in presence of DIPEA and desilylation in the presence of TBAF).

The transformations of $R^1$-$R^4$ described above on 4, 7, (Ib) or (Ia) may alternatively be carried out on an indole with a suitable N-protecting group (such as e.g. trimethylsilylethyl or Boc) instead of the $(CH_2)_m(CR^5R^6)_n(CH_2)_p$A-moiety. The $(CH_2)_m(CR^5R^6)_n(CH_2)_p$A-moiety is introduced according to the procedures described in scheme 1 or scheme 3—preferably on the derivative with $R^1$=PG—once the N-protecting group has been removed. Introduction and removal of such N-protecting groups is carried out according to standard literature procedures (as described e.g. in "Protective Groups in Organic Chemistry" by T. W. Greene and P. G. M. Wutts, $2^{nd}$ Ed., 1991, Wiley N.Y.) and are commonly known to those of the art (e.g. N-Boc-protection with $Boc_2O$ in prescence of DIPEA and removal of the Boc-protecting group in presence of TFA).

A large number of compounds "LG-$(CH_2)_m(CR^5R^6)_n$—$(CH_2)_p$-A" with m, n, p, $R^5$, $R^6$, A, and LG defined as above are commercially available. If not they may be prepared from a related commercially available starting material such as e.g. an alcohol "HO-$(CH_2)_m(CR^5R^6)_n$—$(CH_2)_p$-A", or an ester "alkylOOC—$(CH_2)_{m-1}(CR^5R^6)_n$—$(CH_2)_p$-A" according to standard literature procedures commonly known to those of the art. If not commercially available, halogenides of the structure halogen-$(CHR^5)$-A, wherein halogen=Cl or Br, are prepared from $(CH_2R^5)$-A e.g. by treatment with NCS or NBS, respectively (e.g. Togo et al. Syn. Lett., 2003, 702-704). Oxiranes such as 5 may be prepared by treatment of 1-bis-functionalized ethenes $CH_2$=$C(R^5)$—$(CH_2)_p$-A with a commonly used epoxidizing agent such as mCPBA (e.g. Durley et al., J. Med. Chem., 2002, 45, 18, 3891-3904; Tian et al., Org. Lett., 3, 12, 2001, 1929-1932). Many of the halogen-$(CH_2)_m$ $(CR^5R^6)_n$—$(CH_2)_p$-A for which m=1, n, p=0, and A=heteroaryl may be prepared according to literature procedures (e.g. Binggeli et al. WO200292084 and WO97019311, Bouillot et al. WO2004006922; Morita et al., JP9095482; Cynkowski et al., J. Chem. Soc. Chem. Commun., 1995, 2335-2336; Kodama et al., U.S. Pat. No. 6,472,386; Faul et al., Heterocycles, 2001, 55 (4), 689-704.)

After preparation of 4, (Ia), 7, or (Ib) according to the synthetic descriptions above, functional groups present in A may optionally be further derivatized. Examples for typical transformations of such functional groups are summarized below:

Benzyloxy is typically transformed to hydroxy, hydroxy to alkoxycarbonylalkoxy, hydroxy (if attached to aryl or heteroaryl) to aryloxy, hydroxy to arylalkoxy, alkoxycarbonyl to hydroxymethyl, hydroxymethyl to formyl, alkoxycarbonyl to carboxy, carboxy to aminocarbonyl, aminocarbonyl to aminomethyl, amino to alkylcarbonylamino, amino to aminocarbonylamino, amino to alkoxycarbonylamino, wherein the just mentioned functional groups may be present alone or form part of a larger functional group. Procedures for these transformations are found in large number in literature and are commonly known to those of the art.

Formyl may typically be transformed to 1-hydroxyalkyl, by addition of an alkylmagnesium halogenide or an alkyllithium. By Zn(0) mediated addition of an α-bromoacetic acid ester (Reformatsky-reaction), the formyl group may be derivatized to a 2-(alkoxycarbonyl)-1-hydroxy ethyl group. If the 1-hydroxy(alkoxycarbonyl)ethyl is formed from a formyl group directly attached to an aryl or a heteroaryl, transformation to the alkoxycarbonylethyl-group may be carried out by deoxygenation, e.g by using one of the conditions mentioned in step i of scheme 3. Alternatively the transformation to the alkoxycarbonylethyl-group may be carried out by 1,2-elimination (e.g. promoted by treatment with $Tf_2O$ in presence of a base such as DIPEA) and subsequent hydrogenation of the alkene intermediate. Such an alkene intermediate may also be prepared directly starting from the formyl-derivative using Wittig-, Wittig-Horner-, Wadsworth-Emmons-, or Peterson-type olefinations. Procedures for such olefinations are found in large amount in literature and are commonly known to those of the art.

Cl-, Br- and I-substituents attached to aryl or heteroaryl may be converted to alkenyl, alkynyl, aryl, heterocyclyl, cyano, amino and carbonylamino, e.g. by Pd(II)-mediated coupling reactions; furthermore Cl-, Br and I-substituents may be transformed to hydroxyalkyl e.g. by metal-halogen exchange with e.g. an alkyllithium or a alkylmagnesiumhalogenide and subsequent reaction treatment with an aldehyde "CHOalkyl". A hydroxy group directly attached to an aryl or heteroaryl may be transformed to a TfO-substituent (e.g. by treatment with $Tf_2O$ in presence of a base such as e.g. DIPEA). The thereby obtained triflate may—in analogy to the Cl-, Br, and I-substituent—be used e.g. for Pd(II)-promoted coupling reactions leading to the replacement of the TfO-substituent by alkenyl, alkynyl, aryl, heterocyclyl, cyano, amino and carbonylamino (examples may e.g. be found in: Olofsson et al. J. Org. Chem., 1998, 65 (15), 5076-5079; Buchwald et al., J. Org. Chem., 2000, 65 (4), 1158-1174; Takagi et al., Chem. Lett., 1989, 11, 1957-58).

Prior to the derivatizations of the functional group on A, sensitive functional groups on 4, 7, (Ib) or (Ia) may be suitably protected (e.g. silylation of a hydroxy group) and deprotected again whenever desired. Similarly any of the derivatives 4 and 7 as described above may—whenever desired—be deprotected to (Ia) and (Ib), respectively. As mentioned before, protections and deprotections are carried out according to standard procedures (as described e.g. in "Protective Groups in Organic Chemistry" by T. W. Greene and P. G. M. Wutts, $2^{nd}$ Ed., 1991, Wiley N.Y.) commonly known to those of the art.

Indolines 1 and indoles 8, if not commercially available, may be prepared from commercially available indolines (such as e.g. indoline-2-carboxylic acid) indoline-2-ones, indoline-3-ones, indoles, anilines, phenylhydrazines, ketones or other related commercially available starting materials according to literature procedures (as described e.g. in: Advances in Heterocyclic Chemistry, Monograph Series by A. Katritzky (Editor); Comprehensive Heterocyclic Chemistry II, a review of Literature 1982-1995, Monograph Series by A. Katritzky (Editor); Indoles (best synthetic methods) by A. Katritky (Editor), Academic Press, London 1996).

The conversion of a compound of formula (I) into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The corresponding carboxylate salts can also be prepared from the compounds of formula (I) by treatment with physiologically compatible bases.

The conversion of compounds of formula (I) into pharmaceutically acceptable esters or amides can be carried out e.g. by treatment of suited amino or hydroxyl groups present in the molecules with an carboxylic acid such as acetic acid, with a condensating reagent such as benzotriazol-1-yloxytris (dimethylamino)phosphonium hexafluorophosphate (BOP)

or N,N-dicylohexylcarbodiimide (DCCI) to produce the carboxylic ester or carboxylic amide.

Further preferred is a process for the preparation of compounds of formula (I) as above comprising one of the following reactions reaction of a compound according to formula (II)

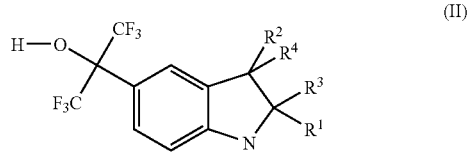

in the presence of a compound according to formula (III)

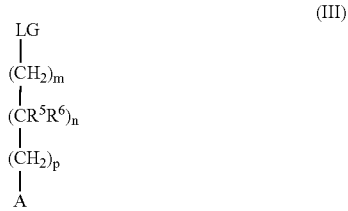

wherein $R^1$ to $R^6$, A, m, n and p are defined as before and LG is a leaving group such as e.g. Cl, Br, I, MsO, TsO, TfO and, wherein hydroxy groups are optionally protected e.g. by treatment with a silylating agent such as e.g. TESCl, particularly in the presence of a base such as e.g. DBU (see in particular Scheme 1);

oxidation of a compound according to formula (Ia)

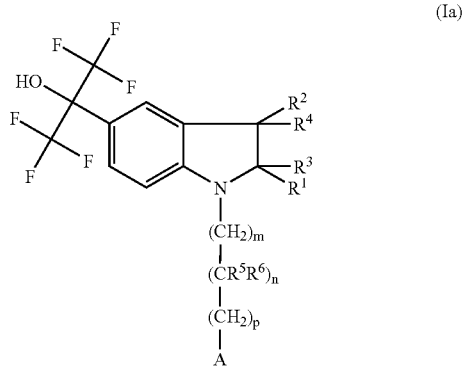

wherein $R^1$, $R^2$, $R^5$, $R^6$, A, m, n and p are defined as before, $R^3$ and $R^4$ are hydrogen, and, wherein hydroxy groups are optionally protected e.g. by treatment with a silylating agent such as e.g. TESCl, particularly in the presence of a base such as e.g. DBU.

Preferred intermediates are:
  5-bromo-1-(benzyl)-2-triisopropylsilanyloxymethyl-1H-indole;
  2-(1-benzyl-2-triisopropylsilanyloxymethyl-1H-indol-5-yl)-1,1,1,3,3,3-hexafluoro-propan-2-ol; and
  2-methyl-5-(2,2,2-trifluoro-1-triethylsilanyloxy-1-trifluoromethyl-ethyl)-2,3-dihydro-1H-indole.

The compounds of formula (I) and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula (I) and their pharmaceutically acceptable salts can be used for the prophylaxis and treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, skin diseases, colitis, pancreatitis, cholestasis of the liver, fibrosis of the liver, macular degeneration or Alzheimer's disease. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by the examples, which have no limiting character.

EXAMPLES

Abbreviations:
$CH_2Cl_2$=dichloromethane, BuLi=n-butyllithium, DBU=1,8-diazabicyclo[5.4.0]undec-7-ene, DDQ=2,3-dichloro-5,6-dicyano-p-benzuoquinone, DIPEA=N-ethyl diisopropylamine, DMF=dimethylformamide, EDCI=N-(3-dimthylaminopropyl)-N'-ethylcarbodiimide hydrochloride, EtOAc=ethylacetate, EtOH=ethanol, $Et_2O$=diethylether, $Et_3N$=triethylamine, eq=equivalent, HOBT=1-hydroxybenzotriazole, $K_2CO_3$=potassium carbonate, $LiAlH_4$=lithium aluminum hydride, LiOH=lithium hydroxide, MeOH=methanol, NaH=sodium hydride, NH$_4$Cl=ammonium chloride, NaOH=sodium hydroxide, NaOMe=sodium methoxide, NCS=N-chlorosuccinimide, NIS=N-iodosuccinimide, RT=room temperature, TBAF=tetrabutyl ammonium fluoride, TESCl=chlorotriethylsilane, THF=tetrahydrofuran, TIPSOTf=triisopropylsilyl-trifluoromethanesulfonate.

General Remarks

All reactions were performed under argon.

Example 1

1,1,1,3,3,3-hexafluoro-2-[2-methyl-1-(5-methyl-2-m-tolyl-oxazol-4-ylmethyl)-1H-indol-5-yl]-propan-2-ol To a solution of 32 mg (0.07 mmol) of 1,1,1,3,3,3-hexafluoro-2-[2-methyl-1-(5-methyl-2-m-tolyl-oxazol-4-ylmethyl)-2,3-dihydro-1H-indol-5-yl]-propan-2-ol (example 47) in 0.5 mL of toluene were added 29 mg (0.33 mmol) of MnO$_2$ powder and the mixture was stirred at 70° C. for 10 hrs. Filtration and evaporation of the solvent gave 33 mg (quantitative) of 1,1,1,3,3,3-hexafluoro-2-[2-methyl-1-(5-methyl-2-m-tolyl-oxazol-4-ylmethyl)-1H-indol-5-yl]-propan-2-ol, grey solid, MS: 483 (MH$^+$).

Example 2

2-(1-benzyl-3-chloro-2-methyl-1H-indol-5-yl)-1,1,1,3,3,3-hexafluoro-propan-2-ol

To a solution of 100 mg (0.26 mmol) of 2-(1-benzyl-2-methyl-1H-indol-5-yl)-1,1,1,3,3,3-hexafluoro-propan-2-ol (example 80) in 1 mL of acetonitrile were added 25 mg (0.185 mmol) of NCS. After stirring at RT for 2 hrs, the mixture was poured into a mixture of a saturated aqueous solution of NH$_4$Cl and Et$_2$O. The phases were separated and the aqueous one was extracted with Et$_2$O. The combined organic phases were dried over Na$_2$SO$_4$ and evaporated. Column chromatography on silica gel with n-heptane/CH$_2$Cl$_2$ 1:3 yielded 70 mg (65%) of 2-(1-benzyl-3-chloro-2-methyl-1H-indol-5-yl)-1,1,1,3,3,3-hexafluoro-propan-2-ol, white solid, MS: 420 ((M−H)$^−$), 1Cl).

Example 3

2-{1-[2-(4-ethyl-phenyl)-5-methyl-oxazol-4-ylmethyl]-2-methyl-1H-indol-5-yl}-1,1,1,3,3,3-hexafluoro-propan-2-ol In analogy to example 1, from 2-{1-[2-(4-ethyl-phenyl)-5-methyl-oxazol-4-ylmethyl]-2-methyl-2,3-dihydro-1H-indol-5-yl}-1,1,1,3,3,3-hexafluoro-propan-2-ol (example 49) was prepared 2-{1-[2-(4-ethyl-phenyl)-5-methyl-oxazol-4-ylmethyl]-2-methyl-1H-indol-5-yl}-1,1,1,3,3,3-hexafluoro-propan-2-ol, dark brown solid, MS: 497 (MH$^+$).

Example 4

1,1,1,3,3,3-hexafluoro-2-{1-[2-(3-trifluormethyl-phenyl)-5-methyl-oxazol-4-ylmethyl]-2-methyl-1H-indol-5-yl}-propan-2-ol In analogy to example 1, from 1,1,1,3,3,3-hexafluoro-2-{2-methyl-1-[5-methyl-2-(3-trifluoromethyl-phenyl)-oxazol-4-ylmethyl]-2,3-dihydro-1H-indol-5-yl}-propan-2-ol (example 56) was prepared 1,1,1,3,3,3-hexafluoro-2-{1-[2-(3-trifluormethyl-phenyl)-5-methyl-oxazol-4-ylmethyl]-2-methyl-1H-indol-5-yl}-propan-2-ol, light yellow solid, MS: 535 (M−H)$^−$.

Example 5

2-(1-benzyl-3-fluoro-2-methyl-1H-indol-5-yl)-1,1,1,3,3,3-hexafluoro-propan-2-ol

To a solution of 21 mg (0.054 mmol) of 2-(1-benzyl-2-methyl-1H-indol-5-yl)-1,1,1,3,3,3-hexafluoro-propan-2-ol (example 80) in 1 mL of dichloroethane were added 16 mg (0.065 mmol) of 1-fluoropyridinium triflate. After stirring at RT for 72 hrs, the mixture was poured into a mixture of a saturated aqueous solution of NH$_4$Cl and Et$_2$O. The phases were separated and the aqueous one was extracted with Et$_2$O. The combined organic phases were dried over Na$_2$SO$_4$ and evaporated. Column chromatography on silica gel with n-heptane/EtOAc 4:1 yielded 2.5 mg (11%) of 2-(1-benzyl-3-fluoro-2-methyl-1H-indol-5-yl)-1,1,1,3,3,3-hexafluoro-propan-2-ol, light brown waxy solid. MS: 404 (M−H)$^−$.

Example 6

1,1,1,3,3,3-hexafluoro-2-{1-[2-(2-fluoro-phenyl)-5-methyl-oxazol-4-ylmethyl]-2-methyl-1H-indol-5-yl}-propan-2-ol In analogy to example 1, from 1,1,1,3,3,3-hexafluoro-2-{1-[2-(2-fluoro-phenyl)-5-methyl-oxazol-4-ylmethyl]-2-methyl-2,3-dihydro-1H-indol-5-yl}-propan-2-ol (example 52) was prepared 1,1,1,3,3,3-hexafluoro-2-{1-[2-(2-fluoro-phenyl)-5-methyl-oxazol-4-ylmethyl]-2-methyl-1H-indol-5-yl}-propan-2-ol, light yellow solid, MS: 485 (M−H)$^−$.

Example 7

1,1,1,3,3,3-hexafluoro-2-[2-methyl-1-(3-morpholin-4-ylmethyl-benzyl)-1H-indol-5-yl]-propan-2-ol In analogy to example 9, from {3-[2-methyl-5-(2,2,2-trifluoro-1-hydroxy-1-trifluoromethyl-ethyl)-indol-1-ylmethyl]-phenyl}-morpholin-4-yl-methanone (example 33) was prepared 1,1,1,3,3,3-hexafluoro-2-[2-methyl-1-(3-morpholin-4-ylmethyl-benzyl)-1H-indol-5-yl]-propan-2-ol, light yellow oil, MS: 487 (MH$^+$).

Example 8

3-[2-methyl-5-(2,2,2-trifluoro-1-hydroxy-1-trifluoromethyl-ethyl)-indol-1-ylmethyl]-benzoic acid methyl ester In analogy to example 1, from 3-[2-methyl-5-(2,2,2-trifluoro-1-hydroxy-1-trifluoromethyl-ethyl)-2,3-dihydro-indol-1-ylmethyl]-benzoic acid methyl ester (example 51), was prepared 3-[2-methyl-5-(2,2,2-trifluoro-1-hydroxy-1-trifluoromethyl-ethyl)-indol-1-ylmethyl]-benzoic acid methyl ester, light yellow solid, MS: 446 (MH$^+$).

Example 9

2-[1-(3-dimethylaminomethyl-benzyl)-2-methyl-1H-indol-5-yl]-1,1,1,3,3,3-hexafluoro-propan-2-ol A solution of 7 mg (0.0153 mmol) of N,N-dimethyl-3-[2-methyl-5-(2,2,2-trifluoro-1-hydroxy-1-trifluoromethyl-ethyl)-indol-1-ylmethyl]-benzamide (example 34) in 0.2 mL of THF was treated with 0.006 mL (0.031 mmol) of borane dimethylsulfide. The mixture was stirred at 70° C. for 10 hrs, treated with MeOH, and concentrated. Column chromatography on silica gel with n-heptane/EtOAc 4:1 to 1:1 yielded 5 mg (72%) of 2-[1-(3-dimethylaminomethyl-benzyl)-2-methyl-1H-indol-5-yl]-1,1,1,3,3, 3-hexafluoro-propan-2-ol, light yellow oil, MS: 445 (MH$^+$).

Example 10

1,1,1,3,3,3-hexafluoro-2-{1-[2-(4-fluoro-3-methyl-phenyl)-5-methyl-oxazol-4-ylmethyl]-2-methyl-1H-indol-5-yl}-propan-2-ol In analogy to example 1, from 1,1,1,3,3,3-hexafluoro-2-{1-[2-(4-fluoro-3-methyl-phenyl)-5-methyl-oxazol-4-ylmethyl]-2-methyl-2,3-dihydro-1H-indol-5-yl}-propan-2-ol (example 54) was prepared 1,1,1,3,3,3-hexafluoro-2-{1-[2-(4-fluoro-3-methyl-phenyl)-5-methyl-oxazol-4-ylmethyl]-2-methyl-1H-indol-5-yl}-propan-2-ol, light yellow solid, MS: 499 (M–H)$^-$.

Example 11

1,1,1,3,3,3-hexafluoro-2-[2-methyl-1-(2-trifluoromethyl-quinolin-6-ylmethyl)-1H-indol-5-yl]-propan-2-ol In analogy to example 1, from 1,1,1,3,3,3-hexafluoro-2-[2-methyl-1-(2-trifluoromethyl-quinolin-6-ylmethyl)-2,3-dihydro-1H-indol-5-yl]-propan-2-ol (example 58) was prepared 1,1,1,3,3,3-hexafluoro-2-[2-methyl-1-(2-trifluoromethyl-quinolin-6-ylmethyl)-1H-indol-5-yl]-propan-2-ol, orange solid, MS: 507 (MH$^+$).

Example 12

2-{1-[2-(3-chloro-phenyl)-5-methyl-oxazol-4-ylmethyl]-2-methyl-1H-indol-5-yl}-1,1,1,3,3,3-hexafluoro-propan-2-ol In analogy to example 1, from 2-{1-[2-(3-chloro-phenyl)-5-methyl-oxazol-4-ylmethyl]-2-methyl-2,3-dihydro-1H-indol-5-yl}-1,1,1,3,3,3-hexafluoro-propan-2-ol (example 53) was prepared 2-{1-[2-(3-chloro-phenyl)-5-methyl-oxazol-4-ylmethyl]-2-methyl-1H-indol-5-yl}-1,1,1,3,3,3-hexafluoro-propan-2-ol, light brown solid, MS: 503 (MH$^+$, 1Cl).

Example 13

2-{1-[2-(4-chloro-phenyl)-5-methyl-oxazol-4-ylmethyl]-2-methyl-1H-indol-5-yl}-1,1,1,3,3,3-hexafluoro-propan-2-ol In analogy to example 1, from 2-{1-[2-(4-chloro-phenyl)-5-methyl-oxazol-4-ylmethyl]-2-methyl-2,3-dihydro-1H-indol-5-yl}-1,1,1,3,3,3-hexafluoro-propan-2-ol (example 62) was prepared 2-{1-[2-(4-chloro-phenyl)-5-methyl-oxazol-4-ylmethyl]-2-methyl-1H-indol-5-yl}-1,1,1,3,3,3-hexafluoro-propan-2-ol, light brown solid, MS: 503 (MH$^+$, 1Cl).

Example 14

1,1,1,3,3,3-hexafluoro-2-(2-methyl-1-quinolin-2-ylmethyl-1H-indol-5-yl)-propan-2-ol In analogy to example 1, from 1,1,1,3,3,3-hexafluoro-2-(2-methyl-1-quinolin-2-ylmethyl-2,3-dihydro-1H-indol-5-yl)-propan-2-ol (example 63) was prepared 1,1,1,3,3,3-hexafluoro-2-(2-methyl-1-quinolin-2-ylmethyl-1H-indol-5-yl)-propan-2-ol, light yellow oil, MS: 439 (MH$^+$).

Example 15

1,1,1,3,3,3-hexafluoro-2-{1-[2-(4-trifluormethyl-phenyl)-5-methyl-oxazol-4-ylmethyl]-2-methyl-1H-indol-5-yl}-propan-2-ol In analogy to example 1, from 1,1,1,3,3,3-hexafluoro-2-{2-methyl-1-[5-methyl-2-(4-trifluoromethyl-phenyl)-oxazol-4-ylmethyl]-2,3-dihydro-1H-indol-5-yl}-propan-2-ol (example 59) was prepared 1,1,1,3,3,3-hexafluoro-2-{1-[2-(4-trifluormethyl-phenyl)-5-methyl-oxazol-4-ylmethyl]-2-methyl-1H-indol-5-yl}-propan-2-ol, light yellow solid, MS: 535 (M–H)$^-$.

Example 16

2-(1-benzyl-1H-indol-5-yl)-1,1,1,3,3,3-hexafluoro-propan-2-ol 16.1

A solution of 5 g (41.96 mmol) of indoline in DMF was treated with 5.8 g (41.96 mmol) of K$_2$CO$_3$ and then at 0° C. dropwise, under intense stirring, with 5.5 mL (46.2 mmol) of benzylbromide. The mixture was stirred at RT for 10 hrs and then for 2 hrs at 60° C. The resulting thick pulp was distributed between a saturated aqueous solution of NH$_4$Cl and Et$_2$O. Drying of the combined organic phases over Na$_2$SO$_4$ and evaporation of the solvent yielded 6.1 g (69%) of N-benzylindoline MS: 210 (MH$^+$).

16.2

6.1 g (29.15 mmol) of N-benzyl indoline were treated with 6.75 g (30.7 mmol) of hexafluoroacetone sesquihydrate and stirred for one week at RT. Distribution between a saturated aqueous solution of NH$_4$Cl and Et$_2$O, drying of the organic phase over Na$_2$SO$_4$, evaporation of the solvent and column chromatography on silica gel (n-heptane/EtOAc 5:1) yielded 8.6 g (78%) of 2-(1-benzyl-2,3-dihydro-1H-indol-5-yl)-1,1,1,3,3,3-hexafluoro-propan-2-ol, pink oil, MS: 376 (MH$^+$).

16.3

A solution of 8.5 g (22.51 mmol) of 2-(1-benzyl-2,3-dihydro-1H-indol-5-yl)-1,1,1,3,3,3-hexafluoro-propan-2-ol in 60 mL toluene was treated with 9.8 g (112 mmol) of MnO$_2$ powder. The mixture was stirred for 10 hrs at RT and 8 hrs at 60° C. Filtration and evaporation of the solvent yielded 8.0 g (95%) of 2-(1-benzyl-1H-indol-5-yl)-1,1,1,3,3,3-hexafluoro-propan-2-ol, yellow solid, MS: 374 (MH$^+$).

Example 17

1,1,1,3,3,3-hexafluoro-2-(2-methyl-1-phenethyl-1H-indol-5-yl)-propan-2-ol 89 mg (ca. 0.17 mmol) of the crude 2-methyl-1-phenethyl-5-(2,2,2-trifluoro-1-triethylsilanyloxy-1-trifluoromethyl-ethyl)-2,3-dihydro-1H-indole obtained (example 55) were dissolved in 1 mL of toluene and treated with 92 mg (1.1 mmol) of $MnO_2$ powder. The mixture was stirred at 80° C. for 48 hrs, filtrated and the solvent evaporated. The residue was dissolved in 1 mL of THF and treated with 0.08 mL of a 1M TBAF solution in THF. Stirring for 30 min, evaporation of the solvent and column chromagraphy on silica gel with n-heptane/EtOAc 3:1 yielded 31 mg (ca. 33%) of 1,1,1,3,3,3-hexafluoro-2-(2-methyl-1-phenethyl-1H-indol-5-yl)-propan-2-ol, light brown oil, MS: 400 $(M-H)^-$.

Example 18

1,1,1,3,3,3-hexafluoro-2-[2-methyl-1-(5-methyl-2-phenyl-oxazol-4-ylmethyl)-1H-indol-5-yl]-propan-2-ol In analogy to example 1, from 1,1,1,3,3,3-hexafluoro-2-[2-methyl-1-(5-methyl-2-phenyl-oxazol-4-ylmethyl)-2,3-dihydro-1H-indol-5-yl]-propan-2-ol (example 57) was prepared 1,1,1,3,3,3-hexafluoro-2-[2-methyl-1-(5-methyl-2-phenyl-oxazol-4-ylmethyl)-1H-indol-5-yl]-propan-2-ol, brownish solid, MS: 469 $(MH^+)$.

Example 19

2-(1-benzyl-2,3-dichloro-1H-indol-5-yl)-1,1,1,3,3,3-hexafluoro-propan-2-ol

A solution of 400 mg (1.07 mmol) of 2-(1-benzyl-1H-indol-5-yl)-1,1,1,3,3,3-hexafluoro-propan-2-ol (example 16) in 2 mL $CH_2Cl_2$ was treated portionwise with 286 mg (2.14 mmol) of NCS and stirred at RT for 10 hrs. Evaporation of the solvent and column chromatography on silica gel with n-heptane/EtOAc 3:1 to 1:1 yielded 100 mg (21%) of 2-(1-benzyl-2,3-dichloro-1H-indol-5-yl)-1,1,1,3,3,3-hexafluoro-propan-2-ol, light brown oil, MS: 441 $(M-H)^-$, 2Cl.

Example 20

2-{1-[2-(4-tert-butyl-phenyl)-5-methyl-oxazol-4-ylmethyl]-2-methyl-1H-indol-5-yl}-1,1,1,3,3,3-hexafluoro-propan-2-ol In analogy to example 1, from 2-{1-[2-(4-tert-butyl-phenyl)-5-methyl-oxazol-4-ylmethyl]-2-methyl-2,3-dihydro-1H-indol-5-yl}-1,1,1,3,3,3-hexafluoro-propan-2-ol (example 66) was prepared 2-{1-[2-(4-tert-butyl-phenyl)-5-methyl-oxazol-4-ylmethyl]-2-methyl-1H-indol-5-yl}-1,1,1,3,3,3-hexafluoro-propan-2-ol, red foam, MS: 525 $(MH^+)$.

Example 21

2-{1-[2-(4-chloro-phenyl)-5-methyl-thiazol-4-ylmethyl]-2-methyl-1H-indol-5-yl}-1,1,1,3,3,3-hexafluoro-propan-2-ol In analogy to example 1, from 2-{1-[2-(4-chloro-phenyl)-5-methyl-thiazol-4-ylmethyl]-2-methyl-2,3-dihydro-1H-indol-5-yl}-1,1,1,3,3,3-hexafluoro-propan-2-ol (example 71) was prepared 2-{1-[2-(4-chloro-phenyl)-5-methyl-thiazol-4-ylmethyl]-2-methyl-1H-indol-5-yl}-1,1,1,3,3,3-hexafluoro-propan-2-ol, yellow solid, MS: 517 $((M-H^-), 1Cl)$.

Example 22

2-(1-benzyl-2,3-diiodo-1H-indol-5-yl)-1,1,1,3,3,3-hexafluoro-propan-2-ol

In analogy to example 26.2 from 2-(1-benzyl-1H-indol-5-yl)-1,1,1,3,3,3-hexafluoro-propan-2-ol (example 16) and NIS and stirring at 100° C. instead of 65° C. was prepared 2-(1-benzyl-2,3-diiodo-1H-indol-5-yl)-1,1,1,3,3,3-hexafluoro-propan-2-ol, light brown oil, MS: 624 $(M-H)^-$.

Example 23 benzyl-5-(2,2,2-trifluoro-1-hydroxy-1-trifluoromethyl-ethyl)-1H-indole-2-carbaldehyde To a solution of 1.03 g (2.56 mmol) of 2-(1-benzyl-2-hydroxymethyl-1H-indol-5-yl)-1,1,1,3,3,3-hexafluoro-propan-2-ol (example 41) in 10 mL toluene were added 2.22 g (25.6 mmol) of $MnO_2$ powder. The mixture was stirred at 80° C. overnight. Filtration through decalite, evaporation of the solvent and column chromatography on silica gel with n-heptane/EtOAc 3:1 yielded 0.342 g (33%) of 1-benzyl-5-(2,2,2-trifluoro-1-hydroxy-1-trifluoromethyl-ethyl)-1H-indole-2-carbaldehyde, MS: 400 $(M-H)^-$.

Example 24

2-(1-biphenyl-3-ylmethyl-2-methyl-1H-indol-5-yl)-1,1,1,3,3,3-hexafluoro-propan-2-ol In analogy to example 1, from 2-(1-biphenyl-3-ylmethyl-2-methyl-2,3-dihydro-1H-indol-5-yl)-1,1,1,3,3,3-hexafluoro-propan-2-ol (example 64) was prepared 2-(1-biphenyl-3-ylmethyl-2-methyl-1H-indol-5-yl)-1,1,1,3,3,3-hexafluoro-propan-2-ol, yellow viscous oil, MS: 464 $(MH^+)$.

Example 25

1,1,1,3,3,3-hexafluoro-2-(2-methyl-1-naphthalen-1-ylmethyl-1H-indol-5-yl)-propan-2-ol In analogy to example 1, from 1,1,1,3,3,3-hexafluoro-2-(2-methyl-1-naphthalen-1-ylmethyl-2,3-dihydro-1H-indol-5-yl)-propan-2-ol (example 60), was prepared 1,1,1,3,3,3-hexafluoro-2-(2-methyl-1-naphthalen-1-ylmethyl-1H-indol-5-yl)-propan-2-ol, light brown solid, MS: 438 $(MH^+)$.

Example 26

2-(1-benzyl-3-iodo-1H-indol-5-yl)-1,1,1,3,3,3-hexafluoro-propan-2-ol 26.1
A solution of 6.72 g (18 mmol) 2-(1-benzyl-1H-indol-5-yl)-1,1,1,3,3,3-hexafluoro-propan-2-ol (example 16) in DMF was treated with 4.03 mL (27.0 mmol) of DBU and at 0° C. then dropwise with 4.12 mL (27 mmol) TESCl. The mixture was stirred for 2 hrs at RT and the solvent was evaporated. Column chromatography on silicagel with n-heptane/EtOAc 6:1 yielded 7.7 g (88%) of 1-benzyl-5-(2,2,2-trifluoro-1-triethylsilanyloxy-1-trifluoromethyl-ethyl)-1H-indole, light yellow oil, MS: 489 $(MH^+)$.

26.2

A solution of 1 g (2.1 mmol) of 1-benzyl-5-(2,2,2-trifluoro-1-triethylsilanyloxy-1-trifluoromethyl-ethyl)-1H-indole in 7 mL DMF was treated portionwise at 0° C. with 1.94 g (8.6 mmol) of NIS and stirred for 2 hrs at 65° C. The mixture was poured into a mixture of a saturated aqueous solution of $NH_4Cl$ containing $NaS_2O_3$ and $Et_2O$. The phases were separated and the aqueous one was extracted with $Et_2O$. The combined organic phases were dried over $Na_2SO_4$ and evaporated to yield 1.1 g (72%) of 1-benzyl-3-iodo-5-(2,2,2-trifluoro-1-triethylsilanyloxy-1-trifluoromethyl-ethyl)-1H-indole, of which 50 mg were dissolved in 1 mL of MeOH and treated with 0.2 mL of 2M NaOMe in MeOH. After stirring for 30 min at RT, the crude mixture was distributed between aqueous HCl and $Et_2O$. The combined organic phases were dried over $Na_2SO_4$ and evaporated. Column chromatography on silica gel with n-heptane/EtOAc 4:1 yielded 30 mg of 2-(1-benzyl-3-iodo-1H-indol-5-yl)-1,1,1,3,3,3-hexafluoro-propan-2-ol, light brown solid, MS 498 $(M-H)^-$.

Example 27

N-benzyl-N-methyl-3-[2-methyl-5-(2,2,2-trifluoro-1-hydroxy-1-trifluoromethyl-ethyl)-indol-1-ylmethyl]-benzamide In analogy to example 34, from 3-[2-methyl-5-(2,2,2-trifluoro-1-hydroxy-1-trifluoromethyl-ethyl)-indol-1-ylmethyl]-benzoic acid (example 31) and N-methyl benzylamine was prepared N-benzyl-N-methyl-3-[2-methyl-5-(2,2,2-trifluoro-1-hydroxy-1-trifluoromethyl-ethyl)-indol-1-ylmethyl]-benzamide, colorless solid, MS: 535 $(MH^+)$.

Example 28

4-[2-methyl-5-(2,2,2-trifluoro-1-hydroxy-1-trifluoromethyl-ethyl)-indol-1-ylmethyl]-benzoic acid methyl ester In analogy to example 1, from 4-[2-methyl-5-(2,2,2-trifluoro-1-hydroxy-1-trifluoromethyl-ethyl)-2,3-dihydro-indol-1-ylmethyl]-benzoic acid methyl ester (example 69) was prepared 4-[2-methyl-5-(2,2,2-trifluoro-1-hydroxy-1-trifluoromethyl-ethyl)-indol-1-ylmethyl]-benzoic acid methyl ester, light yellow solid, MS: 446 $(MH^+)$.

Example 29

N-methyl-3-[2-methyl-5-(2,2,2-trifluoro-1-hydroxy-1-trifluoromethyl-ethyl)-indol-1-ylmethyl]-N-phenethyl-benzamide In analogy to example 34, from 3-[2-methyl-5-(2,2,2-trifluoro-1-hydroxy-1-trifluoromethyl-ethyl)-indol-1-ylmethyl]-benzoic acid (example 31) and N-methyl-2-phenethylamine was prepared N-methyl-3-[2-methyl-5-(2,2,2-trifluoro-1-hydroxy-1-trifluoromethyl-ethyl)-indol-1-ylmethyl]-N-phenethyl-benzamide, colorless solid, MS: 549 $(MH^+)$.

Example 30

(methyl-{3-[2-methyl-5-(2,2,2-trifluoro-1-hydroxy-1-trifluoromethyl-ethyl)-indol-1-ylmethyl]-benzoyl}-amino)-acetic acid ethyl ester In analogy to example 34, from 3-[2-methyl-5-(2,2,2-trifluoro-1-hydroxy-1-trifluoromethyl-ethyl)-indol-1-ylmethyl]-benzoic acid (example 31) and sarcosine ethylester hydrochloride was prepared (methyl-{3-[2-methyl-5-(2,2,2-trifluoro-1-hydroxy-1-trifluoromethyl-ethyl)-indol-1-ylmethyl]-benzolyl}-amino)-acetic acid ethyl ester, colorless solid, MS: 531 $(MH^+)$.

Example 31

3-[2-methyl-5-(2,2,2-trifluoro-1-hydroxy-1-trifluoromethyl-ethyl)-indol-1-ylmethyl]-benzoic acid In analogy to example 68, from 3-[2-methyl-5-(2,2,2-trifluoro-1-hydroxy-1-trifluoromethyl-ethyl)-indol-1-ylmethyl]-benzoic acid methyl ester (example 8) was prepared 3-[2-methyl-5-(2,2,2-trifluoro-1-hydroxy-1-trifluoromethyl-ethyl)-indol-1-ylmethyl]-benzoic acid, red solid, MS: 430 $(M-H)^-$.

Example 32

N-[2-(1H-indol-3-yl)-ethyl]-N-methyl-3-[2-methyl-5-(2,2,2-trifluoro-1-hydroxy-1-trifluoromethyl-ethyl)-indol-1-ylmethyl]-benzamide In analogy to example 34, from 3-[2-methyl-5-(2,2,2-trifluoro-1-hydroxy-1-trifluoromethyl-ethyl)-indol-1-ylmethyl]-benzoic acid (example 31) and [2-(1H-indol-3-yl)-ethyl]-methyl-amine was prepared N-[2-(1H-indol-3-yl)-ethyl]-N-methyl-3-[2-methyl-5-(2,2,2-trifluoro-1-hydroxy-1-trifluoromethyl-ethyl)-indol-1-ylmethyl]-benzamide, colorless solid, MS: 588 $(MH^+)$.

Example 33

{3-[2-methyl-5-(2,2,2-trifluoro-1-hydroxy-1-trifluoromethyl-ethyl)-indol-1-ylmethyl]-phenyl}-morpholin-4-yl-methanone In analogy to example 34, from 3-[2-methyl-5-(2,2,2-trifluoro-1-hydroxy-1-trifluoromethyl-ethyl)-indol-1-ylmethyl]-benzoic acid (example 31) and morpholine was prepared {3-[2-methyl-5-(2,2,2-trifluoro-1-hydroxy-1-trifluoromethyl-ethyl)-indol-1-ylmethyl]-phenyl}-morpholin-4-yl-methanone, colorless solid, MS: 501 $(MH^+)$.

Example 34

N,N-dimethyl-3-[2-methyl-5-(2,2,2-trifluoro-1-hydroxy-1-trifluoromethyl-ethyl)-indol-1-ylmethyl]-benzamide A solution of 60 mg (0.139 mmol) of 3-[2-methyl-5-(2,2,2-trifluoro-1-hydroxy-1-trifluoromethyl-ethyl)-indol-1-ylmethyl]-benzoic acid (example 31) in 1 mL of THF was treated with 31 mg (0.417 mmol) of dimethylamine hydrochloride, 0.09 mL (0.834 mmol) of N-methylmorpholine, 3.7 mg (0.028 mmol) of HOBT, and 37 mg (0.195 mmol) of EDCI. The mixture was stirred for 10 hrs at RT and the solvent evaporated. Column chromatography on silica gel with n-heptane/EtOAc 4:1 to 1:1 yielded 39 mg (60%) of N,N-dimethyl-3-[2-methyl-5-(2,2,2-trifluoro-1-hydroxy-1-trifluoromethyl-ethyl)-indol-1-ylmethyl]-benzamide, colorless solid, MS: 459 $(MH^+)$.

Example 35

N-methyl-3-[2-methyl-5-(2,2,2-trifluoro-1-hydroxy-1-trifluoromethyl-ethyl)-indol-1-ylmethyl]-N-(2-pyridin-2-yl-ethyl)-benzamide In analogy to example 34, from 3-[2-methyl-5-(2,2,2-trifluoro-1-hydroxy-1-trifluoromethyl-ethyl)-indol-1-ylmethyl]-benzoic acid (example 31) and 2-(2-aminoethyl)pyridine was prepared N-methyl-3-[2-methyl-5-(2,2,2-trifluoro-1-hydroxy-1-trifluoromethyl-ethyl)-indol-1-ylmethyl]-N-(2-pyridin-2-yl-ethyl)-benzamide, colorless solid, MS: 550 $(MH^+)$.

Example 36

N-methyl-3-[2-methyl-5-(2,2,2-trifluoro-1-hydroxy-1-trifluoromethyl-ethyl)-indol-1-ylmethyl]-N-pyridin-2-ylmethyl-benzamide In analogy to example 34, from 3-[2-methyl-5-(2,2,2-trifluoro-1-hydroxy-1-trifluoromethyl-ethyl)-indol-1-ylmethyl]-benzoic acid (example 31) and methylpyridin-2-ylmethylamine was prepared N-methyl-3-[2-methyl-5-(2,2,2-trifluoro-1-hydroxy-1-trifluoromethyl-ethyl)-indol-1-ylmethyl]-N-pyridin-2-ylmethyl-benzamide, colorless solid, MS: 536 $(MH^+)$.

Example 37

2-[1-benzyl-2-(1-hydroxy-ethyl)-1H-indol-5-yl]-1,1,1,3,3,3-hexafluoro-propan-2-ol 37.1
To a solution of 0.33 g (0.82 mmol) of 1-benzyl-5-(2,2,2-trifluoro-1-hydroxy-1-trifluoromethyl-ethyl)-1H-indole-2-carbaldehyde (example 23) in 3 mL of DMF at 0° C. were added 0.15 mL (0.99 mmol) of DBU, followed by 0.17 mL (0.99 mmol) of TESCl. The mixture was stirred at RT overnight and then poured into a mixture of a saturated aqueous solution of $NH_4Cl$ and $Et_2O$. The phases were separated and the aqueous one was extracted with $Et_2O$. The combined organic phases were dried over $Na_2SO_4$ and evaporated to yield 0.389 g (92%) of 1-benzyl-5-(2,2,2-trifluoro-1-triethylsilanyloxy-1-trifluoromethyl-ethyl)-1H-indole-2-carbaldehyde, MS: 516 $(MH^+)$.

37.2
To a solution of 0.11 g (0.21 mmol) of 1-benzyl-5-(2,2,2-trifluoro-1-triethylsilanyloxy-1-trifluoromethyl-ethyl)-1H-indole-2-carbaldehyde in 3 mL of THF were added 0.14 mL (0.42 mmol) of methyl magnesium bromide dropwise at 0° C. under an argon stream. The mixture was stirred at RT for 1.5 h and poured into a mixture of a saturated aqueous solution of $NH_4Cl$ and $Et_2O$. The phases were separated and the aqueous one was extracted with $Et_2O$. The combined organic phases were dried over $Na_2SO_4$ and evaporated to yield 0.118 g (quantitative) of crude 1-[1-benzyl-5-(2,2,2-trifluoro-1-triethylsilanyloxy-1-trifluoromethyl-ethyl)-1H-indol-2-yl]-ethanol, which was dissolved in 2 mL of THF and treated with 0.43 mL (0.43 mmol) of a 1M TBAF-solution in THF, stirred for one hour and then poured into a mixture of a saturated aqueous solution of $NH_4Cl$ and $Et_2O$. The phases were separated and the aqueous one was extracted with $Et_2O$. The combined organic phases were dried over $Na_2SO_4$ and evaporated to yield 0.066 g (74%) of 2-[1-benzyl-2-(1-hydroxy-ethyl)-1H-indol-5-yl]-1,1,1,3,3,3-hexafluoro-propan-2-ol, yellow solid, MS: 418 $(M–H)^-$.

Example 38

1-[1-benzyl-5-(2,2,2-trifluoro-1-hydroxy-1-trifluoromethyl-ethyl)-1H-indol-2-yl]-propan-1-ol In analogy to example 37.2, from 1-benzyl-5-(2,2,2-trifluoro-1-triethylsilanyloxy-1-trifluoromethyl-ethyl)-1H-indole-2-carbaldehyde and ethylmagnesium bromide was prepared 1-[1-benzyl-5-(2,2,2-trifluoro-1-hydroxy-1-trifluoromethyl-ethyl)-1H-indol-2-yl]-propan-1-ol, orange waxy solid, MS: 432 $(MH^+)$.

Example 39

1,1,1,3,3,3-hexafluoro-2-{1-[2-(4-isopropoxy-phenyl)-5-methyl-oxazol-4-ylmethyl]-2-methyl-1H-indol-5-yl}-propan-2-ol In analogy to example 1, from 1,1,1,3,3,3-hexafluoro-2-{1-[2-(4-isopropoxy-phenyl)-5-methyl-oxazol-4-ylmethyl]-2-methyl-2,3-dihydro-1H-indol-5-yl}-propan-2-ol (example 73) was prepared 1,1,1,3,3,3-hexafluoro-2-{1-[2-(4-isopropoxy-phenyl)-5-methyl-oxazol-4-ylmethyl]-2-methyl-1H-indol-5-yl}-propan-2-ol, light yellow solid, MS: 525 $(M–H)^-$.

Example 40

1,1,1,3,3,3-hexafluoro-2-[1-(2-hydroxy-1-phenyl-ethyl)-2-methyl-1H-indol-5-yl]-propan-2-ol A solution of 40 mg (0.094 mmol) 1,1,1,3,3,3-hexafluoro-2-[1-(2-hydroxy-1-phenyl-ethyl)-2-methyl-2,3-dihydro-1H-indol-5-yl]-propan-2-ol (example 70) in 1 mL of toluene was treated with 45 mg (0.47 mmol) of $MnO_2$. After stirring at 80° C. for 8 hrs, 0.5 mL of dioxane and 22 mg (0.094 mmol) of DDQ were added. The resulting mixture was stirred at RT overnight and poured into a saturated aqueous solution of $NH_4Cl$ and $Et_2O$. The phases were separated and the aqueous one was extracted with $Et_2O$. The combined organic phases were dried over $Na_2SO_4$ and evaporated. Column chromatography on silica gel with n-heptane/EtOAc 2:1 yielded 15 mg (38%) of 1,1,1,3,3,3-hexafluoro-2-[1-(2-hydroxy-1-phenyl-ethyl)-2-methyl-1H-indol-5-yl]-propan-2-ol, brown oil, MS: 418 $(MH^+)$.

Example 41

2-(1-benzyl-2-hydroxymethyl-1H-indol-5-yl)-1,1,1,3,3,3-hexafluoro-propan-2-ol 41.1
To a solution of 5 g (19 mmol) of 5-bromoindol-2-carboxylic acid ethyl ester in 20 mL of anhydrous DMF was added portionwise 1.06 g (24 mmol) of NaH (55% in oil). The mixture was stirred at RT for 45 minutes, treated dropwise with 2.9 mL (24 mmol) of benzyl bromide and stirred for three hours. After addition of a saturated aqueous solution of $NH_4Cl$ and $Et_2O$, the phases were separated and the aqueous one was extracted with $Et_2O$. The combined organic phases were dried over $Na_2SO_4$ and evaporated to yield 6.7 g (98%) of crude 5-bromo-1-benzylindole-2-carboxylic acid ethyl ester, orange oil, MS: 358 $(MH^+)$.

41.2

To a solution of 6.7 g (19 mmol) of 5-bromo-1-(benzyl) indole-2-carboxylic acid ethyl ester in 25 mL of anhydrous THF at 0° C. were added portionwise 1.42 g (37 mmol) of LiAlH$_4$ and the resulting mixture was stirred at 0° C. for 2 h. After addition of a saturated aqueous solution of NH$_4$Cl and Et$_2$O, the phases were separated and the aqueous one was extracted with Et$_2$O. The combined organic phases were dried over Na$_2$SO$_4$ and evaporated to yield 5.8 g (ca 19 mmol) of [5-bromo-1-(benzyl)-1H-indol-2-yl]-methanol, that was dissolved in 30 mL of CH$_2$Cl$_2$ and treated at 0° C. with 4.75 mL (28 mmol) of DIPEA 7.5 mL (28 mmol) of TIPSOTf. The mixture was stirred at RT for 1 h and added to saturated aqueous NH$_4$Cl and Et$_2$O. The phases were separated and the aqueous one was extracted with Et$_2$O. The combined organic phases were dried over Na$_2$SO$_4$ and evaporated to yield 7.3 g (81%) of 5-bromo-1-(benzyl)-2-triisopropylsilanyloxymethyl-1H-indole, off-white solid, MS: 473 (MH$^+$).

41.3

To a solution of 0.98 g (2.1 mmol) of 1-benzyl-5-bromo-2-triisopropylsilanyloxymethyl-1H-indole in 10 mL of THF at −78° C. under argon were added dropwise 1.42 mL (1.1 eq.) of a 1.6 M BuLi—solution in THF. The mixture was stirred at RT for 15 minutes. The solution was cooled again to −78° C. and hexafluoroacetone was bubbled into the solution for 1 minute. Stirring was continued for 10 minutes before ice cubes were added and the mixture was poured into a saturated aqueous solution of NH$_4$Cl and Et$_2$O. The phases were separated and the aqueous one was extracted with Et$_2$O. The combined organic phases were dried over Na$_2$SO$_4$ and evaporated. Column chromatography on silica gel with n-heptane/ CH$_2$Cl$_2$ 2:1 yielded 707 mg (61%) of 2-(1-benzyl-2-triisopropylsilanyl oxymethyl-1H-indol-5-yl)-1,1,1,3,3,3-hexafluoro-propan-2-ol, MS: 558 (M−H)$^-$.

41.4

To a solution of 0.93 g (1.66 mmol) of 2-(1-benzyl-2-triisopropylsilanyloxymethyl-1H-indol--yl)-1,1,1,3,3,3-hexafluoro-propan-2-ol in 10 mL of THF were added 1.66 mL (1.66 mmol) of a 1 M solution of tetrabutyl ammonium fluoride in THF. The mixture was stirred at RT for 1 h and poured into a mixture of a saturated aqueous solution of NH$_4$Cl and Et$_2$O. The phases were separated and the aqueous one was extracted with Et$_2$O. The combined organic phases were dried over Na$_2$SO$_4$ and evaporated to yield 1.0 g (quantitative) of 2-(1-benzyl-2-hydroxymethyl-1H-indol-5-yl)-1,1,1,3,3,3-hexafluoro-propan-2-ol, light yellow semisolid, MS: 402 (M−H)$^-$.

Example 42

N-cyclohexyl-N-methyl-3-[2-methyl-5-(2,2,2-trifluoro-1-hydroxy-1-trifluoromethyl-ethyl)-indol-1-ylmethyl]-benzamide In analogy to example 34, from 3-[2-methyl-5-(2,2,2-trifluoro-1-hydroxy-1-trifluoromethyl-ethyl)-indol-1-ylmethyl]-benzoic acid (example 31) and N-methyl cyclohexylamine was prepared N-cyclohexyl-N-methyl-3-[2-methyl-5-(2,2,2-trifluoro-1-hydroxy-1-trifluoromethyl-ethyl)-indol-1-ylmethyl]-benzamide, colorless solid, MS: 527 (MH$^+$).

Example 43

2-[1-(5-chloro-benzo[b]thiophen-3-ylmethyl)-2-methyl-2,3-dihydro-1H-indol-5-yl]-1,1,1,3,3,3-hexafluoro-propan-2-ol In analogy to example 51.3, from 2-methyl-5-(2,2,2-trifluoro-1-triethylsilanyloxy-1-trifluoromethyl-ethyl)-2,3-dihydro-1H-indole (example 51.2) and 5-chloro-3-chloromethyl-benzo[b]thiophene was prepared 2-[1-(5-chloro-benzo [b]thiophen-3-ylmethyl)-2-methyl-2,3-dihydro-1H-indol-5-yl]-1,1,1,3,3,3-hexafluoro-propan-2-ol, light brown oil, MS: 478 (M−H)$^-$.

Example 44

1,1,1,3,3,3-hexafluoro-2-[2-methyl-1-(5-methyl-3-phenyl-isoxazol-4-ylmethyl)-2,3-dihydro-1H-indol-5-yl]-propan-2-ol In analogy to example 51.3, from 2-methyl-5-(2,2,2-trifluoro-1-triethylsilanyloxy-1-trifluoromethyl-ethyl)-2,3-dihydro-1H-indole (example 51.2) and 4-chloromethyl-5-methyl-3-phenyl-isoxazole was prepared 1,1,1,3,3,3-hexafluoro-2-[2-methyl-1-(5-methyl-3-phenyl-isoxazol-4-ylmethyl)-2,3-dihydro-1H-indol-5-yl]-propan-2-ol, light brown oil, MS: 469 (M−H)$^-$.

Example 45

2-(2-chloro-phenyl)-4-[2-methyl-5-(2,2,2-trifluoro-1-hydroxy-1-trifluoromethyl-ethyl)-2,3-dihydro-indol-1-ylmethyl]-oxazole-5-carboxylic acid methyl ester 45.1

4-bromomethyl-2-(2-chloro-phenyl)-oxazole-5-carboxylic acid methyl ester was prepared from 2-Chlorobenzaldehyde and racemic glycine in analogy to procedures by Cynkowski et al. (J. Chem. Soc. Chem. Commun. 1995, 2335-2336), Bouillot et al., (WO2004006922), and Morita et al. (JP09095482).

45.2

In analogy to example 51.3, from 2-methyl-5-(2,2,2-trifluoro-1-triethylsilanyloxy-1-trifluoromethyl-ethyl)-2,3-dihydro-1H-indole and 4-bromomethyl-2-(2-chloro-phenyl)-oxazole-5-carboxylic acid methyl ester was prepared 2-(2-chloro-phenyl)-4-[2-methyl-5-(2,2,2-trifluoro-1-hydroxy-1-trifluoromethyl-ethyl)-2,3-dihydro-indol-1-ylmethyl]-oxazole-5-carboxylic acid methyl ester, yellow oil, MS: 547 ((M−H$^-$), 1Cl).

Example 46

1,1,1,3,3,3-hexafluoro-2-[2-methyl-1-(5-methyl-2-o-tolyl-oxazol-4-ylmethyl)-2,3-dihydro-1H-indol-5-yl]-propan-2-ol 46.1

2-(2-methyl-phenyl)-4-Chloromethyl-5-methyl-oxazole was prepared from 2-methyl-benzaldehyde in analogy to the procedure by Binggeli et al. (WO200292084).

46.2

In analogy to example 51.3, from 2-methyl-5-(2,2,2-trifluoro-1-triethylsilanyloxy-1-trifluoromethyl-ethyl)-2,3-dihydro-1H-indole (example 51.2) and 2-(2-methyl-phenyl)-4-chloromethyl-5-methyl-oxazole was prepared 1,1,1,3,3,3-hexafluoro-2-[2-methyl-1-(5-methyl-2-o-tolyl-oxazol-4-ylmethyl)-2,3-dihydro-1H-indol-5-yl]-propan-2-ol

Example 47

1,1,1,3,3,3-hexafluoro-2-[2-methyl-1-(5-methyl-2-m-tolyl-oxazol-4-ylmethyl)-2,3-dihydro-1H-indol-5-yl]-propan-2-ol 47.1
4-chloromethyl-2-(3-methyl-phenyl)-5-methyl-oxazole was prepared from 3-methyl-benzaldehyde in analogy to the procedure by Binggeli et al. (WO200292084).

47.2
In analogy to example 51.3, from 2-methyl-5-(2,2,2-trifluoro-1-triethylsilanyloxy-1-trifluoromethyl-ethyl)-2,3-dihydro-1H-indole (example 51.2) and 4-chloromethyl-2-(3-methyl-phenyl)-5-methyl-oxazole was prepared 1,1,1,3,3,3-hexafluoro-2-[2-methyl-1-(5-methyl-2-m-tolyl-oxazol-4-ylmethyl)-2,3-dihydro-1H-indol-5-yl]-propan-2-ol, green solid, MS: 485 (MH$^+$).

Example 48

2-(1-benzyl-2-methyl-2,3-dihydro-1H-indol-5-yl)-1,1,1,3,3,3-hexafluoro-propan-2-ol 48.1
To a solution of 1 g (7.5 mmol) of 2-methyl-2,3-dihydro-1H-indole in anhydrous DMF were added 1.03 g (7.5 mmol) of $K_2CO_3$ and then dropwise 0.97 mL (8.0 mmol) of benzylbromide. The mixture was stirred at RT for 3 hrs and then distributed between $Et_2O$ and a saturated aqueous solution of $NH_4Cl$. The combined organic phases were dried over $Na_2SO_4$ and evaporated to yield 1.7 g (quantitative) of crude 1-benzyl-2-methyl-2,3-dihydro-1H-indole, light blue oil, MS: 224 (MH$^+$).

48.2
To 523 mg (2.34 mmol) of 1-benzyl-2-methyl-2,3-dihydro-1H-indole were added 1.28 mL (12 mmol) of hexafluoroacetone sesquihydrate. The mixture was stirred at 80° C. for 4 hrs and then was distributed between $Et_2O$ and a saturated aqueous solution of $NH_4Cl$. The combined organic phases were dried over $Na_2SO_4$ and evaporated. Column chromatography on silica gel with n-heptane/EtOAc 4:1 yielded 311 mg (34%) of 2-(1-benzyl-2-methyl-2,3-dihydro-1H-indol-5-yl)-1,1,1,3,3,3-hexafluoro-propan-2-ol, light green oil, MS: 388 (M–H)$^-$.

Example 49

2-{1-[2-(4-ethyl-phenyl)-5-methyl-oxazol-4-ylmethyl]-2-methyl-2,3-dihydro-1H-indol-5-yl}-1,1,1,3,3,3-hexafluoro-propan-2-ol 49.1
2-(3-ethyl-phenyl)-4-chloromethyl-5-methyl-oxazole was prepared from 3-ethyl-benzaldehyde in analogy to the procedure by Binggeli et al. (WO200292084).

49.2
In analogy to example 51.3, from 2-methyl-5-(2,2,2-trifluoro-1-triethylsilanyloxy-1-trifluoromethyl-ethyl)-2,3-dihydro-1H-indole (example 51.2) and 2-(3-ethyl-phenyl)-4-chloromethyl-5-methyl-oxazole was prepared 2-{1-[2-(3-ethyl-phenyl)-5-methyl-oxazol-4-ylmethyl]-2-methyl-2,3-dihydro-1H-indol-5-yl}-1,1,1,3,3,3-hexafluoro-propan-2-ol, orange gum, MS: 499 (MH$^+$).

Example 50

1,1,1,3,3,3-hexafluoro-2-[1-(3-hydroxymethyl-benzyl)-2-methyl-2,3-dihydro-1H-indol-5-yl]-propan-2-ol A solution of 1.29 g (2.24 mmol) of 3-[2-methyl-5-(2,2,2-trifluoro-1-hydroxy-1-trifluoromethyl-ethyl)-2,3-dihydro-indol-1-ylmethyl]-benzoic acid methyl ester (example 51) in 5 mL of THF was treated at 0° C. with 87 mg (2.24 mmol) of a $LiAlH_4$. The mixture was stirred for 1 h at RT, treated subsequently with MeOH and $H_2O$. Distribution between $Et_2O$ and a saturated aqueous solution of $NH_4Cl$, drying of the combined organic phases over $Na_2SO_4$ and evaporation, yielded 1.07 g (90%) of {3-[2-methyl-5-(2,2,2-trifluoro-1-triethylsilanyloxy-1-trifluoromethyl-ethyl)-2,3-dihydro-indol-1-ylmethyl]-phenyl}-methanol, of which 50 mg were dissolved in 1 mL of THF and treated with 0.14 mL of a 1M TBAF-solution in THF. After stirring at RT for 2 hrs, the solution distributed between $Et_2O$ and saturated aqueous $NH_4Cl$. The combined organic phases were dried over $Na_2SO_4$ and evaporated, yielding 49 mg (quantitative) of 1,1,1,3,3,3-hexafluoro-2-[1-(3-hydroxymethyl-benzyl)-2-methyl-2,3-dihydro-1H-indol-5-yl]-propan-2-ol, yellow gum, MS: 420 (MH$^+$).

Example 51

3-[2-methyl-5-(2,2,2-trifluoro-1-hydroxy-1-trifluoromethyl-ethyl)-2,3-dihydro-indol-1-ylmethyl]-benzoic acid methyl ester 51.1
To 2.5 mL (19.1 mmol) of 2-methyl-2,3-dihydro-1H-indole were added 2.1 mL (19.1 mmol) of hexafluoroacetone sesquihydrate dropwise at 0° C. After stirring at 80° C. for 12 hrs, the mixture was distributed between $Et_2O$ and a saturated aqueous solution of $NH_4Cl$. The combined organic phases were dried over $Na_2SO_4$ and evaporated. Column chromatography on silica gel with n-heptane/EtOAc 4:1 yielded 1.41 g (25%) of 1,1,1,3,3,3-hexafluoro-2-(2-methyl-2,3-dihydro-1H-indol-5-yl)-propan-2-ol, off-white solid, MS: 300 (MH$^+$).

51.2
To a solution of 5.9 g (19.7 mmol) of 1,1,1,3,3,3-hexafluoro-2-(2-methyl-2,3-dihydro-1H-indol-5-yl)-propan-2-ol in DMF were added 2.94 mL (19.7 mmol) of DBU and after 30 min 3.3 mL (19.7 mmol) of TESCl. After 10 hrs, additional 0.44 mL (3.0 mmol) of DBU and 1.65 mL (9.85 mmol) of TESCl were added and stirring was continued for 2 hrs. The solvent and excess TESCl were evaporated i.v. and the residue was distributed between $Et_2O$ and a saturated aqueous solution of $NH_4Cl$. The combined organic phases were dried over $Na_2SO_4$ and evaporated to yield 8.1 g (99%) of 2-methyl-5-(2,2,2-trifluoro-1-triethylsilanyloxy-1-trifluoromethyl-ethyl)-2,3-dihydro-1H-indole, red liquid, MS: 414 (MH$^+$).

51.3
To a solution of 94 mg (0.23 mmol) of 2-methyl-5-(2,2,2-trifluoro-1-triethylsilanyloxy-1-trifluoromethyl-ethyl)-2,3- dihydro-1H-indole in 0.5 mL of DMF were added 104 mg (0.45 mmol) of 3-chloromethyl-benzoic acid methyl ester and the mixture was stirred at 80° C. for 10 hrs. After cooling to RT the mixture was treated with 0.5 mL of a 1M solution of TBAF in THF and stirred for an hour at 60° C. Evaporation of the solvent and chromatography on silica gel with EtOAc/n-heptane gave 58 mg (99%) of 3-[2-methyl-5-(2,2,2-trifluoro-1-hydroxy-1-trifluoromethyl-ethyl)-2,3-dihydro-indol-1-yl-methyl]-benzoic acid methyl ester, light red oil, MS: 448 ($MH^+$).

Example 52

1,1,1,3,3,3-hexafluoro-2-{1-[2-(2-fluoro-phenyl)-5-methyl-oxazol-4-ylmethyl]-2-methyl-2,3-dihydro-1H-indol-5-yl}-propan-2-ol 52.1
2-(2-fluoro-phenyl)-4-chloromethyl-5-methyl-oxazole was prepared from 1-fluoro-benzaldehyde in analogy to the procedure by Binggeli et al. (WO200292084).

52.2
In analogy to example 51.3, from 2-methyl-5-(2,2,2-trifluoro-1-triethylsilanyloxy-1-trifluoromethyl-ethyl)-2,3-dihydro-1H-indole (example 51.2) and 2-(2-fluoro-phenyl)-4-chloromethyl-5-methyl-oxazole was prepared 1,1,1,3,3,3-hexafluoro-2-{1-[2-(2-fluoro-phenyl)-5-methyl-oxazol-4-ylmethyl]-2-methyl-2,3-dihydro-1H-indol-5-yl}-propan-2-ol, light yellow oil, MS: 487 $(M-H)^-$.

Example 53

2-{1-[2-(3-chloro-phenyl)-5-methyl-oxazol-4-ylmethyl]-2-methyl-2,3-dihydro-1H-indol-5-yl}-1,1,1,3,3,3-hexafluoro-propan-2-ol 53.1
4-chloromethyl-2-(3-chloro-phenyl)-5-methyl-oxazole was prepared from 3-chloro-benzaldehyde in analogy to the procedure by Binggeli et al. (WO200292084).

53.2
In analogy to example 51.3, from 2-methyl-5-(2,2,2-trifluoro-1-triethylsilanyloxy-1-trifluoromethyl-ethyl)-2,3-dihydro-1H-indole (example 51.2) and 4-chloromethyl-2-(3-chloro-phenyl)-5-methyl-oxazole was prepared 2-{1-[2-(3-chloro-phenyl)-5-methyl-oxazol-4-ylmethyl]-2-methyl-2,3-dihydro-1H-indol-5-yl}-1,1,1,3,3,3-hexafluoro-propan-2-ol, light yellow solid, MS: 505 ($MH^+$), 1Cl.

Example 54

1,1,1,3,3,3-hexafluoro-2-{1-[2-(4-fluoro-3-methyl-phenyl)-5-methyl-oxazol-4-ylmethyl]-2-methyl-2,3-dihydro-1H-indol-5-yl}-propan-2-ol 54.1
2-(4-fluoro-3-methyl-phenyl)-4-chloromethyl-5-methyl-oxazole was prepared from 4-fluoro-3-methyl-benzaldehyde in analogy to the procedure by Binggeli et al. (WO200292084).

54.2
In analogy to example 51.3 from 2-methyl-5-(2,2,2-trifluoro-1-triethylsilanyloxy-1-trifluoromethyl-ethyl)-2,3-dihydro-1H-indole (example 51.2) and 2-(4-fluoro-3-methyl-phenyl)-4-chloromethyl-5-methyl-oxazole was prepared 1,1,1,3,3,3-hexafluoro-2-{1-[2-(4-fluoro-3-methyl-phenyl)-5-methyl-oxazol-4-ylmethyl]-2-methyl-2,3-dihydro-1H-indol-5-yl}-propan-2-ol, light yellow solid, MS: 501 $(M-H)^-$.

Example 55

1,1,1,3,3,3-hexafluoro-2-(2-methyl-1-phenethyl-2,3-dihydro-1H-indol-5-yl)-propan-2-ol A solution of 101 mg (0.24 mmol) of 2-methyl-5-(2,2,2-trifluoro-1-triethylsilanyloxy-1-trifluoromethyl-ethyl)-2,3-dihydro-1H-indole (example 51.2) in $CH_2Cl_2$ was treated with 0.05 mL (0.3 mmol) of DIPEA and then with 0.03 mL (0.24 mmol) of phenylacetylbromide at 0° C. The mixture was stirred at RT for 3 hrs and then distributed between $Et_2O$ a saturated aqueous solution of $NH_4Cl$. The combined organic phases were dried over $Na_2SO_4$ and evaporated to yield 120 mg of 1-[2-methyl-5-(2,2,2-trifluoro-1-triethylsilanyloxy-1-trifluoromethyl-ethyl)-2,3-dihydro-indol-1-yl]-2-phenyl-ethanone. This crude was dissolved in 2 mL of THF and treated with 0.9 mL of a 1M $BH_3$ solution in THF. After stirring for 10 hrs at RT the mixture was distributed between $Et_2O$ and a saturated aqueous solution of $NH_4Cl$. The combined organic phases were dried over $Na_2SO_4$ and evaporated to yield 135 mg of 2-methyl-1-phenethyl-5-(2,2,2-trifluoro-1-triethylsilanyloxy-1-trifluoromethyl-ethyl)-2,3-dihydro-1H-indole, of which 30 mg were dissolved in 1 mL of THF and treated with 0.07 mL of 1M TBAF in THF. Stirring for 30 min, evaporation, and column chromatography on silica gel with n-heptane/EtOAc (4:1) yielded 12 mg (51%) of 1,1,1,3,3,3-hexafluoro-2-(2-methyl-1-phenethyl-2,3-dihydro-1H-indol-5-yl)-propan-2-ol, colorless waxy solid, MS: 404 ($MH^+$).

Example 56

1,1,1,3,3,3-hexafluoro-2-{2-methyl-1-[5-methyl-2-(3-trifluoromethyl-phenyl)-oxazol-4-ylmethyl]-2,3-dihydro-1H-indol-5-yl}-propan-2-ol 56.1
2-(3-trifluormethyl-phenyl)-4-chloromethyl-5-methyl-oxazole was prepared from 3-trifluoromethyl-benzaldehyde in analogy to the procedure by Binggeli et al. (WO200292084).

56.2
In analogy to example 51.3, from 2-methyl-5-(2,2,2-trifluoro-1-triethylsilanyloxy-1-trifluoromethyl-ethyl)-2,3-dihydro-1H-indole (example 51.2) and 2-(3-trifluormethyl-phenyl)-4-chloromethyl-5-methyl-oxazole was prepared 1,1,1,3,3,3-hexafluoro-2-{2-methyl-1-[5-methyl-2-(3-trifluoromethyl-phenyl)-oxazol-4-ylmethyl]-2,3-dihydro-1H-indol-5-yl}-propan-2-ol, yellow oil, MS: 537 $(M-H)^-$.

Example 57

1,1,1,3,3,3-hexafluoro-2-[2-methyl-1-(5-methyl-2-phenyl-oxazol-4-ylmethyl)-2,3-dihydro-1H-indol-5-yl]-propan-2-ol 57.1
4-chloromethyl-5-methyl-2-phenyl-oxazole was prepared from benzaldehyde in analogy to the procedure by Binggeli et al. (WO200292084).

57.2

In analogy to example 51.3, from 2-methyl-5-(2,2,2-trifluoro-1-triethylsilanyloxy-1-trifluoromethyl-ethyl)-2,3-dihydro-1H-indole (example 51.2) and 4-chloromethyl-5-methyl-2-phenyl-oxazole was prepared 1,1,1,3,3,3-hexafluoro-2-[2-methyl-1-(5-methyl-2-phenyl-oxazol-4-ylmethyl)-2,3-dihydro-1H-indol-5-yl]-propan-2-ol, yellowish solid, MS: 471 (MH$^+$).

Example 58

1,1,1,3,3,3-hexafluoro-2-[2-methyl-1-(2-trifluoromethyl-quinolin-6-ylmethyl)-2,3-dihydro-1H-indol-5-yl]-propan-2-ol In analogy to example 51.3, from 2-methyl-5-(2,2,2-trifluoro-1-triethylsilanyloxy-1-trifluoromethyl-ethyl)-2,3-dihydro-1H-indole (example 51.2) and 6-chloromethyl-2-trifluoromethyl-quinoline was prepared 1,1,1,3,3,3-hexafluoro-2-[2-methyl-1-(2-trifluoromethyl-quinolin-6-ylmethyl)-2,3-dihydro-1H-indol-5-yl]-propan-2-ol, light red oil, MS: 509 (MH$^+$).

Example 59

1,1,1,3,3,3-hexafluoro-2-{2-methyl-1-[5-methyl-2-(4-trifluoromethyl-phenyl)-oxazol-4-ylmethyl]-2,3-dihydro-1H-indol-5-yl}-propan-2-ol 59.1

2-(4-trifluormethyl-phenyl)-4-chloromethyl-5-methyl-oxazole was prepared from 4-trifluoromethyl-benzaldehyde in analogy to the procedure by Binggeli et al. (WO200292084).

59.2

In analogy to example 51.3, from 2-methyl-5-(2,2,2-trifluoro-1-triethylsilanyloxy-1-trifluoromethyl-ethyl)-2,3-dihydro-1H-indole (example 51.2) and 2-(4-trifluormethyl-phenyl)-4-chloromethyl-5-methyl-oxazole was prepared 1,1,1,3,3,3-hexafluoro-2-{2-methyl-1-[5-methyl-2-(4-trifluoromethyl-phenyl)-oxazol-4-ylmethyl]-2,3-dihydro-1H-indol-5-yl}-propan-2-ol, yellow semisolid, MS: 537 (M−H)$^-$.

Example 60

1,1,1,3,3,3-hexafluoro-2-(2-methyl-1-naphthalen-1-ylmethyl-2,3-dihydro-1H-indol-5-yl)-propan-2-ol In analogy to example 51.3, from 2-methyl-5-(2,2,2-trifluoro-1-triethylsilanyloxy-1-trifluoromethyl-ethyl)-2,3-dihydro-1H-indole (example 51.2) and 1-chloromethyl-naphthalene was prepared 1,1,1,3,3,3-hexafluoro-2-(2-methyl-1-naphthalen-1-ylmethyl-2,3-dihydro-1H-indol-5-yl)-propan-2-ol, light brown solid, MS: 440 (MH$^+$).

Example 61

[2-methyl-5-(2,2,2-trifluoro-1-hydroxy-1-trifluoromethyl-ethyl)-2,3-dihydro-indol-1-yl]-phenyl-acetic acid methyl ester A solution of 0.14 g (0.34 mmol) 2-methyl-5-(2,2,2-trifluoro-1-triethylsilanyloxy-1-trifluoromethyl-ethyl)-2,3-dihydro-1H-indole (example 51.2) in 1.5 mL of methanol was treated with 0.028 g (0.34 mmol) of sodium acetate and 0.053 mL (0.34 mmol) of α-bromophenyl methyl acetate. The mixture was stirred at 100° C. in a pressure tube for 10 hrs and then distributed between Et$_2$O and a saturated aqueous solution of NH$_4$Cl. The combined organic phases were dried over Na$_2$SO$_4$ and evaporated. Column chromatography on silica gel with n-heptane/EtOAc 4:1 yielded 170 mg of [2-methyl-5-(2,2,2-trifluoro-1-hydroxy-1-trifluoromethyl-ethyl)-2,3-dihydro-indol-1-yl]-phenyl-acetic acid methyl ester, colourless viscous oil, MS: 448 (MH$^+$).

Example 62

2-{1-[2-(4-chloro-phenyl)-5-methyl-oxazol-4-ylmethyl]-2-methyl-2,3-dihydro-1H-indol-5-yl}-1,1,1,3,3,3-hexafluoro-propan-2-ol 62.1

4-chloromethyl-2-(4-chloro-phenyl)-5-methyl-oxazole was prepared from 4-chloro-benzaldehyde in analogy to the procedure by Binggeli et al. (WO200292084).

62.2

In analogy to example 51.3, from 2-methyl-5-(2,2,2-trifluoro-1-triethylsilanyloxy-1-trifluoromethyl-ethyl)-2,3-dihydro-1H-indole (example 51.2) and 4-chloromethyl-2-(4-chloro-phenyl)-5-methyl-oxazole was prepared 2-{1-[2-(4-chloro-phenyl)-5-methyl-oxazol-4-ylmethyl]-2-methyl-2,3-dihydro-1H-indol-5-yl}-1,1,1,3,3,3-hexafluoro-propan-2-ol, light yellow solid, MS: 505 (MH$^+$).

Example 63

1,1,1,3,3,3-hexafluoro-2-(2-methyl-1-quinolin-2-ylmethyl-2,3-dihydro-1H-indol-5-yl)-propan-2-ol In analogy to example 51.3, from 2-methyl-5-(2,2,2-trifluoro-1-triethylsilanyloxy-1-trifluoromethyl-ethyl)-2,3-dihydro-1H-indole (example 51.2) and 2-chloromethyl-quinoline was prepared 1,1,1,3,3,3-hexafluoro-2-(2-methyl-1-quinolin-2-ylmethyl-2,3-dihydro-1H-indol-5-yl)-propan-2-ol, yellow semisolid, MS: 441 (MH$^+$).

Example 64

2-(1-biphenyl-3-ylmethyl-2-methyl-2,3-dihydro-1H-indol-5-yl)-1,1,1,3,3,3-hexafluoro-propan-2-ol In analogy to example 51.3, from 2-methyl-5-(2,2,2-trifluoro-1-triethylsilanyloxy-1-trifluoromethyl-ethyl)-2,3-dihydro-1H-indole (example 51.2) and 3-chloromethyl-biphenyl was prepared 2-(1-biphenyl-3-ylmethyl-2-methyl-2,3-dihydro-1H-indol-5-yl)-1,1,1,3,3,3-hexafluoro-propan-2-ol, brown oil, MS: 466 (MH$^+$).

Example 65

1,1,1,3,3,3-hexafluoro-2-{2-methyl-1-[4-(4-trifluoromethyl-phenoxy)-benzyl]-2,3-dihydro-1H-indol-5-yl}-propan-2-ol 65.1

4-chloromethyl-(4-trifluoromethyl-phenoxy)-benzene was prepared in analogy to a procedure described for the preparation of 4-chloromethyl-phenoxybenzene by Binggeli et al. (WO9701931 1).

65.2

In analogy to example 51.3, from 2-methyl-5-(2,2,2-trifluoro-1-triethylsilanyloxy-1-trifluoromethyl-ethyl)-2,3-dihydro-1H-indole (example 51.2) and 4-chloromethyl-(4-trifluoromethyl-phenoxy)-benzene was prepared 1,1,1,3,3,3-hexafluoro-2-{2-methyl-1-[4-(4-trifluoromethyl-phenoxy)-benzyl]-2,3-dihydro-1H-indol-5-yl}-propan-2-ol, light brown oil, MS: 550 (MH$^+$).

Example 66

2-{1-[2-(4-tert-butyl-phenyl)-5-methyl-oxazol-4-ylmethyl]-2-methyl-2,3-dihydro-1H-indol-5-yl}-1,1,1,3,3,3-hexafluoro-propan-2-ol 66.1

2-(4-tert-butyl-phenyl)-4-chloromethyl-5-methyl-oxazole was prepared from 4-tert-butyl-1-benzaldehyde in analogy to the procedure by Binggeli et al. (WO200292084).

66.2

In analogy to example 51.3, from 2-methyl-5-(2,2,2-trifluoro-1-triethylsilanyloxy-1-trifluoromethyl-ethyl)-2,3-dihydro-1H-indole (example 51.2) and 2-(4-tert-butyl-phenyl)-4-chloromethyl-5-methyl-oxazole was prepared 2-{1-[2-(4-tert-butyl-phenyl)-5-methyl-oxazol-4-ylmethyl]-2-methyl-2,3-dihydro-1H-indol-5-yl}-1,1,1,3,3,3-hexafluoro-propan-2-ol, red solid, MS: 527 (MH$^+$).

Example 67

2-(1-benzhydryl-2-methyl-2,3-dihydro-1H-indol-5-yl)-1,1,1,3,3,3-hexafluoro-propan-2-ol In analogy to example 51.3, from 2-methyl-5-(2,2,2-trifluoro-1-triethylsilanyloxy-1-trifluoromethyl-ethyl)-2,3-dihydro-1H-indole (example 51.2) and diphenylmethylbromide was prepared 2-(1-benzhydryl-2-methyl-2,3-dihydro-1H-indol-5-yl)-1,1,1,3,3,3-hexafluoro-propan-2-ol, yellow oil, MS: 466 (MH$^+$).

Example 68

3-[2-methyl-5-(2,2,2-trifluoro-1-hydroxy-1-trifluoromethyl-ethyl)-2,3-dihydro-indol-1-ylmethyl]-benzoic acid A solution of 66 mg (0.118 mmol) of 3-[2-methyl-5-(2,2,2-trifluoro-1-hydroxy-1-trifluoromethyl-ethyl)-2,3-dihydro-indol-1-ylmethyl]-benzoic acid methyl ester (example 61) in 0.5 mL of THF was treated with 0.2 mL of a 1M aqueous LiOH solution and stirred for 10 hrs at RT. The solvents were evaporated and the residue distributed between EtOAc and a aqueous solution of NH$_4$Cl. Drying of the combined organic phases over Na$_2$SO$_4$ and evaporation of the solvent yielded 51 mg (99%) of 3-[2-methyl-5-(2,2,2-trifluoro-1-hydroxy-1-trifluoromethyl-ethyl)-2,3-dihydro-indol-1-ylmethyl]-benzoic acid, light yellow gum, MS: 432 (M−H)$^-$.

Example 69

4-[2-methyl-5-(2,2,2-trifluoro-1-hydroxy-1-trifluoromethyl-ethyl)-2,3-dihydro-indol-1-ylmethyl]-benzoic acid methyl ester In analogy to example 51.3, from 2-methyl-5-(2,2,2-trifluoro-1-triethylsilanyloxy-1-trifluoromethyl-ethyl)-2,3-dihydro-1H-indole (example 51.2) and 4-chloromethyl-benzoic acid methyl ester was prepared 4-[2-methyl-5-(2,2,2-trifluoro-1-hydroxy-1-trifluoromethyl-ethyl)-2,3-dihydro-indol-1-ylmethyl]-benzoic acid methyl ester, light red oil, MS: 448 (MH$^+$).

Example 70

1,1,1,3,3,3-hexafluoro-2-[1-(2-hydroxy-1-phenyl-ethyl)-2-methyl-2,3-dihydro-1H-indol-5-yl]-propan-2-ol 70.1

To a solution of 114 mg (0.275 mmol) of 2-methyl-5-(2,2,2-trifluoro-1-triethylsilanyloxy-1-trifluoromethyl-ethyl)-2,3-dihydro-1H-indole (example 51.2) in 1 mL of acetonitrile were added 0.063 mL (0.55 mmol) of racemic phenyloxirane and 58 mg (55 mmol) of lithiumperchlorate. After stirring at 80° C. for 18 hrs, the mixture was distributed between Et$_2$O and a saturated aqueous solution of NH$_4$Cl. The combined organic phases were dried over Na$_2$SO$_4$ and evaporated. Column chromatography on silica gel with n-heptane/EtOAc 4:1 yielded 77 mg (52%) of 2-[2-methyl-5-(2,2,2-trifluoro-1-triethylsilanyloxy-1-trifluoromethyl-ethyl)-2,3-dihydro-indol-1-yl]-2-phenyl-ethanol, MS: 534 (MH$^+$).

70.2

To a solution of 19 mg (0.036 mmol) of 2-[2-methyl-5-(2,2,2-trifluoro-1-triethylsilanyloxy-1-trifluoromethyl-ethyl)-2,3-dihydro-indol-1-yl]-2-phenyl-ethanol in 0.5 mL THF were added 0.043 mL (0.043 mmol) of a 1M TBAF solution in THF. After stirring at RT for 24 hrs the mixture was distributed between Et$_2$O and a saturated aqueous solution of NH$_4$Cl. The combined organic phases were dried over Na$_2$SO$_4$ and evaporated. Column chromatography on silica gel with n-heptane/EtOAc 2:1 yielded 9.3 mg (62%) of 1,1,1,3,3,3-hexafluoro-2-[1-(2-hydroxy-1-phenyl-ethyl)-2-methyl-2,3-dihydro-1H-indol-5-yl]-propan-2-ol, yellow viscous oil, MS: 420 (MH$^+$).

Example 71

2-{1-[2-(4-chloro-phenyl)-5-methyl-thiazol-4-ylmethyl]-2-methyl-2,3-dihydro-1H-indol-5-yl}-1,1,1,3,3,3-hexafluoro-propan-2-ol 71.1

4-chloromethyl-2-(4-chloro-phenyl)-5-methyl-thiazole was prepared according to the procedure described by Yamane et al. (Tet.Lett., 45, 2004, 69-74 and WO2001019805).

71.2

In analogy to example 51.3, from 2-methyl-5-(2,2,2-trifluoro-1-triethylsilanyloxy-1-trifluoromethyl-ethyl)-2,3-dihydro-1H-indole (example 51.2) and 4-chloromethyl-2-(4-chloro-phenyl)-5-methyl-thiazole was prepared 2-{1-[2-(4-chloro-phenyl)-5-methyl-thiazol-4-ylmethyl]-2-methyl-2,3-dihydro-1H-indol-5-yl}-1,1,1,3,3,3-hexafluoro-propan-2-ol, yellow oil, MS: 519 ((M−H$^-$), 1Cl).

Example 72

1,1,1,3,3,3-hexafluoro-2-{1-[3-(4-fluoro-phenoxy)-benzyl]-2-methyl-2,3-dihydro-1H-indol-5-yl}-propan-2-ol 72.1
4-chloromethyl-(4-fluoro-phenoxy)-benzene was prepared in analogy to a procedure described for the preparation of 4-chloromethyl-phenoxybenzene by Binggeli et al. (WO97019311).

72.2
In analogy to example 51.3, from 2-methyl-5-(2,2,2-trifluoro-1-triethylsilanyloxy-1-trifluoromethyl-ethyl)-2,3-dihydro-1H-indole (example 51.2) and chloromethyl-3-(4-fluoro-phenoxy)-benzene was prepared 1,1,1,3,3,3-hexafluoro-2-{1-[3-(4-fluoro-phenoxy)-benzyl]-2-methyl-2,3-dihydro-1H-indol-5-yl}-propan-2-ol, light red oil, MS: 500 (MH$^+$).

Example 73

1,1,1,3,3,3-hexafluoro-2-{1-[2-(4-isopropoxy-phenyl)-5-methyl-oxazol-4-ylmethyl]-2-methyl-2,3-dihydro-1H-indol-5-yl}-propan-2-ol 73.1
2-(4-isopropoxy-phenyl)-4-chloromethyl-5-methyl-oxazole was prepared from 4-isopropoxy-benzaldehyde in analogy to the procedure by Binggeli et al. (WO200292084).

73.2
In analogy to example 51.3, from 2-methyl-5-(2,2,2-trifluoro-1-triethylsilanyloxy-1-trifluoromethyl-ethyl)-2,3-dihydro-1H-indole (example 51.2) and 2-(4-isopropoxy-phenyl)-4-chloromethyl-5-methyl-oxazole was prepared 1,1,1,3,3,3-hexafluoro-2-{1-[2-(4-isopropoxy-phenyl)-5-methyl-oxazol-4-ylmethyl]-2-methyl-2,3-dihydro-1H-indol-5-yl}-propan-2-ol, light yellow oil, MS: 527 (M–H)$^-$.

Example 74

1,1,1,3,3,3-hexafluoro-2-{2-methyl-1-[2-methyl-6-(4-trifluoromethyl-phenyl)-pyridin-3-ylmethyl]-2,3-dihydro-1H-indol-5-yl}-propan-2-ol In analogy to example 51.3, from 2-methyl-5-(2,2,2-trifluoro-1-triethylsilanyloxy-1-trifluoromethyl-ethyl)-2,3-dihydro-1H-indole (example 51.2) and 3-chloromethyl-2-methyl-6-(4-trifluoromethyl-phenyl)-pyridine was prepared 1,1,1,3,3,3-hexafluoro-2-{2-methyl-1-[2-methyl-6-(4-trifluoromethyl-phenyl)-pyridin-3-ylmethyl]-2,3-dihydro-1H-indol-5-yl}-propan-2-ol, light yellow solid, MS: 549 (MH$^+$).

Example 75

2-{1-[2-(2,5-diphenyl-oxazol-4-yl)-ethyl]-2-methyl-2,3-dihydro-1H-indol-5-yl}-1,1,1,3,3,3-hexafluoro-propan-2-ol 75.1
In analogy to example 85.1, from benzaldehyde and 1-phenyl-1,2-propanedione 2-oxime instead of diacetylmonooxyme was prepared 2-(2,5-diphenyl-oxazol-4-yl)-ethanol. Transformation of 2-(2,5-diphenyl-oxazol-4-yl) ethanol to 4-(2-bromo-ethyl)-2,5-diphenyl-oxazole was carried out by O-mesylation followed by treatment with NaBr, in analogy to the procedure by Faul et al. (Heterocycles, 2001, 55(4) 689-704).

75.2
A solution of 100 mg (0.33 mmol) of 1,1,1,3,3,3-hexafluoro-2-(2-methyl-2,3-dihydro-1H-indol-5-yl)-propan-2-ol (example 51.1) and 4-(2-bromo-ethyl)-2,5-diphenyl-oxazole in 0.5 mL of DMF was stirred at 80° C. overnight. Distribution of the mixture between a saturated aqueous solution of NH$_4$Cl and Et$_2$O, drying of the combined organic phases over Na$_2$SO$_4$ and column chromatography on silica gel with n-heptane/EtOAc 4:1 yielded 39 mg (21%) of 2-{1-[2-(2,5-diphenyl-oxazol-4-yl)-ethyl]-2-methyl-2,3-dihydro-1H-indol-5-yl}-1,1,1,3,3,3-hexafluoro-propan-2-ol, light yellow gum, MS: 547 (MH$^+$).

Example 76

1,1,1,3,3,3-hexafluoro-2-{1-[2-(4-isopropyl-phenyl)-5-methyl-oxazol-4-ylmethyl]-2-methyl-2,3-dihydro-1H-indol-5-yl}-propan-2-ol 76.1
4-chloromethyl-2-(4-isopropyl-phenyl)-5-methyl-oxazole was prepared from 4-isopropyl-benzaldehyde in analogy to the procedure by Binggeli et al. (WO200292084).

76.2
In analogy to example 75, from 1,1,1,3,3,3-hexafluoro-2-(2-methyl-2,3-dihydro-1H-indol-5-yl)-propan-2-ol (example 51.1) and 4-chloromethyl-2-(4-isopropyl-phenyl)-5-methyl-oxazole was prepared 1,1,1,3,3,3-hexafluoro-2-{1-[2-(4-isopropyl-phenyl)-5-methyl-oxazol-4-ylmethyl]-2-methyl-2,3-dihydro-1H-indol-5-yl}-propan-2-ol, orange oil, MS: 513 (MH$^+$).

Example 77

1,1,1,3,3,3-hexafluoro-2-{1-[2-(2-methoxy-phenyl)-5-methyl-oxazol-4-ylmethyl]-2-methyl-2,3-dihydro-1H-indol-5-yl}-propan-2-ol 77.1
4-chloromethyl-2-(2-methoxy-phenyl)-5-methyl-oxazole was prepared from 2-methoxy-benzaldehyde in analogy to the procedure by Binggeli et al. (WO200292084).

77.2
In analogy to example 75, from 1,1,1,3,3,3-hexafluoro-2-(2-methyl-2,3-dihydro-1H-indol-5-yl)-propan-2-ol (example 51.1) and 4-chloromethyl-2-(2-methoxy-phenyl)-5-methyl-oxazole was prepared 1,1,1,3,3,3-hexafluoro-2-{1-[2-(2-methoxy-phenyl)-5-methyl-oxazol-4-ylmethyl]-2-methyl-2,3-dihydro-1H-indol-5-yl}-propan-2-ol, light yellow gum, MS: 501 (MH$^+$).

Example 78

1,1,1,3,3,3-hexafluoro-2-{2-methyl-1-[5-methyl-2-(2-trifluoromethyl-phenyl)-oxazol-4-ylmethyl]-2,3-dihydro-1H-indol-5-yl}-propan-2-ol 78.1
4-chloromethyl-2-(2-trifluoromethyl-phenyl)-5-methyl-oxazole was prepared from 2-trifluoromethyl-benzaldehyde in analogy to the procedure by Binggeli et al. (WO200292084).

78.2

In analogy to example 75, from 1,1,1,3,3,3-hexafluoro-2-(2-methyl-2,3-dihydro-1H-indol-5-yl)-propan-2-ol (example 51.1) and 4-chloromethyl-2-(2-trifluoromethyl-phenyl)-5-methyl-oxazole was prepared 1,1,1,3,3,3-hexafluoro-2-{2-methyl-1-[5-methyl-2-(2-trifluoromethyl-phenyl)-oxazol-4-ylmethyl]-2,3-dihydro-1H-indol-5-yl}-propan-2-ol, light yellow gum, MS: 539 (MH$^+$).

Example 79

2-{1-[2-(4-benzyloxy-phenyl)-5-methyl-oxazol-4-ylmethyl]-2-methyl-2,3-dihydro-1H-indol-5-yl}-1,1,1,3,3,3-hexafluoro-propan-2-ol 79.1

4-chloromethyl-2-(4-benzyloxy-phenyl)-5-methyl-oxazole was prepared from 4-benzyloxy-benzaldehyde in analogy to the procedure by Binggeli et al. (WO200292084).

79.2

In analogy to example 75, from 1,1,1,3,3,3-hexafluoro-2-(2-methyl-2,3-dihydro-1H-indol-5-yl)-propan-2-ol (example 51.1) and 4-chloromethyl-2-(4-benzyloxy-phenyl)-5-methyl-oxazole was prepared 1,1,1,3,3,3-hexafluoro-2-{1-[2-(4-benzyloxy-phenyl)-5-methyl-oxazol-4-ylmethyl]-2-methyl-2,3-dihydro-1H-indol-5-yl}-propan-2-ol, light brown foam, MS: 577 (MH$^+$).

Example 80

2-(1-benzyl-2-methyl-1H-indol-5-yl)-1,1,1,3,3,3-hexafluoro-propan-2-ol

A solution of 31 mg (0.055 mmol) of 2-(1-benzyl-2-triisopropylsilanyloxymethyl-1H-indol-5-yl)-1,1,1,3,3,3-hexafluoro-propan-2-ol (example 41.3) in 1 mL of methanol was hydrogenated at atmospheric pressure for 12 hours in the presence of 30 mg of Pd/C (10% Pd). Removal of the catalyst by filtration through decalite and evaporation of the solvent yielded 20 mg (93%) of 2-(1-benzyl-2-methyl-1H-indol-5-yl)-1,1,1,3,3,3-hexafluoro-propan-2-ol, red solid, MS: 388 (MH$^+$).

Example 81

1,1,1,3,3,3-hexafluoro-2-{2-methyl-1-[2-methyl-5-(4-trifluoromethyl-phenyl)-2H-pyrazol-3-ylmethyl]-2,3-dihydro-1H-indol-5-yl}-propan-2-ol 81.1

5-chloromethyl-1-methyl-3-(4-trifluoromethyl-phenyl)-1H-pyrazole was prepared in analogy to the preparation of 5-chloromethyl-1-methyl-3-(3,4,5-trimethoxy-phenyl)-1H-pyrazole described by Kodama et al. (U.S. Pat. No. 6,472,386), but starting from 4-trifluoromethylacetophenone instead of 3'4'5'-trimethoxyacetophenone.

81.2

In analogy to example 75, from 1,1,1,3,3,3-hexafluoro-2-(2-methyl-2,3-dihydro-1H-indol-5-yl)-propan-2-ol (example 51.1) and 5-chloromethyl-1-methyl-3-(4-trifluoromethyl-phenyl)-1H-pyrazole was prepared 1,1,1,3,3,3-hexafluoro-2-{2-methyl-1-[2-methyl-5-(4-trifluoromethyl-phenyl)-2H-pyrazol-3-ylmethyl]-2,3-dihydro-1H-indol-5-yl}-propan-2-ol, light yellow solid, MS: 538 (MH$^+$).

Example 82

2-{1-[2-ethyl-5-(4-trifluoromethyl-phenyl)-2H-pyrazol-3-ylmethyl]-2-methyl-2,3-dihydro-1H-indol-5-yl}-1,1,1,3,3,3-hexafluoro-propan-2-ol 82.1

5-chloromethyl-1-ethyl-3-(4-trifluoromethyl-phenyl)-1H-pyrazole was prepared in analogy to the prepaparation of 5-chloromethyl-1-ethyl-3-(3,4,5-trimethoxy-phenyl)-1H-pyrazole described by Kodama et al. (U.S. Pat. No. 6,472,386), but starting from 4-trifluoromethylacetophenone instead of 3'4'5'-trimethoxyacetophenone and using ethyl hydrazine instead of methylhydrazine.

82.2

In analogy to example 75, from 1,1,1,3,3,3-hexafluoro-2-(2-methyl-2,3-dihydro-1H-indol-5-yl)-propan-2-ol (example 51.1) and 5-chloromethyl-1-ethyl-3-(4-trifluoromethyl-phenyl)-1H-pyrazole was prepared 2-{1-[2-ethyl-5-(4-trifluoromethyl-phenyl)-2H-pyrazol-3-ylmethyl]-2-methyl-2,3-dihydro-1H-indol-5-yl}-1,1,1,3,3,3-hexafluoro-propan-2-ol, yellow oil, MS: 552 (MH$^+$).

Example 83

(4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetic acid methyl ester A solution of 40 mg (0.083 mmol) of 4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenol (example 99) in 0.5 mL of DMF was treated with 0.01 mL of DBU and 0.01 mL (0.1 mmol) of methylbromoacetate. The mixture was stirred overnight at RT and distributed between Et$_2$O and a saturated aqueous solution of NH$_4$Cl. Drying of the combined organic phases, evaporation of the solvent and chromatography on silica gel with n-heptane/EtOAc 1:1 gave (4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetic acid methyl ester, off-white foam, MS: 559 (MH$^+$).

Example 84

(4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetic acid In analogy to example 91, from (4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetic acid methyl ester (example 83) was prepared (4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetic acid, light yellow solid, MS: (545, MH$^+$).

Example 85

1,1,1,3,3,3-hexafluoro-2-{2-methyl-1-[2-(2-methyl-5-phenyl-oxazol-4-yl)-ethyl]-2,3-dihydro-1H-indol-5-yl}-propan-2-ol 1,1,1,3,3,3-hexafluoro-2-{2-methyl-1-[2-(5-methyl-2-phenyl-oxazol-4-yl)-ethyl]-2,3-dihydro-1H-indol-5-yl}-propan-2-ol 85.1

2-(5-methyl-2-phenyl-oxazol-4-yl)-ethanol was obtained from benzaldehyde and diacetylmonooxime in analogy to the procedure by Binggeli et al. (WO200292084). Transformation of 2-(2,5-diphenyl-oxazol-4-yl)-ethanol to 4-(2-bromo-ethyl)-2,5-diphenyl-oxazole was carried by O-mesylation followed by treatment with NaBr in analogy the procedure by Faul et al. (Heterocycles, 2001, 55(4), 689-704).

85.2

In analogy to example 75, from 1,1,1,3,3,3-hexafluoro-2-(2-methyl-2,3-dihydro-1H-indol-5-yl)-propan-2-ol (example 51.1) and 4-(2-bromo-ethyl)-5-methyl-2-phenyl-oxazole was prepared 1,1,1,3,3,3-Hexafluoro-2-{2-methyl-1-[2-(2-methyl-5-phenyl-oxazol-4-yl)-ethyl]-2,3-dihydro-1H-indol-5-yl}-propan-2-ol, MS: 485 (MH$^+$).

Example 86

1,1,1,3,3,3-hexafluoro-2-{2-methyl-1-[4-methyl-2-(4-trifluoromethyl-phenyl)-oxazol-5-ylmethyl]-2,3-dihydro-1H-indol-5-yl}-propan-2-ol 86.1

5-chloromethyl-4-methyl-2-(4-trifluoromethyl-phenyl)-oxazole was prepared in analogy to a procedure by Sznaidman et al. (Bioorg. Med. Chem. Letters, 2003, 13(9) 1517-1521 and WO2001000603).

86.2

In analogy to example 75, from 1,1,1,3,3,3-hexafluoro-2-(2-methyl-2,3-dihydro-1H-indol-5-yl)-propan-2-ol (example 51.1) and 5-chloromethyl-4-methyl-2-(4-trifluoromethyl-phenyl)-oxazole was prepared 1,1,1,3,3,3-hexafluoro-2-{2-methyl-1-[4-methyl-2-(4-trifluoromethyl-phenyl)-oxazol-5-ylmethyl]-2,3-dihydro-1H-indol-5-yl}-propan-2-ol, light yellow solid, MS: 539 (MH$^+$).

Example 87

N,N-dimethyl-2-(4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetamide In analogy to example 34, from (4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetic acid (example 84) and dimethylamine hydrochloride was prepared N,N-dimethyl-2-(4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetamide, white foam, MS: 572 (MH$^+$).

Example 88

2-{1-[2-(3-benzyloxy-phenyl)-5-methyl-oxazol-4-ylmethyl]-2-methyl-2,3-dihydro-1H-indol-5-yl}-1,1,1,3,3,3-hexafluoro-propan-2-ol 88.1

4-chloromethyl-2-(3-benzyloxy-phenyl)-5-methyl-oxazole was prepared from 3-benzyloxy-benzaldehyde in analogy to the procedure by Binggeli et al. (WO200292084).

88.2

In analogy to example 75, from 1,1,1,3,3,3-hexafluoro-2-(2-methyl-2,3-dihydro-1H-indol-5-yl)-propan-2-ol (example 51.1) and 2-(3-benzyloxy-phenyl)-4-chloromethyl-5-methyl-oxazole was prepared 2-{1-[2-(3-benzyloxy-phenyl)-5-methyl-oxazol-4-ylmethyl]-2-methyl-2,3-dihydro-1H-indol-5-yl}-1,1,1,3,3,3-hexafluoro-propan-2-ol, orange solid, MS: 577 (MH$^+$).

Example 89

4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester 89.1

4-(4-chloromethyl-5-methyl-oxazol-2-yl)-benzoic acid methyl ester was prepared from 3-formyl-benzoic acid methyl ester in analogy to the procedure by Binggeli et al. (WO200292084).

89.2

In analogy to example 75, from 1,1,1,3,3,3-hexafluoro-2-(2-methyl-2,3-dihydro-1H-indol-5-yl)-propan-2-ol (example 51.1) and 4-(4-chloromethyl-5-methyl-oxazol-2-yl)-benzoic acid methyl ester was prepared 4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester, yellow gum, MS: 529 (MH$^+$).

Example 90

3-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester 90.1

4-(4-chloromethyl-5-methyl-oxazol-2-yl)-benzoic acid methyl ester was prepared from 3-formyl-benzoic acid methyl ester in analogy to the procedure by Binggeli et al. (WO200292084).

90.2

In analogy to example 75, from 1,1,1,3,3,3-hexafluoro-2-(2-methyl-2,3-dihydro-1H-indol-5-yl)-propan-2-ol (example 51.1) and 3-(4-chloromethyl-5-methyl-oxazol-2-yl)-benzoic acid methyl ester was prepared 3-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester, off-white solid, MS: 529 (MH$^+$).

Example 91

3-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid

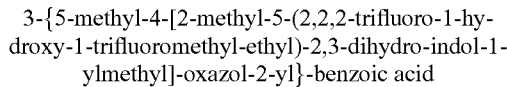

A solution of 50 mg (0.095 mmol) of 3-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester (example 90) was added 1 mL of a 1M aqueous LiOH-solution and the mixture stirred at RT for 1 h. After acidification with aqueous HCl to pH of ca 3-4, $Et_2O$ was added, the phases were separated and the aqueous one extracted with $Et_2O$. The combined organic phases were dried over $Na_2SO_4$ and evaporated to yield 49 mg (quantitative) of 3-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid, off-white solid, MS: 513, (M–H)⁻.

Example 92

4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid

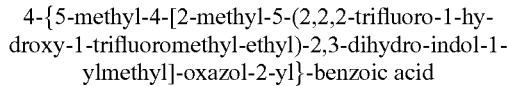

In analogy to example 91, from 4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester (example 89) was prepared 4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid, yellow foam, MS: 513 (M–H).

Example 93

3-{4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester

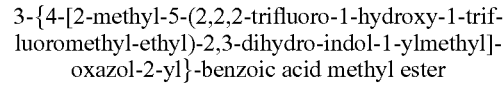

93.1

3-(4-chloromethyl-oxazol-2-yl)-benzoic acid methyl ester was prepared according to the procedure by Adam et al. (WO2002083652).

93.2

In analogy to example 75, from 1,1,1,3,3,3-hexafluoro-2-(2-methyl-2,3-dihydro-1H-indol-5-yl)-propan-2-ol (example 51.1) and 3-(4-chloromethyl-oxazol-2-yl)-benzoic acid methyl ester was prepared 3-{4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester, yellow foam, MS: 515 (MH⁺).

Example 94

2-{1-[2-(2,5-diphenyl-oxazol-4-yl)-ethyl]-2-methyl-1H-indol-5-yl}-1,1,1,3,3,3-hexafluoro-propan-2-ol

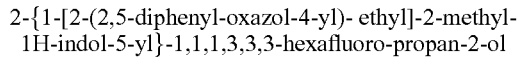

In analogy to example 1, from 2-{1-[2-(2,5-diphenyl-oxazol-4-yl)-ethyl]-2-methyl-2,3-dihydro-1H-indol-5-yl}-1,1,1,3,3,3-hexafluoro-propan-2-ol (example 75) was prepared 2-{1-[2-(2,5-diphenyl-oxazol-4-yl)-ethyl]-2-methyl-1H-indol-5-yl}-1,1,1,3,3,3-hexafluoro-propan-2-ol, off white solid, MS: 545 (MH⁺).

Example 95

1,1,1,3,3,3-hexafluoro-2-{1-[2-(4-isopropyl-phenyl)-5-methyl-oxazol-4-ylmethyl]-2-methyl-1H-indol-5-yl}-propan-2-ol

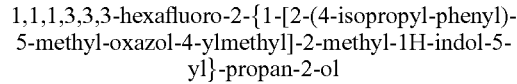

In analogy to example 1, from 1,1,1,3,3,3-hexafluoro-2-{1-[2-(4-isopropyl-phenyl)-5-methyl-oxazol-4-ylmethyl]-2-methyl-2,3-dihydro-1H-indol-5-yl}-propan-2-ol (example 76) was prepared 1,1,1,3,3,3-hexafluoro-2-{1-[2-(4-isopropyl-phenyl)-5-methyl-oxazol-4-ylmethyl]-2-methyl-1H-indol-5-yl}-propan-2-ol, orange foam, MS: 511 (MH⁺).

Example 96

1,1,1,3,3,3-hexafluoro-2-{1-[2-(2-methoxy-phenyl)-5-methyl-oxazol-4-ylmethyl]-2-methyl-1H-indol-5-yl}-propan-2-ol

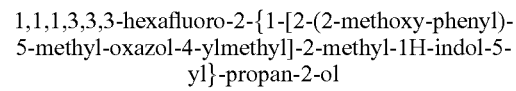

In analogy to example 1, from 1,1,1,3,3,3-hexafluoro-2-{1-[2-(2-methoxy-phenyl)-5-methyl-oxazol-4-ylmethyl]-2-methyl-2,3-dihydro-1H-indol-5-yl}-propan-2-ol (example 77) was prepared 1,1,1,3,3,3-hexafluoro-2-{1-[2-(2-methoxy-phenyl)-5-methyl-oxazol-4-ylmethyl]-2-methyl-1H-indol-5-yl}-propan-2-ol, light yellow solid, MS: 499 (MH⁺).

Example 97

1,1,1,3,3,3-hexafluoro-2-{2-methyl-1-[5-methyl-2-(2-trifluoromethyl-phenyl)-oxazol-4-ylmethyl]-1H-indol-5-yl}-propan-2-ol

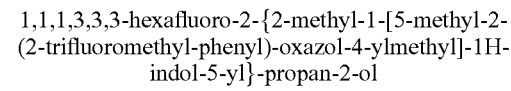

In analogy to example, 1 from 1,1,1,3,3,3-hexafluoro-2-{2-methyl-1-[5-methyl-2-(2-trifluoromethyl-phenyl)-oxazol-4-ylmethyl]-2,3-dihydro-1H-indol-5-yl}-propan-2-ol (example 78) was prepared 1,1,1,3,3,3-hexafluoro-2-{2-methyl-1-[5-methyl-2-(2-trifluoromethyl-phenyl)-oxazol-4-ylmethyl]-1H-indol-5-yl}-propan-2-ol, light yellow gum, MS: 537 (MH⁺).

Example 98

1,1,1,3,3,3-hexafluoro-2-{1-[2-(4-benzyloxy-phenyl)-5-methyl-oxazol-4-ylmethyl]-2-methyl-1H-indol-5-yl}-propan-2-ol

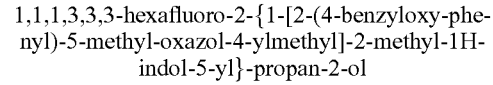

In analogy to example 1, from 1,1,1,3,3,3-hexafluoro-2-{1-[2-(4-benzyloxy-phenyl)-5-methyl-oxazol-4-ylmethyl]-2-methyl-2,3-dihydro-1H-indol-5-yl}-propan-2-ol (example 79) was prepared 1,1,1,3,3,3-hexafluoro-2-{1-[2-(4-benzyloxy-phenyl)-5-methyl-oxazol-4-ylmethyl]-2-methyl-1H-indol-5-yl}-propan-2-ol, light brown foam, MS: 575 (MH⁺).

Example 99

4-{5-methyl-4-[2-methyl-5-(2,2,2-trifluoro-1-hydroxy-1-trifluoromethyl-ethyl)-indol-1-ylmethyl]-oxazol-2-yl}-phenol

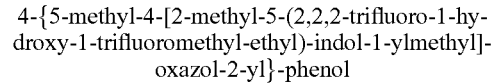

A solution of 80 mg (0.139 mmol) of 2-{1-[2-(4-benzyloxy-phenyl)-5-methyl-oxazol-4-ylmethyl]-2-methyl-1H-indol-5-yl}-1,1,1,3,3,3-hexafluoro-propan-2-ol (example 98) in 1 mL of methanol was treated with 20 mg Pd/C (10% Pd) and stirred under $H_2$ at atmospheric pressure for 6 hrs. Filtration and evaporation of the solvent yielded 59 mg (87%) of 4-{5-methyl-4-[2-methyl-5-(2,2,2-trifluoro-1-hydroxy-1-trifluoromethyl-ethyl)-indol-1-ylmethyl]-oxazol-2-yl}-phenol, light green foam, MS: 485 (MH⁺).

Example 100 dimethyl-carbamic acid 4-{5-methyl-4-[2-methyl-5-(2,2,2-trifluoro-1-hydroxy-1-trifluoromethyl-ethyl)-indol-1-ylmethyl]-oxazol-2-yl}-phenyl ester A solution of 25 mg (0.052 mmol) 4-{5-methyl-4-[2-methyl-5-(2,2,2-trifluoro-1-hydroxy-1-trifluoromethyl-ethyl)-indol-1-ylmethyl]-oxazol-2-yl}-phenol (example 99) in 1 mL of pyridine was treated with 28 mg (0.26 mmol) of dimethyl carbamoylchloride and stirred at 60° C. for 2 hours. Et$_2$O and aqueous HCl were added and the phases separated. The aqueous phase was extracted with Et$_2$O and the combined organic phases dried over Na$_2$SO$_4$. Evaporation of the solvent and column chromatography on silica gel with n-heptane/EtOAc 1:1 yielded 19 mg (66%) of dimethyl-carbamic acid 4-{5-methyl-4-[2-methyl-5-(2,2,2-trifluoro-1-hydroxy-1-trifluoromethyl-ethyl)-indol-1-ylmethyl]-oxazol-2-yl}-phenyl ester, light yellow solid, MS: 556 (MH$^+$).

Example 101

1,1,1,3,3,3-hexafluoro-2-{2-methyl-1-[2-(5-methyl-2-phenyl-oxazol-4-yl)-ethyl]-1H-indol-5-yl}-propan-2-ol In analogy to example 1 from 1,1,1,3,3,3-hexafluoro-2-{2-methyl-1-[2-(2-methyl-5-phenyl-oxazol-4-yl)-ethyl]-2,3-dihydro-1H-indol-5-yl}-propan-2-ol (example 85) was prepared 1,1,1,3,3,3-hexafluoro-2-{2-methyl-1-[2-(5-methyl-2-phenyl-oxazol-4-yl)-ethyl]-1H-indol-5-yl}-propan-2-ol, light yellow solid, MS: 483(MH$^+$).

Example 102

1,1,1,3,3,3-hexafluoro-2-{2-methyl-1-[4-methyl-2-(4-trifluoromethyl-phenyl)-oxazol-5-ylmethyl]-1H-indol-5-yl}-propan-2-ol In analogy to example 1 from 1,1,1,3,3,3-hexafluoro-2-{2-methyl-1-[5-methyl-2-(4-trifluoromethyl-phenyl)-oxazol-4-ylmethyl]-2,3-dihydro-1H-indol-5-yl}-propan-2-ol (example 59) was prepared 1,1,1,3,3,3-hexafluoro-2-{2-methyl-1-[4-methyl-2-(4-trifluoromethyl-phenyl)-oxazol-5-ylmethyl]-1H-indol-5-yl}-propan-2-ol, yellow solid, MS: 535 (M–H)$^-$.

Example 103

2-{1-[2-ethyl-5-(4-trifluoromethyl-phenyl)-2H-pyrazol-3-ylmethyl]-2-methyl-1H-indol-5-yl}1,1,1,3,3,3-hexafluoro-propan-2-ol In analogy to example 1, from 2-{1-[2-ethyl-5-(4-trifluoromethyl-phenyl)-2H-pyrazol-3-ylmethyl]-2-methyl-2,3-dihydro-1H-indol-5-yl}-1,1,1,3,3,3-hexafluoro-propan-2-ol (example 82) was prepared 2-{1-[2-ethyl-5-(4-trifluoromethyl-phenyl)-2H-pyrazol-3-ylmethyl]-2-methyl-1H-indol-5-yl}-1,1,1,3,3,3-hexafluoro-propan-2-ol, light yellow solid, MS: 548 (M–H)$^-$.

Example 104

1,1,1,3,3,3-hexafluoro-2-{2-methyl-1-[2-methyl-5-(4-trifluoromethyl-phenyl)-2H-pyrazol-3-ylmethyl]-1H-indol-5-yl}-propan-2-ol In analogy to example 1,1,1,1,3,3,3-hexafluoro-2-{2-methyl-1-[2-methyl-5-(4-trifluoromethyl-phenyl)-2H-pyrazol-3-ylmethyl]-2,3-dihydro-1H-indol-5-yl}-propan-2-ol (example 81) was prepared 1,1,1,3,3,3-hexafluoro-2-{2-methyl-1-[2-methyl-5-(4-trifluoromethyl-phenyl)-2H-pyrazol-3-ylmethyl]-1H-indol-5-yl}-propan-2-ol, light yellow solid, MS: 534 (M–H)$^-$.

Example 105

(4-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetic acid methyl ester In analogy to example 1, from (4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetic acid methyl ester (example 83) was prepared (4-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetic acid methyl ester, green gum, MS: 557 (MH$^+$).

Example 106

(4-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetic acid In analogy to example 91, from (4-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetic acid methyl ester (example 105) was prepared (4-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetic acid, yellow gum, MS: 543 (MH$^+$).

Example 107

2-{3-chloro-1-[2-(3-chloro-phenyl)-5-methyl-oxazol-4-ylmethyl]-2-methyl-1H-indol-5-yl}-1,1,1,3,3,3-hexafluoro-propan-2-ol In analogy to example 2, from 2-{1-[2-(3-chloro-phenyl)-5-methyl-oxazol-4-ylmethyl]-2-methyl-1H-indol-5-yl}-1,1,1,3,3,3-hexafluoro-propan-2-ol (example 12) was prepared 2-{3-chloro-1-[2-(3-chloro-phenyl)-5-methyl-oxazol-4-ylmethyl]-2-methyl-1H-indol-5-yl}-1,1,1,3,3,3-hexafluoro-propan-2-ol, off-white solid, MS: 537 (MH$^+$), 2Cl.

Example 108 pyrrolidine-1-carboxylic acid 4-{5-methyl-4-[2-methyl-5-(2,2,2-trifluoro-1-hydroxy-1-trifluoromethyl-ethyl)-indol-1-ylmethyl]-oxazol-2-yl}-phenyl ester In analogy to example 100, from 4-{5-methyl-4-[2-methyl-5-(2,2,2-trifluoro-1-hydroxy-1-trifluoromethyl-ethyl)-indol-1-ylmethyl]-oxazol-2-yl}-phenol (example 99) and 1-pyrrolidine-carbonylchloride was prepared pyrrolidine-1-carboxylic acid 4-{5-methyl-4-[2-methyl-5-(2,2,2-trifluoro-1-hydroxy-1-trifluoromethyl-ethyl)-indol-1-ylmethyl]-oxazol-2-yl}-phenyl ester, light yellow solid, MS: 582 (MH$^+$).

Example 109 morpholine-4-carboxylic acid 4-{5-methyl-4-[2-methyl-5-(2,2,2-trifluoro-1-hydroxy-1-trifluoromethyl-ethyl)-indol-1-ylmethyl]-oxazol-2-yl}-phenyl ester In analogy to example 100, from 4-{5-methyl-4-[2-methyl-5-(2,2,2-trifluoro-1-hydroxy-1-trifluoromethyl-ethyl)-indol-1-ylmethyl]-oxazol-2-yl}-phenol (example 99) and morpholine-4-carbonylchloride was prepared morpholine-4-carboxylic acid 4-{5-methyl-4-[2-methyl-5-(2,2,2-trifluoro-1-hydroxy-1-trifluoromethyl-ethyl)-indol-1-ylmethyl]-oxazol-2-yl}-phenyl ester, colorless gum, MS: 598 (MH$^+$).

Example 110

2-(2-chloro-phenyl)-4-[2-methyl-5-(2,2,2-trifluoro-1-hydroxy-1-trifluoromethyl-ethyl)-indol-1-ylmethyl]-oxazole-5-carboxylic acid In analogy to example 91, from 2-(2-chloro-phenyl)-4-[2-methyl-5-(2,2,2-trifluoro-1-hydroxy-1-trifluoromethyl-ethyl)-indol-1-ylmethyl]-oxazole-5-carboxylic acid methyl ester (example 130) was prepared (2-(2-chloro-phenyl)-4-[2-methyl-5-(2,2,2-trifluoro-1-hydroxy-1-trifluoromethyl-ethyl)-indol-1-ylmethyl]-oxazole-5-carboxylic acid, brown solid, MS: 533 (MH$^+$), 1Cl.

Example 111

2-{1-[2-(2-chloro-phenyl)-5-hydroxymethyl-oxazol-4-ylmethyl]-2-methyl-1H-indol-5-yl}-1,1,1,3,3,3-hexafluoro-propan-2-ol At 0° C., a solution of 10 mg (0.018 mmol) of 2-(2-chloro-phenyl)-4-[2-methyl-5-(2,2,2-trifluoro-1-hydroxy-1-trifluoromethyl-ethyl)-indol-1-ylmethyl]-oxazole-5-carboxylic acid methyl ester (example 130) in 0.3 mL of THF was treated with 1 mg (0.026 mmol) of LiAlH$_4$ and stirred at RT for 6 hrs. Ice was added and the mixture distributed between Et$_2$O and water. Drying of the combined organic phases and evaporation yielded 9 mg (95%) of 2-{1-[2-(2-chloro-phenyl)-5-hydroxymethyl-oxazol-4-ylmethyl]-2-methyl-1H-indol-5-yl}-1,1,1,3,3,3-hexafluoro-propan-2-ol, off-white solid, MS:518 (MH$^+$), 1 Cl.

Example 112

N,N-dimethyl-2-(4-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetamide In analogy to example 1, from N,N-dimethyl-2-(4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenoxy)-acetamide (example 87) was prepared N,N-dimethyl-2-(4-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetamide, off white solid, MS: 570 (MH$^+$).

Example 113

2-{1-[2-(3-benzyloxy-phenyl)-5-methyl-oxazol-4-ylmethyl]-2-methyl-1H-indol-5-yl}-1,1,1,3,3,3-hexafluoro-propan-2-ol In analogy to example 1, from 2-{1-[2-(3-benzyloxy-phenyl)-5-methyl-oxazol-4-ylmethyl]-2-methyl-2,3-dihydro-1H-indol-5-yl}-1,1,1,3,3,3-hexafluoro-propan-2-ol (example 88) was prepared 2-{1-[2-(3-benzyloxy-phenyl)-5-methyl-oxazol-4-ylmethyl]-2-methyl-1H-indol-5-yl}-1,1,1,3,3,3-hexafluoro-propan-2-ol, off white solid, MS: 575 (MH$^+$).

Example 114

3-{5-methyl-4-[2-methyl-5-(2,2,2-trifluoro-1-hydroxy-1-trifluoromethyl-ethyl)-indol-1-ylmethyl]-oxazol-2-yl}-phenol In analogy to example 99, from 2-{1-[2-(3-benzyloxy-phenyl)-5-methyl-oxazol-4-ylmethyl]-2-methyl-1H-indol-5-yl}-1,1,1,3,3,3-hexafluoro-propan-2-ol (example 113) was prepared 3-{5-methyl-4-[2-methyl-5-(2,2,2-trifluoro-1-hydroxy-1-trifluoromethyl-ethyl)-indol-1-ylmethyl]-oxazol-2-yl}-phenol, light brown solid, MS: 485 (MH$^+$).

Example 115 morpholine-4-carboxylic acid 3-{5-methyl-4-[2-methyl-5-(2,2,2-trifluoro-1-hydroxy-1-trifluoromethyl-ethyl)-indol-1-ylmethyl]-oxazol-2-yl}-phenyl ester In analogy to example 100, from 3-{5-methyl-4-[2-methyl-5-(2,2,2-trifluoro-1-hydroxy-1-trifluoromethyl-ethyl)-indol-1-ylmethyl]-oxazol-2-yl}-phenol (example 114) and morpholine-4-carbonylchloride was prepared morpholine-4-carboxylic acid 3-{5-methyl-4-[2-methyl-5-(2,2,2-trifluoro-1-hydroxy-1-trifluoromethyl-ethyl)-indol-1-ylmethyl]-oxazol-2-yl}-phenyl ester, light yellow foam, MS: 598 (MH$^+$).

Example 116 dimethyl-carbamic acid 3-{5-methyl-4-[2-methyl-5-(2,2,2-trifluoro-1-hydroxy-1-trifluoromethyl-ethyl)-indol-1-ylmethyl]-oxazol-2-yl}-phenyl ester In analogy to example 100, from 3-{5-methyl-4-[2-methyl-5-(2,2,2-trifluoro-1-hydroxy-1-trifluoromethyl-ethyl)-indol-1-ylmethyl]-oxazol-2-yl}-phenol (example 114) and dimethylcarbamoylchloride was prepared dimethyl-carbamic acid 3-{5-methyl-4-[2-methyl-5-(2,2,2-trifluoro-1-hydroxy-1-trifluoromethyl-ethyl)-indol-1-ylmethyl]-oxazol-2-yl}-phenyl ester, light yellow solid, MS: 556 (MH$^+$).

Example 117 pyrrolidine-1-carboxylic acid 3-{5-methyl-4-[2-methyl-5-(2,2,2-trifluoro-1-hydroxy-1-trifluoromethyl-ethyl)-indol-1-ylmethyl]-oxazol-2-yl}-phenyl ester In analogy to example 100, from 3-{5-methyl-4-[2-methyl-5-(2,2,2-trifluoro-1-hydroxy-1-trifluoromethyl-ethyl)-indol-1-ylmethyl]-oxazol-2-yl}-phenol (example 114) and 1-pyrrolidine-carbonylchloride was prepared pyrrolidine-1-carboxylic acid 3-{5-methyl-4-[2-methyl-5-(2,2,2-trifluoro- 1-hydroxy-1-trifluoromethyl-ethyl)-indol-1-ylmethyl]-oxazol-2-yl}-phenyl ester, white solid, MS: 582 (MH⁺).

Example 118

(3-{5-methyl-4-[2-methyl-5-(2,2,2-trifluoro-1-hydroxy-1-trifluoromethyl-ethyl)-indol-1-ylmethyl]-oxazol-2'-yl}-phenoxy)-acetic acid methyl ester In analogy to example 83, from 3-{5-methyl-4-[2-methyl-5-(2,2,2-trifluoro-1-hydroxy-1-trifluoromethyl-ethyl)-indol-1-ylmethyl]-oxazol-2-yl}-phenol (example 114) and methyl bromoacetate was prepared (3-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetic acid methyl ester, off white gum, MS: 557 (MH⁺).

Example 119

3-{5-methyl-4-[2-methyl-5-(2,2,2-trifluoro-1-hydroxy-1-trifluoromethyl-ethyl)-indol-1-ylmethyl]-oxazol-2-yl}-benzoic acid methyl ester In analogy to example 1, from (3-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester (example 90) was prepared 3-{5-methyl-4-[2-methyl-5-(2,2,2-trifluoro-1-hydroxy-1-trifluoromethyl-ethyl)-indol-1-ylmethyl]-oxazol-2-yl}-benzoic acid methyl ester, orange solid, MS: 527 (MH⁺).

Example 120

4-{5-methyl-4-[2-methyl-5-(2,2,2-trifluoro-1-hydroxy-1-trifluoromethyl-ethyl)-indol-1-ylmethyl]-oxazol-2-yl}-benzoic acid methyl ester In analogy to example 1, from (4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester (example 89) was prepared 4-{5-methyl-4-[2-methyl-5-(2,2,2-trifluoro-1-hydroxy-1-trifluoromethyl-ethyl)-indol-1-ylmethyl]-oxazol-2-yl}-benzoic acid methyl ester, light brown solid, MS: 527 (MH⁺).

Example 121

3-{5-methyl-4-[2-methyl-5-(2,2,2-trifluoro-1-hydroxy-1-trifluoromethyl-ethyl)-indol-1-ylmethyl]-oxazol-2-yl}-benzoic acid In analogy to example 91, from 3-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester (example 120) was prepared 3-{5-methyl-3-[2-methyl-5-(2,2,2-trifluoro-1-hydroxy-1-trifluoromethyl-ethyl)-indol-1-ylmethyl]-oxazol-2-yl}-benzoic acid, brown solid, MS: 513 (MH⁺).

Example 122

1,1,1,3,3,3-hexafluoro-2-{1-[2-(3-hydroxymethyl-phenyl)-5-methyl-oxazol-4-ylmethyl]-2-methyl-1H-indol-5-yl}-propan-2-ol In analogy to example 111, from 3-{5-methyl-4-[2-methyl-5-(2,2,2-trifluoro-1-hydroxy-1-trifluoromethyl-ethyl)-indol-1-ylmethyl]-oxazol-2-yl}-benzoic acid methyl ester (example 119) was prepared 1,1,1,3,3,3-hexafluoro-2-{1-[2-(3-hydroxymethyl-phenyl)-5-methyl-oxazol-4-ylmethyl]-2-methyl-1H-indol-5-yl}-propan-2-ol, yellow oil, MS: 499 (MH⁺).

Example 123

4-{5-methyl-4-[2-methyl-5-(2,2,2-trifluoro-1-hydroxy-1-trifluoromethyl-ethyl)-indol-1-ylmethyl]-oxazol-2-yl}-benzoic acid In analogy to example 91, from 4-{5-methyl-4-[2-methyl-5-(2,2,2-trifluoro-1-hydroxy-1-trifluoromethyl-ethyl)-indol-1-ylmethyl]-oxazol-2-yl}-benzoic acid methyl ester (example 119) was prepared 4-{5-methyl-4-[2-methyl-5-(2,2,2-trifluoro-1-hydroxy-1-trifluoromethyl-ethyl)-indol-1-ylmethyl]-oxazol-2-yl}-benzoic acid, orange solid, MS: 511 (M–H)⁻.

Example 124

N,N-dimethyl-3-{5-methyl-4-[2-methyl-5-(2,2,2-trifluoro-1-hydroxy-1-trifluoromethyl-ethyl)-indol-1-ylmethyl]-oxazol-2-yl}-benzamide In analogy to example 34, from 3-{5-methyl-4-[2-methyl-5-(2,2,2-trifluoro-1-hydroxy-1-trifluoromethyl-ethyl)-indol-1-ylmethyl]-oxazol-2-yl}-benzoic acid (example 121) was prepared N,N-dimethyl-3-{5-methyl-4-[2-methyl-5-(2,2,2-trifluoro-1-hydroxy-1-trifluoromethyl-ethyl)-indol-1-ylmethyl]-oxazol-2-yl}-benzamide, off-white solid, MS: 540 (MH⁺).

Example 125

(3-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetic acid In analogy to example 91, from (3-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetic acid methyl ester (example 118) was prepared (3-{5-methyl-4-[2-methyl-5-(2,2,2-trifluoro-1-hydroxy-1-trifluoromethyl-ethyl)-indol-1-ylmethyl]-oxazol-2-yl}-phenoxy)-acetic acid, pink solid, MS: 541 (M–H)⁻.

Example 126

N,N-dimethyl-4-{5-methyl-4-[2-methyl-5-(2,2,2-trifluoro-1-hydroxy-1-trifluoromethyl-ethyl)-indol-1-ylmethyl]-oxazol-2-yl}-benzamide In analogy to example 91, from 4-{5-methyl-4-[2-methyl-5-(2,2,2-trifluoro-1-hydroxy-1-trifluoromethyl-ethyl)-indol-1-ylmethyl]-oxazol-2-yl}-benzoic acid (example 123) was prepared N,N-dimethyl-4-{5-methyl-4-[2-methyl-5-(2,2,2-trifluoro-1-hydroxy-1-trifluoromethyl-ethyl)-indol-1-ylmethyl]-oxazol-2-yl}-benzamide, off-white solid, MS: 540 (MH⁺).

Example 127

1,1,1,3,3,3-hexafluoro-2-{1-[2-(4-hydroxymethyl-phenyl)-5-methyl-oxazol-4-ylmethyl]-2-methyl-1H-indol-5-yl}-propan-2-ol In analogy to example 111, from 4-{5-methyl-4-[2-methyl-5-(2,2,2-trifluoro-1-hydroxy-1-trifluoromethyl-ethyl)-indol-1-ylmethyl]-oxazol-2-yl}-benzoic acid methyl ester (example 120) was prepared 1,1,1,3,3,3-hexafluoro-2-{1-[2-(4-hydroxymethyl-phenyl)-5-methyl-oxazol-4-ylmethyl]-2-methyl-1H-indol-5-yl}-propan-2-ol, yellow oil, MS: 499 (MH$^+$).

Example 128

2-[2,3-dimethyl-1-(5-methyl-2-phenyl-oxazol-4-ylmethyl)-1H-indol-5-yl]-1,1,1,3,3,3-hexafluoro-propan-2-ol 128.1

A solution of 200 mg (0.4 mmol) of 2-{1-[2-(3-chloro-phenyl)-5-methyl-oxazol-4-ylmethyl]-2-methyl-1H-indol-5-yl}-1,1,1,3,3,3-hexafluoro-propan-2-ol (example 12) in 2 mL of dichloroethane was treated with 0.06 mL (0.8 mmol) of DMF and cooled to 0° C. After addition of 0.04 mL (0.44 mmol) of POCl$_3$ the mixture was allowed to reach RT and stirred for an additional hour. Distribution of the mixture between Et$_2$O and H$_2$O, drying of the combined organic phases over Na$_2$SO$_4$ and column chromatography on silica gel with n-heptane/EtOAc 1:2 yielded 110 mg (52%) of 1-[2-(3-chloro-phenyl)-5-methyl-oxazol-4-ylmethyl]-2-methyl-5-(2,2,2-trifluoro-1-hydroxy-1-trifluoromethyl-ethyl)-1H-indole-3-carbaldehyde, light brown solid, MS: 531 (MH$^+$).

128.2

A solution of 50 mg of 1-[2-(3-chloro-phenyl)-5-methyl-oxazol-4-ylmethyl]-2-methyl-5-(2,2,2-trifluoro-1-hydroxy-1-trifluoromethyl-ethyl)-1H-indole-3-carbaldehyde in 1 mL of THF was treated at 0° C. with 5 mg (0.14 mmol) of LiAlH$_4$ and allowed to reach RT within 1 h. Ice cubes were added and the mixture distributed between Et$_2$O and H$_2$O. Drying of the combined organic phases over Na$_2$SO$_4$ and evaporation of the solvent yielded 36 mg of 2-{1-[2-(3-chloro-phenyl)-5-methyl-oxazol-4-ylmethyl]-3-hydroxymethyl-2-methyl-1H-indol-5-yl}-1,1,1,3,3,3-hexafluoro-propan-2-ol, off white solid, 533 (MH$^+$).

128.3

A solution of 25 mg of 2-{1-[2-(3-chloro-phenyl)-5-methyl-oxazol-4-ylmethyl]-3-hydroxymethyl-2-methyl-1H-indol-5-yl}-1,1,1,3,3,3-hexafluoro-propan-2-ol in 1 mL of MeOH was treated with Pd/C (10% Pd) and stirred under H$_2$ at atmospheric pressure for 8 hrs. Filtration and evaporation of the solvent yielded 2-[2,3-dimethyl-1-(5-methyl-2-phenyl-oxazol-4-ylmethyl)-1H-indol-5-yl]-1,1,1,3,3,3-hexafluoro-propan-2-ol, light brown solid, 483 (MH$^+$).

Example 129

1,1,1,3,3,3-hexafluoro-2-[2-methyl-1-(5-methyl-2-o-tolyl-oxazol-4-ylmethyl)-1H-indol-5-yl]-propan-2-ol In analogy to example 1, from 1,1,1,3,3,3-hexafluoro-2-[2-methyl-1-(5-methyl-2-o-tolyl-oxazol-4-ylmethyl)-2,3-dihydro-1H-indol-5-yl]-propan-2-ol (example 46), was prepared 1,1,1,3,3,3-hexafluoro-2-[2-methyl-1-(5-methyl-2-o-tolyl-oxazol-4-ylmethyl)-1H-indol-5-yl]-propan-2-ol, brown oil, MS: 483 (MH$^+$).

Example 130

2-(2-chloro-phenyl)-4-[2-methyl-5-(2,2,2-trifluoro-1-hydroxy-1-trifluoromethyl-ethyl)-indol-1-ylmethyl]-oxazole-5-carboxylic acid methyl ester In analogy to example 1, from 2-(2-chloro-phenyl)-4-[2-methyl-5-(2,2,2-trifluoro-1-hydroxy-1-trifluoromethyl-ethyl)-2,3-dihydro-indol-1-ylmethyl]-oxazole-5-carboxylic acid methyl ester (example 45), was prepared 2-(2-chloro-phenyl)-4-[2-methyl-5-(2,2,2-trifluoro-1-hydroxy-1-trifluoromethyl-ethyl)-indol-1-ylmethyl]-oxazole-5-carboxylic acid methyl ester, light yellow semisolid, MS: 545 (M−H).

Example 131

1,1,1,3,3,3-hexafluoro-2-[2-methyl-1-(5-methyl-3-phenyl-isoxazol-4-ylmethyl)-1H-indol-5-yl]-propan-2-ol In analogy to example 1, from 1,1,1,3,3,3-hexafluoro-2-[2-methyl-1-(5-methyl-3-phenyl-isoxazol-4-ylmethyl)-2,3-dihydro-1H-indol-5-yl]-propan-2-ol (example 44), was prepared 1,1,1,3,3,3-hexafluoro-2-[2-methyl-1-(5-methyl-3-phenyl-isoxazol-4-ylmethyl)-1H-indol-5-yl]-propan-2-ol, light yellow oil, MS: 469 (MH$^+$).

Example 132

1,1,1,3,3,3-hexafluoro-2-{1-[3-(4-fluoro-phenoxy)-benzyl]-2-methyl-1H-indol-5-yl}-propan-2-ol In analogy to example 1, from 1,1,1,3,3,3-hexafluoro-2-{1-[3-(4-fluoro-phenoxy)-benzyl]-2-methyl-2,3,-dihydro-1H-indol-5-yl}-propan-2-ol (example 72), was prepared 1,1,1,3,3,3-hexafluoro-2-{1-[3-(4-fluoro-phenoxy)-benzyl]-2-methyl-1H-indol-5-yl}-propan-2-ol, red solid, MS: 498 (MH$^+$).

Example 133

1,1,1,3,3,3-hexafluoro-2-(2-methyl-1-naphthalen-2-ylmethyl-1H-indol-5-yl)-propan-2-ol 133.1

In analogy to example 51.3, from 2-methyl-5-(2,2,2-trifluoro-1-triethylsilanyloxy-1-trifluoromethyl-ethyl)-2,3-dihydro-1H-indole (example 51.2) and 2-bromomethyl-naphthalene was prepared 1,1,1,3,3,3-hexafluoro-2-(2-methyl-1-naphthalen-2-ylmethyl-2,3-dihydro-1H-indol-5-yl)-propan-2-ol, red oil, MS: 440 (MH$^+$).

133.2

In analogy to example 1, from 1,1,1,3,3,3-hexafluoro-2-(2-methyl-1-naphthalen-2-ylmethyl-2,3-dihydro-1H-indol-5-yl)-propan-2-ol, was prepared 1,1,1,3,3,3-hexafluoro-2-(2-methyl-1-naphthalen-2-ylmethyl-1H-indol-5-yl)-propan-2-ol, red solid, MS: 438 (MH$^+$).

Example 134

1,1,1,3,3,3-hexafluoro-2-{2-methyl-1-[2-methyl-6-(4-trifluoromethyl-phenyl)-pyridin-3-ylmethyl]-1H-indol-5-yl}-propan-2-ol In analogy to example 1, from 1,1,1,3,3,3-hexafluoro-2-{2-methyl-1-[2-methyl-6-(4-trifluoromethyl-phenyl)-pyridin-3-ylmethyl]-2,3-dihydro-1H-indol-5-yl}-propan-2-ol (example 74), was prepared 1,1,1,3,3,3-hexafluoro-2-{2-methyl-1-[2-methyl-6-(4-trifluoromethyl-phenyl)-pyridin-3-ylmethyl]-1H-indol-5-yl}-propan-2-ol, light brown solid, MS: 546 (MH$^+$).

Example 135

{3-[2-methyl-5-(2,2,2-trifluoro-1-hydroxy-1-trifluoromethyl-ethyl)-indol-1-ylmethyl]-phenyl}-piperidin-1-yl-methanone In analogy to example 34, from 3-{5-methyl-3-[2-methyl-5-(2,2,2-trifluoro-1-hydroxy-1-trifluoromethyl-ethyl)-indol-1-ylmethyl]-oxazol-2-yl}-benzoic acid (example 121) and piperidine was prepared {3-[2-methyl-5-(2,2,2-trifluoro-1-hydroxy-1-trifluoromethyl-ethyl)-indol-1-ylmethyl]-phenyl}-piperidin-1-yl-methanone, colorless solid, MS: 499 (MH$^+$).

Example 136 trans 1,1,1,3,3,3-hexafluoro-2-[2-methyl-1-(5-methyl-2-styryl-oxazol-4-ylmethyl)-2,3-dihydro-1H-indol-5-yl]-propan-2-ol 136.1
trans 4-chloromethyl-5-methyl-2-styryl-oxazole was prepared from cinnamaldehyde in analogy to the procedure by Binggeli et al. (WO200292084).

136.2
In analogy to example 75.2, from 1,1,1,3,3,3-hexafluoro-2-(2-methyl-2,3-dihydro-1H-indol-5-yl)-propan-2-ol (example 51.1) and trans 4-chloromethyl-5-methyl-2-styryl-oxazole was prepared trans 1,1,1,3,3,3-hexafluoro-2-[2-methyl-1-(5-methyl-2-styryl-oxazol-4-ylmethyl)-2,3-dihydro-1H-indol-5-yl]-propan-2-ol, orange solid, MS: 497 (MH$^+$).

Example 137

2-[1-(2-benzyl-5-methyl-oxazol-4-ylmethyl)-2-methyl-2,3-dihydro-1H-indol-5-yl]-1,1,1,3,3,3-hexafluoro-propan-2-ol 137.1
benzyl-4-chloromethyl-5-methyl-oxazole was prepared from phenylacetaldehyde in analogy to the procedure by Binggeli et al. (WO200292084).

137.2
In analogy to example 75.2, from 1,1,1,3,3,3-hexafluoro-2-(2-methyl-2,3-dihydro-1H-indol-5-yl)-propan-2-ol (example 51.1) and 2-benzyl-4-chloromethyl-5-methyl-oxazole was prepared 1,1,1,3,3,3-hexafluoro-2-[2-methyl-1-(5-methyl-2-styryl-oxazol-4-ylmethyl)-2,3-dihydro-1H-indol-5-yl]-propan-2-ol, red oil, MS: 485 (MH$^+$).

Example 138

1,1,1,3,3,3-hexafluoro-2-[2-methyl-1-(5-methyl-2-phenethyl-oxazol-4-ylmethyl)-2,3-dihydro-1H-indol-5-yl]-propan-2-ol A solution of 30 mg (0.06 mmol) of 1,1,1,3,3,3-hexafluoro-2-[2-methyl-1-(5-methyl-2-styryl-oxazol-4-ylmethyl)-2,3-dihydro-1H-indol-5-yl]-propan-2-ol (example 136) in 1 ml of methanol was treated with 15 mg of Pd/C (10%) and stirred under H$_2$ at atmospheric pressure for 6 hours. Filtration and evaporation of the solvent gave 24 mg (77%) of 1,1,1,3,3,3-hexafluoro-2-[2-methyl-1-(5-methyl-2-phenethyl-oxazol-4-ylmethyl)-2,3-dihydro-1H-indol-5-yl]-propan-2-ol, light yellow oil, MS: 499 (MH$^+$).

Example 139

4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenol A solution of 1.2 g (2.1 mmol) of 2-{1-[2-(4-benzyloxy-phenyl)-5-methyl-oxazol-4-ylmethyl]-2-methyl-2,3-dihydro-1H-indol-5-yl}-1,1,1,3,3,3-hexafluoro-propan-2-ol (example 79) in 15 ml of a 2:1-mixture of methanol and tetrahydrofuran was treated with 400 mg of Pd/C (10% Pd) and stirred vigorously under H$_2$ at atmospheric pressure during 10 hrs. Filtration, evaporation of the solvent, and chromatography on silica gel with toluene/EtOAc (gradient from 9:1 to 1:1) gave 390 mg (39%) of 4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-phenol, light yellow foam, MS: 487 (MH$^+$).

Example 140

1,1,1,3,3,3-hexafluoro-2-[2-methyl-1-(5-methyl-2-phenethyl-oxazol-4-ylmethyl)-1H-indol-5-yl]-propan-2-ol In analogy to example 1, from 1,1,1,3,3,3-hexafluoro-2-[2-methyl-1-(5-methyl-2-phenethyl-oxazol-4-ylmethyl)-2,3-dihydro-1H-indol-5-yl]-propan-2-ol (example 138) was prepared 1,1,1,3,3,3-hexafluoro-2-[2-methyl-1-(5-methyl-2-phenethyl-oxazol-4-ylmethyl)-1H-indol-5-yl]-propan-2-ol, light brown solid, MS: 497 (MH$^+$).

Example 141

1,1,1,3,3,3-hexafluoro-2-{1-[2-(3-hydroxymethyl-phenyl)-5-methyl-oxazol-4-ylmethyl]-2-methyl-2,3-dihydro-1H-indol-5-yl}-propan-2-ol A solution of 1.25 g (2.37 mmol) of 3-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester (example 90) in 15 ml of THF was treated at 0° C. with 180 mg (4.73 mmol) of lithium aluminium hydride and allowed to reach RT within 3 hrs. Distribution of the crude between a saturated aqueous solution of NH$_4$Cl and EtOAc, drying of the combined organic phases over Na$_2$SO$_4$ and evaporation of the solvent gave 1.1 g (93%) of 1,1,1,3,3,3-hexafluoro-2-{1-[2-(3-hydroxymethyl-phenyl)-5-methyl-oxazol-4-ylmethyl]-2-methyl-2,3-dihydro-1H-indol-5-yl}-propan-2-ol, off-white foam, MS : 499 (M−H)$^-$.

Example 142

1,1,1,3,3,3-hexafluoro-2-{1-[2-(4-hydroxymethyl-phenyl)-5-methyl-oxazol-4-ylmethyl]-2-methyl-2,3-dihydro-1H-indol-5-yl}-propan-2-ol In analogy to example 141, from 4-{5-methyl-4-[2-methyl-5-(2,2,2-trifluoro-1-hydroxy-1-trifluoromethyl-ethyl)-2,3-dihydro-indol-1-ylmethyl]-oxazol-2-yl}-benzoic acid methyl ester (example 89) was prepared 1,1,1,3,3,3-hexafluoro-2-{1-[2-(4-hydroxymethyl-phenyl)-5-methyl-oxazol-4-ylmethyl]-2-methyl-2,3-dihydro-1H-indol-5-yl}-propan-2-ol, light brown solid, MS : 499 (M−H)⁻.

Example 143

1,1,1,3,3,3-hexafluoro-2-(1-{2-[4-(1-hydroxy-ethyl)-phenyl]-5-methyl-oxazol-4-ylmethyl}-2-methyl-1H-indol-5-yl)-propan-2-ol 143.1

A solution of 100 mg (0.2 mmol) of 1,1,1,3,3,3-hexafluoro-2-{1-[2-(4-hydroxymethyl-phenyl)-5-methyl-oxazol-4-ylmethyl]-2-methyl-2,3-dihydro-1H-indol-5-yl}-propan-2-ol in 2 ml of toluene was treated with 87 mg (1.0 mmol) of $MnO_2$ and stirred at 80° C. during 20 hours. Filtration, evaporation of the solvent and chromatography on silica gel with heptane/EtOAc 4:1 gave 50 mg (50%) of 4-{5-methyl-4-[2-methyl-5-(2,2,2-trifluoro-1-hydroxy-1-trifluoromethyl-ethyl)-indol-1-ylmethyl]-oxazol-2-yl}-benzaldehyde, pink solid, MS: 497 (MH⁺).

143.2

A solution of 50 mg (0.1 mmol) of 4-{5-methyl-4-[2-methyl-5-(2,2,2-trifluoro-1-hydroxy-1-trifluoromethyl-ethyl)-indol-1-ylmethyl]-oxazol-2-yl}-benzaldehyde in 1 ml of THF was cooled to 0° C. and treated with 0.13 ml (0.4 mmol) of a 3M methylmagnesium bromide solution in diethylether. The mixture was stirred and allowed to reach RT within 1 hr. Distribution of the crude between a saturated aqueous solution of $NH_4Cl$ and EtOAc, drying of the combined organic phases over $Na_2SO_4$, evaporation of the solvent, and chromatography on silica gel with heptane/EtOAc 4:1 gave 44 mg (85%) of 1,1,1,3,3,3-hexafluoro-2-(1-{2-[4-(1-hydroxy-ethyl)-phenyl]-5-methyl-oxazol-4-ylmethyl}-2-methyl-1H-indol-5-yl)-propan-2-ol, off-white solid, MS: 513 (MH⁺).

Example 144

1,1,1,3,3,3-hexafluoro-2-(1-{2-[3-(1-hydroxy-ethyl)-phenyl]-5-methyl-oxazol-4-ylmethyl}-2-methyl-1H-indol-5-yl)-propan-2-ol 144.1

In analogy to example 143.1, from 1,1,1,3,3,3-hexafluoro-2-{1-[2-(3-hydroxymethyl-phenyl)-5-methyl-oxazol-4-ylmethyl]-2-methyl-2,3-dihydro-1H-indol-5-yl}-propan-2-ol was prepared 3-{5-methyl-4-[2-methyl-5-(2,2,2-trifluoro-1-hydroxy-1-trifluoromethyl-ethyl)-indol-1-ylmethyl]-oxazol-2-yl}-benzaldehyde, pink solid, MS: 497 (MH⁺).

144.2

In analogy to example 143.2, from 3-{5-methyl-4-[2-methyl-5-(2,2,2-trifluoro-1-hydroxy-1-trifluoromethyl-ethyl)-indol-1-ylmethyl]-oxazol-2-yl}-benzaldehyde was prepared 1,1,1,3,3,3-hexafluoro-2-(1-{2-[3-(1-hydroxy-ethyl)-phenyl]-5-methyl-oxazol-4-ylmethyl}-2-methyl-1H-indol-5-yl)-propan-2-ol, off-white solid, MS: 513 (MH⁺).

Examples 145 and 146

(2R) 1,1,1,3,3,3-hexafluoro-2-{2-methyl-1-[5-methyl-2-(3-trifluoromethyl-phenyl)-oxazol-4-ylmethyl]-2,3-dihydro-1H-indol-5-yl}-propan-2-ol and (2S) 1,1,1,3,3,3-hexafluoro-2-{2-methyl-1-[5-methyl-2-(3-trifluoromethyl-phenyl)-oxazol-4-ylmethyl]-2,3-dihydro-1H-indol-5-yl}-propan-2-ol Chiral HPLC of 900 mg (1.68 mmol) of racemic 1,1,1,3,3,3-hexafluoro-2-{2-methyl-1-[5-methyl-2-(3-trifluoromethyl-phenyl)-oxazol-4-ylmethyl]-2,3-dihydro-1H-indol-5-yl}-propan-2-ol (example 56) gave ca. 300 mg (33%) of (2R) 1,1,1,3,3,3-hexafluoro-2-{2-methyl-1-[5-methyl-2-(3-trifluoromethyl-phenyl)-oxazol-4-ylmethyl]-2,3-dihydro-1H-indol-5-yl}-propan-2-ol and ca. 300 mg (33%) of (2S) 1,1,1,3,3,3-hexafluoro-2-{2-methyl-1-[5-methyl-2-(3-trifluoromethyl-phenyl)-oxazol-4-ylmethyl]-2,3-dihydro-1H-indol-5-yl}-propan-2-ol, Colorless solids, MS: 539 (MH⁺).

Example 147

1,1,1,3,3,3-hexafluoro-2-[2-methyl-1-(5-methyl-2-pyridin-3-yl-oxazol-4-ylmethyl)-2,3-dihydro-1H-indol-5-yl]-propan-2-ol 147.1

3-(4-chloromethyl-5-methyl-oxazol-2-yl)-pyridine was prepared from 3-pyridinecarboxaldehyde in analogy to the procedure by Binggeli et al. (WO200292084).

147.2

In analogy to example 75.2, from 1,1,1,3,3,3-hexafluoro-2-(2-methyl-2,3-dihydro-1H-indol-5-yl)-propan-2-ol (example 51.1) and 3-(4-chloromethyl-5-methyl-oxazol-2-yl)-pyridine was prepared 1,1,1,3,3,3-hexafluoro-2-[2-methyl-1-(5-methyl-2-pyridin-3-yl-oxazol-4-ylmethyl)-2,3-dihydro-1H-indol-5-yl]-propan-2-ol, Light brown gum, MS: 472 (MH⁺).

Example 148

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example 149

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Example 150

The following tests were carried out in order to determine the activity of the compounds of the present invention. Background information on the performed assays can be found in: Nichols J S et al. "Development of a scintillation proximity assay for peroxisome proliferator-activated receptor gamma ligand binding domain", Anal Biochem. 1998, 257: 112-119.

Mammalian expression vectors were constructed to express full-length human LXR alpha and LXR beta. Bacterial expression vectors were constructed to produce glutathione-s-transferase (GST) fused to the ligand binding domains (LBD) of human LXR alpha (aa 164 to 447) and human LXR beta (aa 155 to 460). To accomplish this, the portions of the sequences encoding the LBDs were amplified from full-length clones by PCR and then subcloned into the plasmid vectors. Final clones were verified by DNA sequence analysis (Willy et al., Genes Dev. 1995, 9:1033-45; Song et al., Proc Natl Acad Sci USA.1994, 91:10809-13).

Induction, expression, and purification of GST-LBD fusion proteins were performed in *E. coli* strain BL21(pLysS) cells by standard methods (Ref: Current Protocols in Molecular Biology, Wiley Press, edited by Ausubel et al).

Radioligand Binding Assay

LXR alpha and LXR beta receptor binding were assayed in buffer consisting of 50 mM HEPES, pH 7.4, 10 mM NaCl, 5 mM $MgCl_2$. For each 96-well reaction, 500 ng of GST-LXRα-LBD or 700 ng of GST-LXR beta-LBD fusion proteins were bound to 80 μg or 40 μg SPA beads (Pharmacia Amersham) respectively, in a final volume of 50 μl by shaking. The resulting slurry was incubated for 1 h at RT and centrifuged for 2 min at 1300×g. The supernatant containing unbound protein was removed, and the semi-dry pellet containing the receptor-coated beads was re-suspended in 50 μl of buffer. Radioligand (eg. 100,000 dpm of (N-(2,2,2-trifluoroethyl)-N-[4-(2,2,2-trifluoro-1-hydroxy-1-trifluoromethyl-ethyl)-phenyl]-benzenesulfonamide)) was added, and the reaction incubated at RT for 1 h in the presence of test compounds, and then scintillation proximity counting was performed. All binding assays were performed in 96-well plates and the amount of bound ligand was measured on a Packard TopCount using OptiPlates (Packard). Dose response curves were measured within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% $O_2$:5% $CO_2$ atmosphere. Cells were seeded in 6-well plates at a density of $10^5$ Cells/well and then batch-transfected with either the full-length-LXRα or full-length-LXRβ expression plasmids plus a reporter plasmid expressing luciferase under the control of LXR response elements. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 μl of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula (I) have an activity in at least one of the above assays (EC50 or IC50) of 0.1 nM to 100 uM, preferably 0.1 nM to 1 uM. (uM means micromolar).

For example, the following compounds showed the following IC50 values in the binding assay:

| Example | LXRalpha Binding IC50 [umol/l] | LXRbeta Binding IC50 [umol/l] |
|---|---|---|
| 50 | 0.02 | 0.006 |
| 80 | 0.03 | 0.05 |

These results were obtained by using the foregoing test.

It is to be understood that the invention is not limited to the particular embodiments of the invention described above, as variations of the particular embodiments may be made and still fall within the scope of the appended claims.

The invention claimed is:

1. A method for the treatment of diabetes, comprising the step of administering a therapeutically effective amount of a compound according to formula (I):

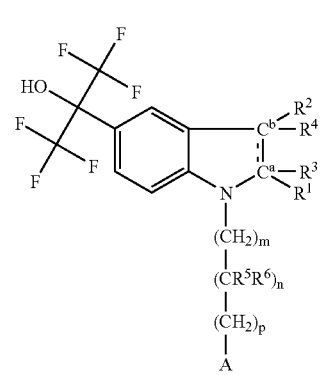

wherein:
  $R^1$ is hydrogen, alkyl, halogen, formyl, hydroxyalkyl or trifluoromethyl;
  $R^2$ is hydrogen, alkyl, alkenyl, alkynyl, cyano or halogen;
  $R^3$ is hydrogen or alkyl;
  $R^4$ is hydrogen, alkyl, hydroxy or alkoxy;
  $R^5$ and $R^6$ are independently selected from hydrogen, alkyl, arylalkyl, heteroarylalkyl, hydroxyalkyl, alkoxycarbonyl, aryl and heteroaryl;

A is aryl or heterocyclyl, wherein aryl and heterocyclyl are optionally substituted with one to three substituents independently selected from alkyl, halogen, amino, hydroxyalkyl, aryl, aryloxy, alkoxy, arylalkyl, arylalkenyl, alkoxycarbonylamino, aminocarbonyloxy, carboxy, alkoxycarbonyl, alkoxycarbonylalkyl, aminoalkyl, trifluoromethyl, arylalkylaminocarbonyl, alkoxycarbonylalkylaminocarbonyl, indolylalkylaminocarbonyl, morpholinylcarbonyl, aminocarbonyl, aminocarbonylalkyl, aminocarbonylalkoxy, alkoxycarbonylalkoxy, pyridinylalkylaminocarbonyl, alkyloxycarbonylalkylaryl, alkyloxycarbonylalkoxyaryl, carboxyalkylaryl, carboxyalkoxyaryl, aminocarbonylalkylaryl, aminocarbonylalkoxyaryl, aminocarbonylamino, aminocarbonyloxy, aminocarbonyloxyaryl, carboxyalkyl, carboxyalkoxy, cycloalkylaminocarbonyl, morpholinylcarbonyloxyaryl, morpholinylcarbonylaryl, arylalkoxyaryl, aminocarbonylaryl, pyrrolidinylcarbonyloxyaryl, pyrrolidinylcarbonylaryl, piperidinylcarbonylaryl, piperidinylcarbonyloxyaryl, hydroxyalkylaryl, hydroxy(carboxy)alkylaryl, hydroxy(alkoxycarbonyl)alkylaryl, hydroxy(aminocarbonyl)alkylaryl morpholinyalalkyl, arylalkylaminocarbonyl, alkoxycarbonylalkylaminocarbonyl, trifluoromethylaryl, alkoxyaryl, alkylaryl, halogenaryl, alkoxycarbonylaryl, carboxyaryl, hydroxyaryl and pyridinyl;

m is zero, 1, 2 or 3;

n is zero or 1;

p is zero, 1, 2 or 3; with the proviso that the sum of m, n and p is 1, 2, 3 or 4;

and, wherein the compound is not 2-(1-benzyl-2,3-dihydro-1H-indol-5-yl)-1,1,1,3,3,3-hexafluoro-propan-2-ol;

and, wherein the bond between the carbon atoms $C^a$ and $C^b$ is a carbon carbon single or double bond and in case the bond between $C^a$ and $C^b$ is a carbon carbon double bond $R^3$ and $R^4$ are absent;

and pharmaceutically acceptable salts and pharmaceutically acceptable esters thereof, to a patient in need thereof.

2. A method for the treatment of diseases which are modulated by LXR alpha and/or LXR beta agonists, comprising the step of administering a therapeutically effective amount of a compound according to formula (I):

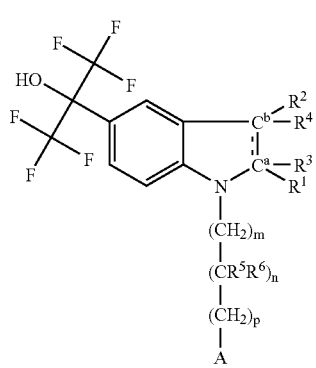

(I)

wherein:

$R^1$ is hydrogen, alkyl, halogen, formyl, hydroxyalkyl or trifluoromethyl;

$R^2$ is hydrogen, alkyl, alkenyl, alkynyl, cyano or halogen;

$R^3$ is hydrogen or alkyl;

$R^4$ is hydrogen, alkyl, hydroxy or alkoxy;

$R^5$ and $R^6$ are independently selected from hydrogen, alkyl, arylalkyl, heteroarylalkyl, hydroxyalkyl, alkoxycarbonyl, aryl and heteroaryl;

A is aryl or heterocyclyl, wherein aryl and heterocyclyl are optionally substituted with one to three substituents independently selected from alkyl, halogen, amino, hydroxyalkyl, aryl, aryloxy, alkoxy, arylalkyl, arylalkenyl, alkoxycarbonylamino, aminocarbonyloxy, carboxy, alkoxycarbonyl, alkoxycarbonylalkyl, aminoalkyl, trifluoromethyl, arylalkylaminocarbonyl, alkoxycarbonylalkylaminocarbonyl, indolylalkylaminocarbonyl, morpholinylcarbonyl, aminocarbonyl, aminocarbonylalkyl, aminocarbonylalkoxy, alkoxycarbonylalkoxy, pyridinylalkylaminocarbonyl, alkyloxycarbonylalkylaryl, alkyloxycarbonylalkoxyaryl, carboxyalkylaryl, carboxyalkoxyaryl, aminocarbonylalkylaryl, aminocarbonylalkoxyaryl, aminocarbonylamino, aminocarbonyloxy, aminocarbonyloxyaryl, carboxyalkyl, carboxyalkoxy, cycloalkylaminocarbonyl, morpholinylcarbonyloxyaryl, morpholinylcarbonylaryl, arylalkoxyaryl, aminocarbonylaryl, pyrrolidinylcarbonyloxyaryl, pyrrolidinylcarbonylaryl, piperidinylcarbonylaryl, piperidinylcarbonyloxyaryl, hydroxyalkylaryl, hydroxy(carboxy)alkylaryl, hydroxy(alkoxycarbonyl)alkylaryl, hydroxy(aminocarbonyl)alkylaryl, morpholinylalkyl, arylalkylaminocarbonyl, alkoxycarbonylalkylaminocarbonyl, trifluoromethylaryl, alkoxyaryl, alkylaryl, halogenaryl, alkoxycarbonylaryl, carboxyaryl, hydroxyaryl, and pyridinyl;

m is zero, 1, 2 or 3;

n is zero or 1;

p is zero, 1, 2 or 3; with the proviso that the sum of m, n and p is 1, 2, 3 or 4;

and, wherein the compound is not 2-(1-benzyl-2,3-dihydro-1H-indol-5-yl)-1,1,1,3,3,3-hexafluoro-propan-2-ol;

and, wherein the bond between the carbon atoms $C^a$ and $C^b$ carbon carbon single or double bond and in case the bond between $C^a$ and $C^b$ is a carbon carbon double bond $R^3$ and $R^4$ are absent;

and pharmaceutically acceptable salts and pharmaceutically acceptable esters thereof, to a patient in need thereof, wherein the disease is increased lipid levels, increased cholesterol levels, low HDL-cholesterol, high LDL-cholesterol, atherosclerotic diseases, diabetes, macular degeneration or Alzheimer's disease.

* * * * *